(12) United States Patent
Leonard et al.

(10) Patent No.: US 8,039,219 B2
(45) Date of Patent: Oct. 18, 2011

(54) METHOD OF USING GPR35 TO IDENTIFY METABOLIC-STABILIZING COMPOUNDS

(75) Inventors: James N. Leonard, San Diego, CA (US); Zhi Liang Chu, San Diego, CA (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 1174 days.

(21) Appl. No.: 11/638,343

(22) Filed: Dec. 13, 2006

(65) Prior Publication Data

US 2007/0077602 A1    Apr. 5, 2007

Related U.S. Application Data

(63) Continuation-in-part of application No. 11/596,035, filed as application No. PCT/US2005/018082 on May 23, 2005, now abandoned.

(60) Provisional application No. 60/574,849, filed on May 26, 2004, provisional application No. 60/585,156, filed on Jul. 1, 2004, provisional application No. 60/612,862, filed on Sep. 24, 2004, provisional application No. 60/644,684, filed on Jan. 18, 2005, provisional application No. 60/647,969, filed on Jan. 27, 2005.

(51) Int. Cl.
*G01N 33/53* (2006.01)
*G01N 33/567* (2006.01)

(52) U.S. Cl. .......... 435/7.1; 435/7.2; 435/7.21
(58) Field of Classification Search ................ None
See application file for complete search history.

(56) References Cited

U.S. PATENT DOCUMENTS 5,296,605 A    3/1994    de Nanteuil et al.
5,661,168 A    8/1997    Panetta et al.

FOREIGN PATENT DOCUMENTS

JP    07 070095    3/1995
WO    9964452    12/1999

OTHER PUBLICATIONS

Horikawa, et al. Genetic variation in the gene encoding calpain-10 is associated with type 2 diabetes mellitus. Nat Genet. Oct. 2000;26(2):163-75.

*Primary Examiner* — Robert Landsman
(74) *Attorney, Agent, or Firm* — David C. Scherer; Bozicevic, Field & Francis LLP

(57) ABSTRACT

The present invention relates to a method for identifying a metabolic stabilizing compound, comprising: a) contacting a candidate compound with GPR35, and b) determining whether GPR35 functionality is increased, wherein an increase in GPR35 functionality is indicative of the candidate compound being a metabolic stabilizing compound. The invention further relates to a method for treating or preventing a metabolic-related disorder, comprising administering to an individual in need thereof an effective amount of a GPR35 modulator.

4 Claims, 8 Drawing Sheets

Marked Induction of GPR35 Expression in Liver and Pancreas of db/db Mice

SEQUENCE LISTING

<160> NUMBER OF SEQ ID NOS: 30

<210> SEQ ID NO 1
<211> LENGTH: 930
<212> TYPE: DNA
<213> ORGANISM: Homo sapien

<400> SEQUENCE: 1

```
atgaatggca cctacaacac ctgtggctcc agcgacctca cctggccccc agcgatcaag      60
ctgggcttct acgcctactt gggcgtcctg ctggtgctag cctgctgct caacagcctg      120
gcgctctggg tgttctgctg ccgcatgcag cagtggacgg agacccgcat ctacatgacc      180
aacctggcgg tggccgacct ctgcctgctg tgcaccttgc ccttcgtgct gcactccctg      240
cgagacacct cagacacgcc gctgtgccag ctctcccagg gcatctacct gaccaacagg      300
tacatgagca tcagcctggt cacggccatc gccgtggacc gctatgtggc cgtgcggcac      360
ccgctgcgtg cccgcgggct gcggtccccc aggcaggctg cggccgtgtg cgcggtcctc      420
tgggtgctgg tcatcggctc cctggtggct cgctggctcc tggggattca ggagggcggc      480
ttctgcttca ggagcacccg gcacaatttc aactccatgc ggttcccgct gctgggattc      540
tacctgcccc tggccgtggt ggtcttctgc tccctgaagg tggtgactgc cctgcccag      600
aggccaccca ccgacgtggg gcaggcagag gccacccgca aggctgcccg catggtctgg      660
gccaacctcc tggtgttcgt ggtctgcttc ctgcccctgc acgtggggct gacagtgcgc      720
ctcgcagtgg gctggaacgc ctgtgccctc ctggagacga tccgtcgcgc cctgtacata      780
accagcaagc tctcagatgc caactgctgc tggacgccca tctgctacta ctacatggcc      840
aaggagttcc aggaggcgtc tgcactggcc gtggctcccc gtgctaaggc ccacaaaagc      900
caggactctc tgtgcgtgac cctcgcctaa                                      930
```

<210> SEQ ID NO 2
<211> LENGTH: 309
<212> TYPE: PRT
<213> ORGANISM: Homo sapien

<400> SEQUENCE: 2

```
Met Asn Gly Thr Tyr Asn Thr Cys Gly Ser Ser Asp Leu Thr Trp Pro
  1               5                  10                  15

Pro Ala Ile Lys Leu Gly Phe Tyr Ala Tyr Leu Gly Val Leu Leu Val
                 20                  25                  30

Leu Gly Leu Leu Leu Asn Ser Leu Ala Leu Trp Val Phe Cys Cys Arg
             35                  40                  45

Met Gln Gln Trp Thr Glu Thr Arg Ile Tyr Met Thr Asn Leu Ala Val
         50                  55                  60

Ala Asp Leu Cys Leu Leu Cys Thr Leu Pro Phe Val Leu His Ser Leu
 65                  70                  75                  80

Arg Asp Thr Ser Asp Thr Pro Leu Cys Gln Leu Ser Gln Gly Ile Tyr
                 85                  90                  95

Leu Thr Asn Arg Tyr Met Ser Ile Ser Leu Val Thr Ala Ile Ala Val
            100                 105                 110

Asp Arg Tyr Val Ala Val Arg His Pro Leu Arg Ala Arg Gly Leu Arg
            115                 120                 125

Ser Pro Arg Gln Ala Ala Ala Val Cys Ala Val Leu Trp Val Leu Val
        130                 135                 140

Ile Gly Ser Leu Val Ala Arg Trp Leu Leu Gly Ile Gln Glu Gly Gly
```

```
                145                 150                 155                 160
Phe Cys Phe Arg Ser Thr Arg His Asn Phe Asn Ser Met Arg Phe Pro
                    165                 170                 175

Leu Leu Gly Phe Tyr Leu Pro Leu Ala Val Val Phe Cys Ser Leu
                180                 185                 190

Lys Val Val Thr Ala Leu Ala Gln Arg Pro Pro Thr Asp Val Gly Gln
            195                 200                 205

Ala Glu Ala Thr Arg Lys Ala Arg Met Val Trp Ala Asn Leu Leu
        210                 215                 220

Val Phe Val Val Cys Phe Leu Pro His Val Gly Leu Thr Val Arg
225                 230                 235                 240

Leu Ala Val Gly Trp Asn Ala Cys Ala Leu Leu Glu Thr Ile Arg Arg
                245                 250                 255

Ala Leu Tyr Ile Thr Ser Lys Leu Ser Asp Ala Asn Cys Cys Leu Asp
                260                 265                 270

Ala Ile Cys Tyr Tyr Tyr Met Ala Lys Glu Phe Gln Glu Ala Ser Ala
                275                 280                 285

Leu Ala Val Ala Pro Arg Ala Lys Ala His Lys Ser Gln Asp Ser Leu
        290                 295                 300

Cys Val Thr Leu Ala
305
```

<210> SEQ ID NO 3
<211> LENGTH: 930
<212> TYPE: DNA
<213> ORGANISM: Homo sapien

<400> SEQUENCE: 3

```
atgaatggca cctacaacac ctgtggctcc agcgacctca cctggccccc agcgatcaag    60
ctgggcttct acgcctactt gggcgtcctg ctggtgctag cctgctgct caacagcctg   120
gcgctctggg tgttctgctg ccgcatgcag cagtggacgg agacccgcat ctacatgacc   180
aacctggcgg tggccgacct ctgcctgctg tgcaccttgc ccttcgtgct gcactccctg   240
cgagacacct cagacacgcc gctgtgccag ctctcccagg catctacct gaccaacagg    300
tacatgagca tcagcctggt cacggccatc gccgtggacc gctatgtggc cgtgcggcac   360
ccgctgcgtg cccgcgggct gcggtccccc aggcaggctg cggccgtgtg cgcggtcctc   420
tgggtgctgg tcatcggctc cctggtggct cgctggctcc tggggattca ggagggcggc   480
ttctgcttca ggagcacccg gcacaatttc aactccatgg cgttcccgct gctgggattc   540
tacctgcccc tggccgtggt ggtcttctgc tccctgaagg tggtgactgc cctggcccag   600
aggccaccca ccgacgtggg gcaggcagag gccacccgca aggctgcccg catggtctgg   660
gccaacctcc tggtgttcgt ggtctgcttc ctgccctgc acgtggggct gacagtgcgc   720
ctcgcagtgg gctggaacgc ctgtgccctc tggagacga tccgtcgcgc cctgtacata   780
accagcaagc tctcagatgc caactgctgc ctggacgcca tctgctacta ctacatggcc   840
aaggagttcc aggaggcgtc tgcactggcc gtggctccca gtgctaaggc ccacaaaagc   900
caggactctc tgtgcgtgac cctcgcctaa                                    930
```

<210> SEQ ID NO 4
<211> LENGTH: 309
<212> TYPE: PRT
<213> ORGANISM: Homo sapien

<400> SEQUENCE: 4

Met Asn Gly Thr Tyr Asn Thr Cys Gly Ser Ser Asp Leu Thr Trp Pro
1               5                   10                  15

Pro Ala Ile Lys Leu Gly Phe Tyr Ala Tyr Leu Gly Val Leu Leu Val
            20                  25                  30

Leu Gly Leu Leu Leu Asn Ser Leu Ala Leu Trp Val Phe Cys Cys Arg
        35                  40                  45

Met Gln Gln Trp Thr Glu Thr Arg Ile Tyr Met Thr Asn Leu Ala Val
    50                  55                  60

Ala Asp Leu Cys Leu Leu Cys Thr Leu Pro Phe Val Leu His Ser Leu
65                  70                  75                  80

Arg Asp Thr Ser Asp Thr Pro Leu Cys Gln Leu Ser Gln Gly Ile Tyr
                85                  90                  95

Leu Thr Asn Arg Tyr Met Ser Ile Ser Leu Val Thr Ala Ile Ala Val
            100                 105                 110

Asp Arg Tyr Val Ala Val Arg His Pro Leu Arg Ala Arg Gly Leu Arg
        115                 120                 125

Ser Pro Arg Gln Ala Ala Ala Val Cys Ala Val Leu Trp Val Leu Val
    130                 135                 140

Ile Gly Ser Leu Val Ala Arg Trp Leu Leu Gly Ile Gln Glu Gly Gly
145                 150                 155                 160

Phe Cys Phe Arg Ser Thr Arg His Asn Phe Asn Ser Met Ala Phe Pro
                165                 170                 175

Leu Leu Gly Phe Tyr Leu Pro Leu Ala Val Val Val Phe Cys Ser Leu
            180                 185                 190

Lys Val Val Thr Ala Leu Ala Gln Arg Pro Pro Thr Asp Val Gly Gln
        195                 200                 205

Ala Glu Ala Thr Arg Lys Ala Ala Arg Met Val Trp Ala Asn Leu Leu
    210                 215                 220

Val Phe Val Val Cys Phe Leu Pro Leu His Val Gly Leu Thr Val Arg
225                 230                 235                 240

Leu Ala Val Gly Trp Asn Ala Cys Ala Leu Leu Glu Thr Ile Arg Arg
                245                 250                 255

Ala Leu Tyr Ile Thr Ser Lys Leu Ser Asp Ala Asn Cys Cys Leu Asp
            260                 265                 270

Ala Ile Cys Tyr Tyr Tyr Met Ala Lys Glu Phe Gln Glu Ala Ser Ala
        275                 280                 285

Leu Ala Val Ala Pro Ser Ala Lys Ala His Lys Ser Gln Asp Ser Leu
    290                 295                 300

Cys Val Thr Leu Ala
305

<210> SEQ ID NO 5
<211> LENGTH: 924
<212> TYPE: DNA
<213> ORGANISM: Mus musculus

<400> SEQUENCE: 5

```
atgaatagta caacctgtaa cagcaccctc acgtggcctg cttccgtcaa caacttcttc      60
atcatctact cagccttgct gctggtgctg ggcctgctgc tcaacagcgt ggcactctgg     120
gtattctgct atcgcatgca ccagtggaca gagacccgca tctatatgac caacctggct     180
gtggccgacc tctgcctgct ctgctccttg ccatttgtgc tgtactccct gaaatatagt     240
tcttcagaca caccgtctg ccagctctca cagggcatct acctggccaa cagatacatg     300
agcataagcc tggtcactgc cattgctgtg accgctatg tggcagtgcg gcatcccctg     360
```

-continued

```
cgtgcgcgtg agctgcggtc cccgagacag gctgcagcag tgtgtgtggc cctttgggtg    420
atagtggtca cctccctggt agtgcgctgg cgcctgggga tgcaggaggg tggcttctgc    480
ttcagcagcc aaacccggcg caatttcagc accactgcct tctcactgct gggattctac    540
ctgccgctgg ccatcgtggt cttctgctct ttgcaggtag tgactgtgct atcgagaagg    600
ccagccgctg atgtggggca ggcagaggcc acccaaaagg ccacccacat ggtctgggcc    660
aacttggctg tgtttgtcat ctgcttcctg cccttgcatg tggtcctgac cgtgcaggtc    720
tccctgaacc tcaataccct gctgcccga gacaccttca gccgtgccct gtccatcaca    780
ggtaaactct cagacaccaa ctgctgcctg atgccatct gttactacta catggccaga    840
gagttccagg aagcgtccaa gccagccacg tcttccaaca caccccacaa gagccaagat    900
tcccagatcc tgagcctcac ctag                                            924
```

<210> SEQ ID NO 6
<211> LENGTH: 307
<212> TYPE: PRT
<213> ORGANISM: Mus musculus

<400> SEQUENCE: 6

```
Met Asn Ser Thr Thr Cys Asn Ser Thr Leu Thr Trp Pro Ala Ser Val
1               5                   10                  15

Asn Asn Phe Phe Ile Ile Tyr Ser Ala Leu Leu Val Leu Gly Leu
            20                  25                  30

Leu Leu Asn Ser Val Ala Leu Trp Val Phe Cys Tyr Arg Met His Gln
        35                  40                  45

Trp Thr Glu Thr Arg Ile Tyr Met Thr Asn Leu Ala Val Ala Asp Leu
    50                  55                  60

Cys Leu Leu Cys Ser Leu Pro Phe Val Leu Tyr Ser Leu Lys Tyr Ser
65                  70                  75                  80

Ser Ser Asp Thr Pro Val Cys Gln Leu Ser Gln Gly Ile Tyr Leu Ala
                85                  90                  95

Asn Arg Tyr Met Ser Ile Ser Leu Val Thr Ala Ile Ala Val Asp Arg
            100                 105                 110

Tyr Val Ala Val Arg His Pro Leu Arg Ala Arg Glu Leu Arg Ser Pro
        115                 120                 125

Arg Gln Ala Ala Ala Val Cys Val Ala Leu Trp Val Ile Val Val Thr
    130                 135                 140

Ser Leu Val Val Arg Trp Arg Leu Gly Met Gln Glu Gly Gly Phe Cys
145                 150                 155                 160

Phe Ser Ser Gln Thr Arg Arg Asn Phe Ser Thr Thr Ala Phe Ser Leu
                165                 170                 175

Leu Gly Phe Tyr Leu Pro Leu Ala Ile Val Val Phe Cys Ser Leu Gln
            180                 185                 190

Val Val Thr Val Leu Ser Arg Arg Pro Ala Ala Asp Val Gly Gln Ala
        195                 200                 205

Glu Ala Thr Gln Lys Ala Thr His Met Val Trp Ala Asn Leu Ala Val
    210                 215                 220

Phe Val Ile Cys Phe Leu Pro Leu His Val Val Leu Thr Val Gln Val
225                 230                 235                 240

Ser Leu Asn Leu Asn Thr Cys Ala Ala Arg Asp Thr Phe Ser Arg Ala
                245                 250                 255

Leu Ser Ile Thr Gly Lys Leu Ser Asp Thr Asn Cys Cys Leu Asp Ala
            260                 265                 270

Ile Cys Tyr Tyr Tyr Met Ala Arg Glu Phe Gln Glu Ala Ser Lys Pro
```

```
              275                 280                 285
Ala Thr Ser Ser Asn Thr Pro His Lys Ser Gln Asp Ser Gln Ile Leu
            290                 295                 300

Ser Leu Thr
305

<210> SEQ ID NO 7
<211> LENGTH: 1023
<212> TYPE: DNA
<213> ORGANISM: Homo sapien

<400> SEQUENCE: 7
atgctgagtg gttcccgggc tgtccccact ccacaccgtg gcagtgaaga gctgctgaag      60
tacatgcttc atagtccttg cgtctctctg accatgaatg gcacctacaa cacctgtggc     120
tccagcgacc tcacctggcc cccagcgatc aagctgggct tctacgccta cttgggcgtc     180
ctgctggtgc taggcctgct gctcaacagc ctggcgctct gggtgttctg ctgccgcatg     240
cagcagtgga cggagacccg catctacatg accaacctgg cggtggccga cctctgcctg     300
ctgtgcacct tgcccttcgt gctgcactcc ctgcgagaca cctcagacac gccgctgtgc     360
cagctctccc agggcatcta cctgaccaac aggtacatga gcatcagcct ggtcacggcc     420
atcgccgtgg accgctatgt ggccgtgcgg cacccgctgc gtgcccgcgg gctgcggtcc     480
cccaggcagg ctgcggccgt gtgcgcggtc ctctgggtgc tggtcatcgg ctccctggtg     540
gctcgctggc tcctggggat tcaggagggc ggcttctgct tcaggagcac ccggcacaat     600
ttcaactcca tggcgttccc gctgctggga ttctacctgc ccctggccgt ggtggtcttc     660
tgctccctga aggtggtgac tgccctggcc agagaggcca cccaccgacgt ggggcaggca     720 gaggccaccc gcaaggctgc ccgcatggtc tgggccaacc tcctggtgtt cgtggtctgc     780
ttcctgcccc tgcacgtggg gctgacagtg cgcctcgcag tgggctggaa cgcctgtgcc     840
ctcctggaga cgatccgtcg cgccctgtac ataaccagca agctctcaga tgccaactgc     900
tgcctggacg ccatctgcta ctactacatg gccaaggagt tccaggaggc gtctgcactg     960
gccgtggctc ccagtgctaa ggcccacaaa agccaggact ctctgtgcgt gaccctcgcc    1020
taa                                                                 1023

<210> SEQ ID NO 8
<211> LENGTH: 340
<212> TYPE: PRT
<213> ORGANISM: Homo sapien

<400> SEQUENCE: 8

Met Leu Ser Gly Ser Arg Ala Val Pro Thr Pro His Arg Gly Ser Glu
1               5                   10                  15

Glu Leu Leu Lys Tyr Met Leu His Ser Pro Cys Val Ser Leu Thr Met
            20                  25                  30

Asn Gly Thr Tyr Asn Thr Cys Gly Ser Ser Asp Leu Thr Trp Pro Pro
        35                  40                  45

Ala Ile Lys Leu Gly Phe Tyr Ala Tyr Leu Gly Val Leu Leu Val Leu
    50                  55                  60

Gly Leu Leu Leu Asn Ser Leu Ala Leu Trp Val Phe Cys Cys Arg Met
65                  70                  75                  80

Gln Gln Trp Thr Glu Thr Arg Ile Tyr Met Thr Asn Leu Ala Val Ala
                85                  90                  95

Asp Leu Cys Leu Leu Cys Thr Leu Pro Phe Val Leu His Ser Leu Arg
            100                 105                 110
```

Asp Thr Ser Asp Thr Pro Leu Cys Gln Leu Ser Gln Gly Ile Tyr Leu
        115                 120                 125

Thr Asn Arg Tyr Met Ser Ile Ser Leu Val Thr Ala Ile Ala Val Asp
        130                 135                 140

Arg Tyr Val Ala Val Arg His Pro Leu Arg Ala Arg Gly Leu Arg Ser
145                 150                 155                 160

Pro Arg Gln Ala Ala Val Cys Ala Val Leu Trp Val Leu Val Ile
                165                 170                 175

Gly Ser Leu Val Ala Arg Trp Leu Leu Gly Ile Gln Glu Gly Gly Phe
                180                 185                 190

Cys Phe Arg Ser Thr Arg His Asn Phe Asn Ser Met Ala Phe Pro Leu
        195                 200                 205

Leu Gly Phe Tyr Leu Pro Leu Ala Val Val Val Phe Cys Ser Leu Lys
        210                 215                 220

Val Val Thr Ala Leu Ala Gln Arg Pro Pro Thr Asp Val Gly Gln Ala
225                 230                 235                 240

Glu Ala Thr Arg Lys Ala Ala Arg Met Val Trp Ala Asn Leu Leu Val
                245                 250                 255

Phe Val Val Cys Phe Leu Pro Leu His Val Gly Leu Thr Val Arg Leu
                260                 265                 270

Ala Val Gly Trp Asn Ala Cys Ala Leu Leu Glu Thr Ile Arg Arg Ala
        275                 280                 285

Leu Tyr Ile Thr Ser Lys Leu Ser Asp Ala Asn Cys Cys Leu Asp Ala
        290                 295                 300

Ile Cys Tyr Tyr Tyr Met Ala Lys Glu Phe Gln Glu Ala Ser Ala Leu
305                 310                 315                 320

Ala Val Ala Pro Ser Ala Lys Ala His Lys Ser Gln Asp Ser Leu Cys
                325                 330                 335

Val Thr Leu Ala
        340

<210> SEQ ID NO 9
<211> LENGTH: 236
<212> TYPE: DNA
<213> ORGANISM: Mus musculus

<400> SEQUENCE: 9
ctgccttctc actgctggga ttctacctgc cgctggccat cgtggtcttc tgctctttgc      60
aggtagtgac tgtgctatcg agaaggccag ccgctgatgt ggggcaggca gaggccaccc     120
aaaaggccac ccacatggtc tgggccaact ggctgtgtt tgtcatctgc ttcctgccct      180
tgcatgtggt cctgaccgtg caggtctccc tgaacctcaa tacctgtgct gcccga         236

<210> SEQ ID NO 10
<211> LENGTH: 24
<212> TYPE: DNA
<213> ORGANISM: Artificial
<220> FEATURE:
<223> OTHER INFORMATION: primer

<400> SEQUENCE: 10
ctgccttctc actgctggga ttct                                             24

<210> SEQ ID NO 11
<211> LENGTH: 24
<212> TYPE: DNA
<213> ORGANISM: Artificial
<220> FEATURE:

```
<223> OTHER INFORMATION: primer

<400> SEQUENCE: 11
tcgggcagca caggtattga ggtt                                        24

<210> SEQ ID NO 12
<211> LENGTH: 22
<212> TYPE: DNA
<213> ORGANISM: Artificial
<220> FEATURE:
<223> OTHER INFORMATION: primer

<400> SEQUENCE: 12
cacggggttc cacagaggta tg                                          22

<210> SEQ ID NO 13
<211> LENGTH: 21
<212> TYPE: DNA
<213> ORGANISM: Artificial
<220> FEATURE:
<223> OTHER INFORMATION: primer

<400> SEQUENCE: 13
caatggcaag gagcagagca g                                           21

<210> SEQ ID NO 14
<211> LENGTH: 23
<212> TYPE: DNA
<213> ORGANISM: Artificial
<220> FEATURE:
<223> OTHER INFORMATION: primer

<400> SEQUENCE: 14
ggggtgaggc cggtgctgag tat                                         23

<210> SEQ ID NO 15
<211> LENGTH: 24
<212> TYPE: DNA
<213> ORGANISM: Artificial
<220> FEATURE:
<223> OTHER INFORMATION: primer

<400> SEQUENCE: 15
cattgggggt aggaacacgg aagg                                        24

<210> SEQ ID NO 16
<211> LENGTH: 19
<212> TYPE: DNA
<213> ORGANISM: Artificial
<220> FEATURE:
<223> OTHER INFORMATION: primer

<400> SEQUENCE: 16
atgcaggagg gtggcttct                                              19

<210> SEQ ID NO 17
<211> LENGTH: 22
<212> TYPE: DNA
<213> ORGANISM: Artificial
<220> FEATURE:
<223> OTHER INFORMATION: primer

<400> SEQUENCE: 17
agaaggcagt ggtgctgaaa tt                                          22

<210> SEQ ID NO 18
```

```
<211> LENGTH: 22
<212> TYPE: DNA
<213> ORGANISM: Artificial
<220> FEATURE:
<223> OTHER INFORMATION: primer

<400> SEQUENCE: 18
ccttcagcag ccaaacccgg cg                                              22

<210> SEQ ID NO 19
<211> LENGTH: 19
<212> TYPE: DNA
<213> ORGANISM: Artificial
<220> FEATURE:
<223> OTHER INFORMATION: primer

<400> SEQUENCE: 19
tcctggcctc actgtccac                                                  19

<210> SEQ ID NO 20
<211> LENGTH: 19
<212> TYPE: DNA
<213> ORGANISM: Artificial
<220> FEATURE:
<223> OTHER INFORMATION: primer

<400> SEQUENCE: 20
gggccggact catcgtact                                                  19

<210> SEQ ID NO 21
<211> LENGTH: 26
<212> TYPE: DNA
<213> ORGANISM: Artificial
<220> FEATURE:
<223> OTHER INFORMATION: primer

<400> SEQUENCE: 21
ctgcttgctg atccacatct gctgga                                          26

<210> SEQ ID NO 22
<211> LENGTH: 18
<212> TYPE: PRT
<213> ORGANISM: Artificial
<220> FEATURE:
<223> OTHER INFORMATION: peptide

<400> SEQUENCE: 22

Arg Pro Pro Thr Asp Val Gly Gln Ala Glu Ala Thr Arg Lys Ala Ala
1               5                   10                  15
Arg Cys

<210> SEQ ID NO 23
<211> LENGTH: 19
<212> TYPE: DNA
<213> ORGANISM: Artificial
<220> FEATURE:
<223> OTHER INFORMATION: primer

<400> SEQUENCE: 23
atgcaggagg gtggcttct                                                  19

<210> SEQ ID NO 24
<211> LENGTH: 22
<212> TYPE: DNA
<213> ORGANISM: Artificial
<220> FEATURE:
<223> OTHER INFORMATION: primer
```

```
<400> SEQUENCE: 24
agaaggcagt ggtgctgaaa tt                                          22

<210> SEQ ID NO 25
<211> LENGTH: 21
<212> TYPE: DNA
<213> ORGANISM: Artificial
<220> FEATURE:
<223> OTHER INFORMATION: primer

<400> SEQUENCE: 25
cttcagcagc caaacccggc g                                           21

<210> SEQ ID NO 26
<211> LENGTH: 6
<212> TYPE: PRT
<213> ORGANISM: Artificial
<220> FEATURE:
<223> OTHER INFORMATION: peptide

<400> SEQUENCE: 26

Thr Leu Glu Ser Ile Met
1               5

<210> SEQ ID NO 27
<211> LENGTH: 5
<212> TYPE: PRT
<213> ORGANISM: Artificial
<220> FEATURE:
<223> OTHER INFORMATION: peptide

<400> SEQUENCE: 27

Glu Tyr Asn Leu Val
1               5

<210> SEQ ID NO 28
<211> LENGTH: 5
<212> TYPE: PRT
<213> ORGANISM: Artificial
<220> FEATURE:
<223> OTHER INFORMATION: peptide

<400> SEQUENCE: 28

Asp Cys Gly Leu Phe
1               5

<210> SEQ ID NO 29
<211> LENGTH: 36
<212> TYPE: DNA
<213> ORGANISM: Artificial
<220> FEATURE:
<223> OTHER INFORMATION: primer

<400> SEQUENCE: 29
gatcaagctt ccatggcgtg ctgcctgagc gaggag                           36

<210> SEQ ID NO 30
<211> LENGTH: 53
<212> TYPE: DNA
<213> ORGANISM: Artificial
<220> FEATURE:
<223> OTHER INFORMATION: primer

<400> SEQUENCE: 30
gatcggatcc ttagaacagg ccgcagtcct tcaggttcag ctgcaggatg gtg        53
```

METHOD OF USING GPR35 TO IDENTIFY METABOLIC-STABILIZING COMPOUNDS

This application is a continuation-in-part of U.S. patent application Ser. No. 11/596,035, filed on Nov. 8, 2006, now abandoned, which is a National Stage Entry of PCT/US2005/18082, filed on May 23, 2005, which claims the benefit of priority from the following provisional applications, filed via U.S. Express mail with the United States Patent and Trademark Office on the indicated dates: U.S. Provisional No. 60/574,849, filed May 26, 2004; U.S. Provisional No. 60/585,156, filed Jul. 1, 2004; U.S. Provisional No. 60/612,862, filed Sep. 24, 2004; U.S. Provisional No. 60/644,684, filed Jan. 18, 2005; and U.S. Provisional No. 60/647,969, filed Jan. 27, 2005.

FIELD OF THE INVENTION

The present invention relates to methods for identifying a metabolic stabilizing compound, for example, a compound that controls blood glucose levels and/or decreases free fatty acid levels in a subject, by determining whether a compound modulates GPR35 functionality. Accordingly, compounds of the present invention are useful in the prophylaxis or treatment of metabolic-related disorders such as diabetes, dyslipidemia, atherosclerosis, and obesity.

BACKGROUND OF THE INVENTION

Cells use glucose as a main source of energy. Therefore, food is first broken down by the body to glucose prior to being utilized. Glucose is then released from the gut into the blood resulting in a rise in blood glucose levels. In response to this rise in glucose level, pancreatic β-islet cells increase their production and secretion of insulin. Insulin circulates through the blood and acts as a messenger, sending a signal to insulin responsive organs such as the adipose tissue, muscle and liver, to increase their intake of glucose. In this way a rise in blood glucose is accompanied by a subsequent increase in insulin secretion from β-cells. It is the rise in insulin that acts to return blood glucose levels to normal. In healthy individuals blood glucose levels are kept fairly constant. This state of equilibrium, called normoglycemia (normal glucose level) is tightly controlled by insulin.

In diseases such as diabetes this tight regulation of blood glucose level is lost, leading to the increased blood glucose levels observed in diabetics. A state of hyperglycemia (high glucose level) can occur due to an insufficient production of insulin by the pancreatic β-cells and/or through inadequate uptake of glucose by target organs such as muscle, liver and fat. The end result is an increase in blood glucose level. Thus, diabetes can be thought of as the result of two types of impairment: impaired insulin secretion from the β-cells and impaired insulin sensitivity by the major insulin responsive organs. This impaired insulin sensitivity, also known as insulin resistance (because the organs are resistant to the effects of insulin), means that more insulin is required in order for the target organs to increase their glucose uptake. Insulin resistance leads to increased pressure on the β-cells because the β-cells need to increase their insulin secretion to compensate for insulin resistance. This is an escalating problem leading first to impaired glucose tolerance and; eventually, complete loss of insulin secretion due to the inability of the pancreas to keep up with the ever-increasing demand for insulin.

Diabetes is a diagnostic term for a group of disorders characterized by abnormal glucose homeostasis resulting in elevated blood glucose. There are many types of diabetes, but the two most common are Type I, also referred to as insulin-dependent diabetes mellitus or IDDM, and Type II, also referred to as non-insulin-dependent diabetes mellitus or NIDDM. Type I diabetes is mainly a disease with a young age of onset, and is due to the destruction of the insulin secreting β-cells in the pancreas by the immune system. In this case the body fails to recognize the pancreatic β-cells as being self and destroys its own cells. With the destruction of the β-cells there is a complete loss of insulin secretion and so affected individuals have an absolute dependency on insulin for survival. Type II diabetes is mainly a disease with a later age of onset, usually after the age of 40, but in recent years it is more common to find younger people being diagnosed with Type II diabetes. It is mainly characterized by insulin resistance and beta cell exhaustion and is often associated with obesity. Type II diabetes is more common than Type I diabetes and accounts for 90-95% of all diabetes cases diagnosed worldwide.

Chronic exposure of tissues to hyperglycemia can result in diverse complications including microvascular problems of neuropathy, retinopathy and nephropathy and the macrovascular complications of stroke, coronary heart disease, and peripheral vascular disease. Inappropriate control of blood glucose level is also a characteristic of diseases other than diabetes such as obesity, aging and Syndrome X. For example, one of the characteristics of Syndrome X is insulin resistance or glucose intolerance. In addition, obesity is characterized by hyperinsulinemia and insulin resistance, a feature shared with NIDDM, hypertension and atherosclerosis. Further, obesity is a major risk factor for NIDDM. The risk of developing NIDDM is tripled in subjects 30% or more overweight, and three-quarters of NIDDM patients are overweight.

Obesity, which is the result of an imbalance between caloric intake and energy expenditure, is highly correlated with insulin resistance and diabetes in experimental animals and humans. However, the molecular mechanisms that are involved in obesity-diabetes syndromes still under investigation. During early development of obesity, increased insulin secretion balances insulin resistance and protects patients from hyperglycemia (Le Stunff, et al., *Diabetes* 43:696-702 (1989)). However, over time, β cell function deteriorates and non-insulin-dependent diabetes develops in about 20% of obese individuals (Pederson, P., *Diab. Metab. Rev.* 5:505-509 (1989), and Brancati, F. L., et al., *Arch. Intern. Med.* 159:957-963 (1999)). Given its high prevalence in modern societies, obesity has thus become the leading risk factor for NIDDM (Hill, J. O., et al., *Science* 280:1371-1374 (1998)). However, the factors which predispose some patients to alteration of insulin secretion in response to fat accumulation remain unknown. Unfortunately, effective long-term therapies to treat obesity are still not available.

Diabetes afflicts several million people worldwide. In the United States alone, there are more than 18 million diabetics, with 600,000 new cases diagnosed each year. People with diabetes are at higher risk for heart disease, blindness, kidney failure, infection, extremity amputations, and other chronic conditions. It is estimated that the direct medical expenditures and indirect expenditures attributable to diabetes in the United States were $132 billion in 2002. Taken together, diabetes complications are one of the nation's leading causes of death.

Therapies do exist to treat diabetes, such as α-glucosidase inhibitors, biguanides, thiazolidinediones, meglitinides, sulfonylureas and exogenous insulin. However, these therapies have limited effectiveness and are associated with significant safety and tolerability issues such as risk for hypoglycemic episodes, weight gain, gastrointestinal disturbances and anemia. In addition, many of the treatment options require injection or multiple daily dosings which present compliance challenges.

Dyslipidemia is a general term for abnormal concentrations of blood lipids such as cholesterol, triglycerides and lipoproteins. Elevated levels of low density lipoprotein (LDL) cholesterol or low levels of high density lipoprotein (HDL) cholesterol are, independently, risk factors for atherosclerosis and associated cardiovascular pathologies. In addition, high levels of plasma free fatty acids are associated with insulin resistance and type 2 diabetes. One strategy for decreasing LDL-cholesterol, increasing HDL-cholesterol, and decreasing plasma free fatty acids is to inhibit lipolysis in adipose tissue. This approach involves regulation of hormone sensitive lipase, which is the rate-limiting enzyme in lipolysis. Lipolytic agents increase cellular levels of cAMP, which leads to activation of hormone sensitive lipase within adipocytes. Agents that lower intracellular cAMP levels, by contrast, would be antilipolytic.

Nicotinic acid (niacin, pyridine-3-carboxylic acid) is a water-soluble vitamin required by the human body for health, growth and reproduction; a part of the Vitamin B complex. Nicotinic acid is also one of the oldest used drugs for the treatment of dyslipidemia. It is a valuable drug in that it favorably affects virtually all of the lipid parameters listed above [Goodman and Gilman's Pharmacological Basis of Therapeutics, editors Harmon J G and Limbird L E, Chapter 36, Mahley R W and Bersot T P (2001): 971-1002]. The benefits of nicotinic acid in the treatment or prevention of atherosclerotic cardiovascular disease have been documented in six major clinical trials [Guyton J R (1998) Am J Cardiol 82:18U-23U]. Structure and synthesis of analogs or derivatives of nicotinic acid are discussed throughout the Merck Index, An Encyclopedia of Chemicals, Drugs, and Biologicals, Tenth Edition (1983).

Nicotinic acid and currently existing analogs thereof inhibit the production and release of free fatty acids from adipose tissue, likely via an inhibition of adenylyl cyclase, a decrease in intracellular cAMP levels, and a concomitant decrease in hormone sensitive lipase activity. Agonists that down-regulate hormone sensitive lipase activity leading to a decrease in plasma free fatty acid levels are likely to have therapeutic value. The consequence of decreasing plasma free fatty acids is two-fold. First, it will ultimately lower LDL-cholesterol and raise HDL-cholesterol levels, independent risk factors, thereby reducing the risk of mortality due to cardiovascular incidence subsequent to atheroma formation. Second, it will provide an increase in insulin sensitivity in individuals with insulin resistance or type 2 diabetes. Unfortunately, the use of nicotinic acid as a therapeutic is partially limited by a number of associated, adverse side-effects. These include flushing, free fatty acid rebound, and liver toxicity.

Agonists of antilipolytic GPCRs having limited tissue distribution beyond adipose may be especially valuable in view of the diminished opportunity for potentially undesirable side-effects.

Thus, there exists a need for the identification of an agent which safely and effectively controls blood glucose levels and/or free fatty acid levels for the treatment of metabolic-related disorders such as diabetes, dyslipidemia, atherosclerosis and obesity. The present invention satisfies this need and provides related advantages as well.

SUMMARY OF THE INVENTION

Applicants have determined the G-protein coupling of the orphan GPCR GPR35. In addition, Applicants have determined the tissue distribution pattern of GPR35 in humans, wild-type mice and mice with metabolic dysregulations.

In a first aspect, the invention features a method for identifying a metabolic stabilizing compound, comprising: a) contacting a candidate compound with GPR35, and b) determining whether GPR35 functionality is increased, wherein an increase in GPR35 functionality is indicative of the candidate compound being a metabolic stabilizing compound. In some embodiments, said GPR35 is human. In some embodiments, said determining comprises a second messenger assay.

In a second aspect, the invention features a metabolic stabilizing compound identified according to a method of the first aspect. In some embodiments, said metabolic stabilizing compound is a GPR35 agonist.

In a third aspect, the invention features a method for increasing GPR35 function in a cell, comprising contacting a cell expressing GPR35 with an effective amount of the metabolic stabilizing compound of the second aspect.

In a fourth aspect, the invention features a method for preparing a composition which comprises identifying a metabolic stabilizing compound and then admixing said compound with a pharmaceutically acceptable carrier, wherein said compound is identified by a method of the first aspect.

In a fifth aspect, the invention features a pharmaceutical composition comprising, consisting essentially of, or consisting of a compound of the second aspect and a pharmaceutically acceptable carrier.

In a sixth aspect, the invention features a method for treating or preventing a metabolic-related disorder in an individual in need thereof, comprising administering to said individual an effective amount of a compound of the second aspect or a pharmaceutical composition of the fifth aspect. In some embodiments, said metabolic-related disorder is diabetes, Type I diabetes, Type II diabetes, inadequate glucose tolerance, insulin resistance, hyperglycemia, hyperinsulinemia, hyperlipidemia, hypertriglyceridemia, hypercholesterolemia, dyslipidemia, obesity, aging, Syndrome X, atherosclerosis, heart disease, stroke, hypertension, or peripheral vascular disease. In some embodiments, said metabolic-related disorder is Type II diabetes. In some embodiments, said metabolic-related disorder is dyslipidemia. In some embodiments, a method of the sixth aspect comprises administering to said individual an effective amount of an agent used for the treatment of diabetes, blood lipid disorders, or obesity in combination with an effective amount of a compound of the second aspect or a pharmaceutical composition of the fifth aspect. In some embodiments, the individual is a mammal and in some embodiments the individual is a human.

In a seventh aspect, the invention features a method for decreasing blood glucose levels in an individual in need thereof, comprising administering to said individual an effective amount of a compound of the second aspect or a pharmaceutical composition of the fifth aspect. In some embodiments, a method of the seventh aspect comprises administering to said individual an effective amount of an agent used for the treatment of diabetes, blood lipid disorders, or obesity in combination with an effective amount of a compound of the second aspect or a pharmaceutical composition of the fifth aspect. In some embodiments, the individual is a mammal and in some embodiments the individual is a human.

In an eighth aspect, the invention features a method for decreasing free fatty acid levels in an individual in need thereof, comprising administering to said individual an effective amount of a compound of the second aspect or a pharmaceutical composition of the fifth aspect. In some embodiments, a method of the eighth aspect comprises administering to said individual an effective amount of an agent used for the treatment of diabetes, blood lipid disorders, or obesity in combination with a compound of the second aspect or a pharmaceutical composition of the fifth aspect. In some embodiments, the individual is a mammal and in some embodiments the individual is a human.

In a ninth aspect, the invention features a method for treating or preventing a metabolic-related disorder, comprising administering to an individual in need thereof an effective amount of a GPR35 modulator. In some embodiments said modulator is an agonist. In some embodiments, said metabolic-related disorder is diabetes, Type I diabetes, Type II diabetes, inadequate glucose tolerance, insulin resistance, hyperglycemia, hyperinsulinemia, hyperlipidemia, hypertriglyceridemia, hypercholesterolemia, dyslipidemia, obesity, aging, Syndrome X, atherosclerosis, heart disease, stroke, hypertension, or peripheral vascular disease. In some embodiments, said metabolic-related disorder is Type II diabetes. In some embodiments, said metabolic-related disorder is dyslipidemia. In some embodiments, a method of the ninth aspect comprises administering to said individual an effective amount of an agent used for the treatment of diabetes, blood lipid disorders, or obesity in combination with an effective amount of the compound of the invention. In some embodiments, the individual is a mammal and in some embodiments the individual is a human.

In a tenth aspect, the invention features a method for decreasing blood glucose levels in an individual in need thereof, comprising administering to the individual an effective amount of a GPR35 modulator. In some embodiments, said modulator is an agonist. In some embodiments the individual is a mammal. In some embodiments the mammal is a human.

In an eleventh aspect, the invention features a method for decreasing free fatty acid levels in an individual in need thereof, comprising administering to the individual an effective amount of a GPR35 modulator. In some embodiments, said modulator is an agonist. In some embodiments the individual is a mammal. In some embodiments the mammal is a human.

DETAILED DESCRIPTION

Figure 1:
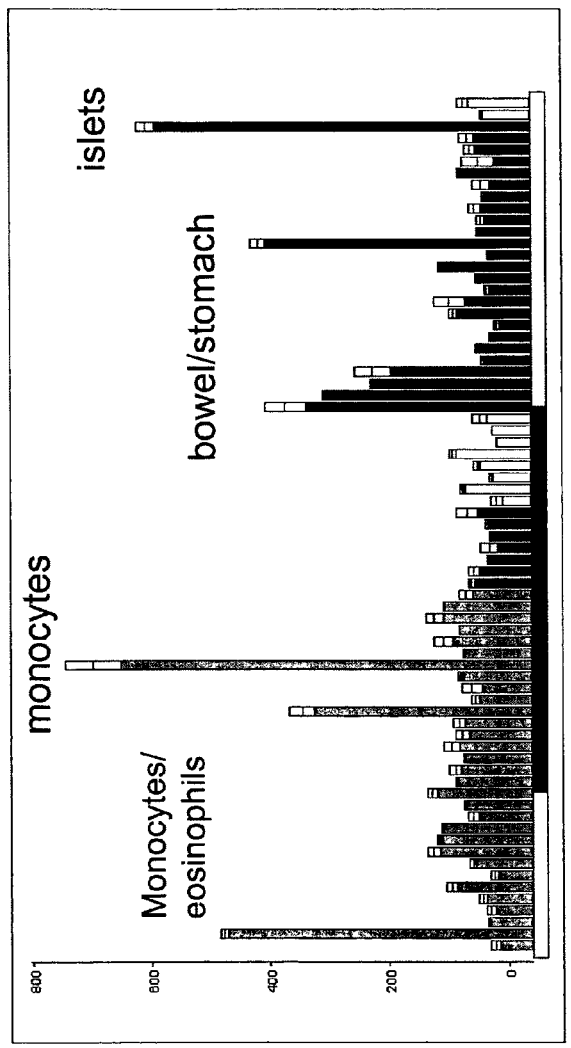
FIG. 1 shows Affymetrix gene chip analysis of human GPR35 expression in human cell types and tissues. The cell or tissues from left to right are: Jurkat; monocytes (adherent); SHSH5Y; U87; SHSH5Y (+BDNF); THP-1; MCF7; HL-60 (+DMSO); THP-1 activated; T-cells CD8+ resting; T-cells CD8+ activated; CD34+ progenitor cells; T-cells CD4+ activated T-cells CD4+ resting; spleen; bone marrow; B-cells CD19+; thymus; lymph node; neutrophils BM (n=1); eosinophils; AC133+; neutrophils; natural killer cells; monocytes CD14+; erythroid progenitors; CD34+MPB; myeloid prog. MPB; myeloid prog. BM; dendritic precursors; CD34+CB; ventricle, left; cartilage; adipocyte, cultured; preadipocyte, cultured; visceral fat; adipocyte, primary; adipose; aortic smooth muscle cells, c, aortic valve, HUVEC, aorta, heart, aortic smooth muscle cells, p; aortic endothelial cells; pericardium; small intestine, colon; rectum; stomach; fetal liver; liver; fibroblast, dermal; keratinocyte; kidney; pancreas; esophagus; adrenal gland; gall bladder; mesenchymal stem cell; duodenum; skin; melanocytes; trachea; skeletal muscle; bone; bladder; salivary gland; smooth muscle; lung; pancreatic islets; breast; ovary.
Figure 2:
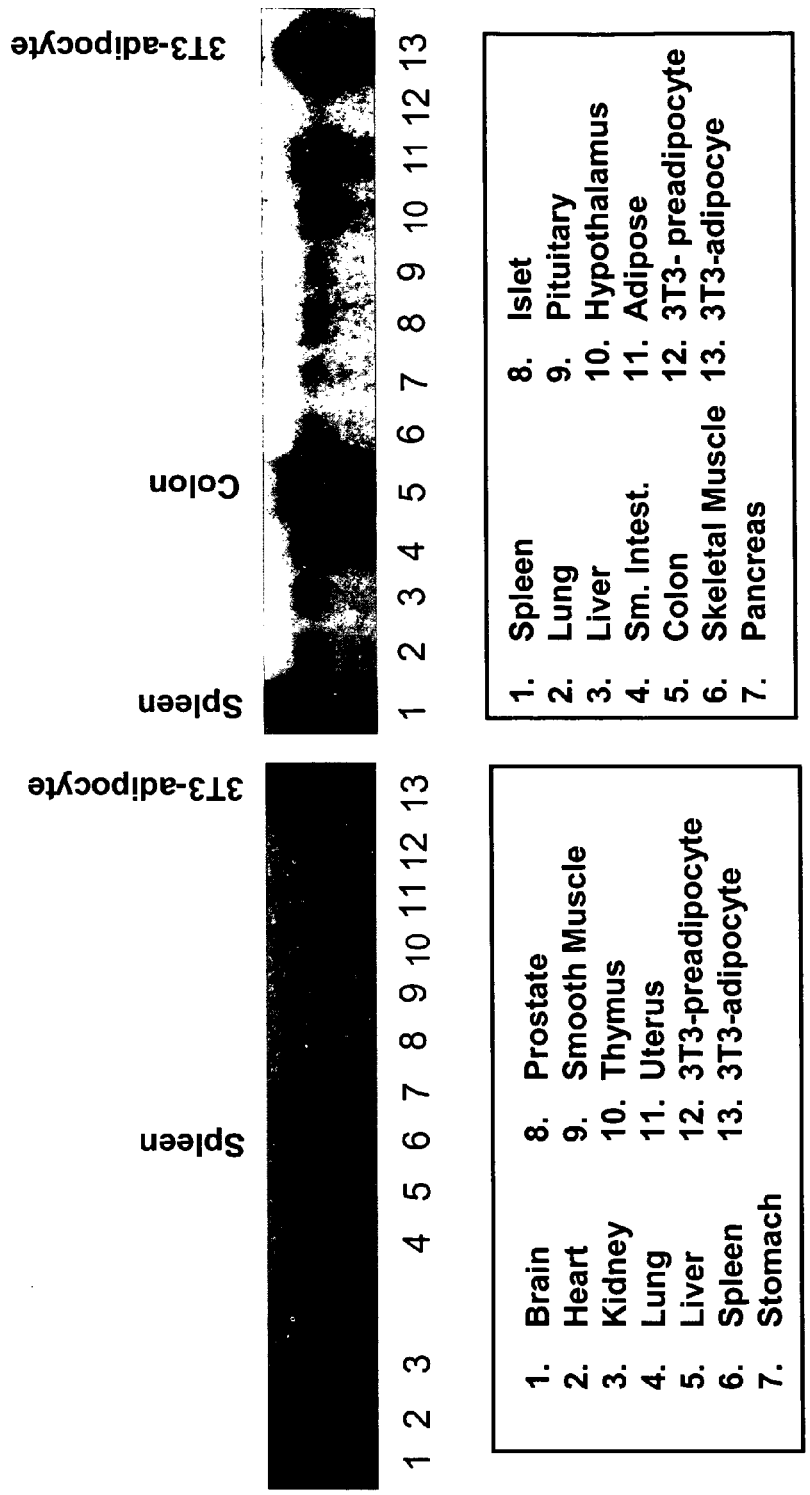
FIG. 2 shows RNase protection assay analysis of mouse GPR35 expression in mouse cell types and tissues.

Applicants have disclosed herein that human GPR35 is expressed prominently in pancreatic islet cells, monocytes, and bowel/stomach (see FIG. 1) and mouse GPR35 is expressed at highest levels in colon, adipocytes and spleen (see FIG. 2). In addition, Applicants have disclosed herein the G-protein coupling of the orphan GPCR GPR35 to G-alpha i and G-alpha 12/13 (see FIG. 3). Further, Applicants disclose herein that GPR35 is induced in the liver, adipose and pancreas of db/db mutant mice (see FIGS. 4 and 5). In addition, Applicants disclose differential expression of GPR35 in the pancreata of db/db mice compared to ob/ob mice (see FIG. 6). Applicants have generated cells which express human GPR35 and a polyclonal antibody to human GPR35 (see FIG. 7). In addition, Applicants disclose herein that mouse GPR35 is induced after linoleic acid treatment of 3T3-L1 adipocytes (see FIG. 8).

Although a number of receptor classes exist in humans, by far the most abundant and therapeutically relevant is represented by the G protein-coupled receptor (GPCR) class. It is estimated that there are some 30,000-40,000 genes within the human genome, and of these, approximately 2% are estimated to code for GPCRs. GPCRs represent an important area for the development of pharmaceutical products: from approximately 20 of the 100 known GPCRs, approximately 60% of all prescription pharmaceuticals have been developed.

GPCRs share a common structural motif, having seven sequences of between 22 to 24 hydrophobic amino acids that form seven alpha helices, each of which spans the membrane (each span is identified by number, i.e., transmembrane-1 (TM-1), transmembrane-2 (TM-2), etc.). The transmembrane helices are joined by strands of amino acids between transmembrane-2 and transmembrane-3, transmembrane-4 and transmembrane-5, and transmembrane-6 and transmembrane-7 on the exterior, or "extracellular" side, of the cell membrane (these are referred to as "extracellular" regions 1, 2 and 3 (EC-1, EC-2 and EC-3), respectively). The transmembrane helices are also joined by strands of amino acids between transmembrane-1 and transmembrane-2, transmembrane-3 and transmembrane-4, and transmembrane-5 and transmembrane-6 on the interior, or "intracellular" side, of the cell membrane (these are referred to as "intracellular" regions 1, 2 and 3 (IC-1, IC-2 and IC-3), respectively). The "carboxy" ("C") terminus of the receptor lies in the intracellular space within the cell, and the "amino" ("N") terminus of the receptor lies in the extracellular space outside of the cell.

Generally, when a ligand binds with the receptor (often referred to as "activation" of the receptor); there is a change in the conformation of the receptor that facilitates coupling between the intracellular region and an intracellular "G-protein." It has been reported that GPCRs are "promiscuous" with respect to G proteins, i.e., that a GPCR can interact with more than one G protein. See, Kenakin, T., 43 Life Sciences 1095 (1988). Although other G proteins exist, currently, Gq, Gs, Gi, Gz and Go are G proteins that have been identified. Ligand-activated GPCR coupling with the G-protein initiates a signaling cascade process (referred to as "signal transduction"). Under normal conditions, signal transduction ultimately results in cellular activation or cellular inhibition. Although not wishing to be bound to theory, it is thought that the IC-3 loop as well as the carboxy terminus of the receptor interact with the G protein.

There are also promiscuous G proteins, which appear to couple several classes of GPCRs to the phospholipase C pathway, such as G$\alpha$15 or G$\alpha$16 (Offermanns & Simon, *J Biol Chem* 270:15175-80 (1995)), or chimeric G proteins designed to couple a large number of different GPCRs to the same pathway, e.g. phospholipase C (Milligan & Rees, *Trends in Pharmaceutical Sciences* 20:118-24 (1999)).

Gi-coupled GPCRs lower intracellular cAMP levels. The melanophore technology (see infra) is useful for identifying Gi-coupled GPCRs and also for identifying modulators of said Gi-coupled GPCRs.

Under physiological conditions, GPCRs exist in the cell membrane in equilibrium between two different conformations: an "inactive" state and an "active" state. A receptor in an inactive state is unable to link to the intracellular signaling transduction pathway to initiate signal transduction leading to a biological response. Changing the receptor conformation to the active state allows linkage to the transduction pathway (via the G-protein) and produces a biological response.

A receptor can be stabilized in an active state by a ligand or a compound such as a drug. Recent discoveries, including but not exclusively limited to modifications to the amino acid sequence of the receptor, provide means other than ligands or drugs to promote and stabilize the receptor in the active state conformation. These means effectively stabilize the receptor in an active state by simulating the effect of a ligand binding to the receptor. Stabilization by such ligand-independent means is termed "constitutive receptor activation."

GPR35 was first cloned by O'Dowd et al. (O'Dowd, B. F. et al., *Genomics* 47:310-313 (1998)). O'Dowd et al. searched for genes related to GPR1 using PCR of genomic DNA with degenerate primers based on conserved transmembrane regions of GPR1. Among other genes, they identified the GPR35 gene, which contained a single exon that encodes a predicted 309-amino acid protein. In addition, O'Dowd et al. mapped the GPR35 gene to 2q37.3 by fluorescence in situ hybridization.

Horikawa et al. (Horikawa, Y. et al., *Nature Genet.* 26:163-175 (2000)) identified the GPR35 gene in a 66-kb interval on chromosome 2 that showed linkage to noninsulin-dependent diabetes mellitus. However, they showed single-nucleotide polymorphisms (SNPs) in GPR35 did not show association with or linkage to type 2 diabetes. Instead, they disclose that SNPs in the calpain gene are associated with diabetes. In addition, they detected GPR35 expression in all fetal and adult human tissues examined, with relatively higher levels in adult lung, small intestine, colon, and stomach.

Recently, Okumura et al. found GPR35, and an alternatively spliced form of GPR35 which contains 31 amino acids at the N-terminus of GPR35, expressed in gastric cancers (Okumura et al., *Cancer Sci.* 95:131-135 (2004)). The alternatively spliced form of GPR35 has been designated GPR35b.

DEFINITIONS

The scientific literature that has evolved around receptors has adopted a number of terms to refer to ligands having various effects on receptors. For clarity and consistency, the following definitions will be used throughout this patent document.

AGONIST shall mean material, for example, a ligand or candidate compound, that activates an intracellular response when it binds to the receptor. An intracellular response can be, for example, enhancement of GTP binding to membranes or modulation of the level of a second messenger such as cAMP or IP3. In some embodiments, an AGONIST is material not previously known to activate the intracellular response when it binds to the receptor (for example, to enhance GTP$\gamma$S binding to membranes or to lower intracellular cAMP level). In some embodiments, an AGONIST is material not previously known to decrease blood glucose level when it binds to the receptor. The term AGONIST also includes PARTIAL AGONISTS which are materials, for example, ligands or candidate compounds, which activate the intracellular response when they bind to the receptor to a lesser degree or extent than do full agonists.

ANTAGONIST shall mean material, for example, ligands or candidate compounds that competitively bind to the receptor at the same site as an agonist but which does not activate an intracellular response, and can thereby inhibit an intracellular response elicited by the agonist. An ANTAGONIST does not diminish the baseline intracellular response in the absence of an agonist. In some embodiments, an ANTAGONIST is material not previously known to compete with an agonist to inhibit a cellular response when it binds to the receptor (for example, wherein the cellular response is GTP$\gamma$S binding to membranes or to the lowering of intracellular cAMP level).

ANTIBODY is intended herein to encompass monoclonal antibodies and polyclonal antibodies. The term ANTIBODY is further intended to encompass IgG, IgA, IgD, IgE, and IgM. Antibodies include whole antibodies, including single-chain whole antibodies, and antigen binding fragments thereof, including Fab, Fab', F(ab)2 and F(ab')2. Antibodies can be from any natural or synthetic origin, for example, from human, murine, rabbit, goat, guinea pig, hamster, camel, donkey, sheep, horse or chicken. Antibodies can have binding affinities with a dissociation constant or Kd value, for example, less than $5\times10^{-6}$M, $10^{-6}$M, $5\times10^{-7}$M, $10^{-7}$M, $5\times10^{-8}$M, $10^{-8}$M, $5\times10^{-9}$M, $10^{-9}$M, $5\times10^{-10}$M $10^{-10}$M, $5\times10^{-11}$M, $10^{-11}$M, $5\times10^{-12}$M, $10^{-12}$M, $5\times10^{-13}$M, $10^{-13}$M, $5\times10^{-14}$M $10^{-14}$M, $5\times10^{-15}$M and $10^{-15}$M. Antibodies of the present invention can be prepared by any suitable method known in the art.

CANDIDATE COMPOUND shall mean a molecule (for example, a chemical compound) that is amenable to a screening technique. Applicants are not aware of any compound being publicly known to bind to or interact with GPR35, however if any such compound is known, the phrase "candidate compound" would specifically exclude such a compound.

COMPOSITION shall mean a material comprising at least two compounds or two components; for example, a "Pharmaceutical Composition" is a Composition.

COMPOUND EFFICACY shall mean a measurement of the ability of a compound to inhibit or stimulate receptor functionality, as opposed to receptor binding affinity.

CONSTITUTIVELY ACTIVATED RECEPTOR shall mean a receptor subject to constitutive receptor activation.

CONSTITUTIVE RECEPTOR ACTIVATION shall mean stabilization of a receptor in the active state by means other than binding of the receptor with its endogenous ligand or a chemical equivalent thereof.

CONTACT or CONTACTING shall mean bringing at least two moieties together, whether in an in vitro system or an in vivo system.

DIABETES as used herein is intended to encompass the usual diagnosis of diabetes made from any method including, for example, the following list: symptoms of diabetes (e.g., polyuria, polydipsia, polyphagia) plus casual blood glucose levels of greater than or equal to 200 mg/dl, wherein casual blood glucose is defined any time of the day regardless of the timing of meal or drink consumption; or 8 hour fasting blood glucose levels of greater than or equal to 126 mg/dl; or blood glucose levels of greater than or equal to 200 mg/dl two hours following oral administration of 75 g anhydrous glucose dissolved in water. In addition, the term diabetes as used herein also includes the "pre-diabetic" state as defined by the American Diabetes Association to be a fasting blood glucose level of 100-125 mg/dl or blood glucose levels of 140-199 mg/dl two hours following oral administration of glucose.

DYSLIPIDEMIA as used herein is a general term for abnormal concentrations of blood lipids such as cholesterol, triglycerides and lipoproteins. For example, an individual with dyslipidemia can have a high level of total cholesterol compared with the optimum level (hypercholesterolemia). In addition, for example, an individual with dyslipidemia can have a high level of a blood lipid such as low-density lipoprotein (LDL) or triglycerides (hypertriglyceridemia). Further, for example, an individual with dyslipidemia can have a low level of a blood lipid such as high-density lipoprotein (HDL). An individual with dyslipidemia can have alterations in the level of one or more serum lipids such as, for example, total cholesterol, LDL, triglycerides, or HDL. Dyslipidemia is a blood lipid disorder.

ENDOGENOUS shall mean a material that a mammal naturally produces. ENDOGENOUS in reference to, for example and not limitation, the term "receptor" shall mean that which is naturally produced by a mammal (for example, and not limitation, a human) or a virus. In contrast, the term NON-ENDOGENOUS in this context shall mean that which is not naturally produced by a mammal (for example, and not limitation, a human) or a virus. For example, and not limitation, a receptor which is not constitutively active in its endogenous form, but when manipulated becomes constitutively active, is most preferably referred to herein as a "non-endogenous, constitutively activated receptor." Both terms can be utilized to describe both "in vivo" and "in vitro" systems. For example, and not a limitation, in a screening approach, the endogenous or non-endogenous receptor can be in reference to an in vitro screening system.

EFFECTIVE AMOUNT means an amount of active compound or pharmaceutical composition that elicits the desired biological or medicinal response in a tissue, system, or individual that is being sought by the researcher or medical doctor or other clinician. For example, an effective dose can be an amount that can treat a metabolic-related disorder. Also, for example, an effective dose can be an amount that can prevent a metabolic-related disorder.

INHIBIT or INHIBITING, in relationship to the term "response" shall mean that a response is decreased or prevented in the presence of a compound as opposed to in the absence of the compound.

IN NEED OF PREVENTION OR TREATMENT as used herein refers to a judgment made by a caregiver (e.g. physician, nurse, nurse practitioner, etc. in the case of humans; veterinarian in the case of animals, including non-human mammals) that an individual or animal requires or will benefit from treatment. This judgment is made based on a variety of factors that are in the realm of a caregiver's expertise, but include the knowledge that the individual or animal is ill, or will be ill, as the result of a condition that is treatable or preventable by a compound of the invention.

INDIVIDUAL as used herein refers to any animal, including mammals, preferably mice, rats, other rodents, rabbits, dogs, cats, swine, cattle, sheep, horses, or primates, and most preferably humans.

INSULIN RESISTANCE as used herein is intended to encompass the usual diagnosis of insulin resistance made by any of a number of methods, including but not restricted to: the intravenous glucose tolerance test or measurement of the fasting insulin level. It is well known that there is a good correlation between the height of the fasting insulin level and the degree of insulin resistance. Therefore, one could use elevated fasting insulin levels as a surrogate marker for insulin resistance for the purpose of identifying which normal glucose tolerance (NGT) individuals have insulin resistance. A diagnosis of insulin resistance can also be made using the euglycemic glucose clamp test.

LIGAND shall mean an endogenous, naturally occurring molecule specific for an endogenous, naturally occurring receptor.

As used herein, the terms MODULATE or MODULATING shall mean to refer to an increase or decrease in the amount, quality, response or effect of a particular activity, function or molecule. A GPR35 MODULATOR is an agent that modulates the GPR35 receptor.

METABOLIC-RELATED DISORDER means a disorder of metabolism. As used herein a metabolic-related disorder is intended herein to include, for example, diabetes including Type I diabetes and Type II diabetes, inadequate glucose tolerance, insulin resistance, hyperglycemia, hyperinsulinemia, hyperlipidemia, hypertriglyceridemia, hypercholesterolemia, dyslipidemia, obesity, aging and Syndrome X. In addition, the term metabolic-related disorder is intended to include diseases that can result from diseases such as hyperglycemia or dyslipidemia, for example, atherosclerosis, heart disease, stroke, hypertension and peripheral vascular disease.

METABOLIC-STABILIZING COMPOUND is intended to mean a compound that stabilizes a metabolic parameter. Metabolic parameters include any measure of metabolism such as the level of lipids, sugars, enzymes or other proteins in response to metabolic processes. For example, a metabolic-stabilizing compound can decrease (stabilize) blood glucose levels in an individual or a metabolic-stabilizing compound can decrease (stabilize) free fatty acid levels in an individual. In addition, for example, a metabolic-stabilizing compound can decrease blood glucose levels and decrease free fatty acid levels in an individual.

PHARMACEUTICAL COMPOSITION shall mean a composition comprising at least one compound and a pharmaceutically acceptable carrier. For example, a pharmaceutical composition can comprise at least one active ingredient, whereby the composition is amenable to investigation for a specified, efficacious outcome in an animal (for example, a mammal such as a human). Those of ordinary skill in the art will understand and appreciate the techniques appropriate for determining whether an active ingredient has a desired efficacious outcome based upon the needs of the artisan.

RECEPTOR FUNCTIONALITY shall refer to the normal operation of a receptor to receive a stimulus and moderate an effect in the cell, including, but not limited to regulating gene transcription, regulating the influx or efflux of ions, effecting a catalytic reaction, and/or modulating activity through G-proteins. A GPR35 functionality can be, for example, binding a G-protein such as Gi or G12/13, signaling through a second messenger such as cAMP or IP3 (when using a chimeric G-protein), binding to a GPR35 antibody, or lowering blood glucose levels in vivo.

SECOND MESSENGER shall mean an intracellular response produced as a result of receptor activation. A second messenger can include, for example, inositol triphosphate (IP3), diacylglycerol (DAG), cyclic AMP (cAMP), cyclic GMP (cGMP), and Ca2+. Second messenger response can be measured for a determination of receptor activation. In addition, second messenger response can be measured for the direct identification of candidate compounds, including for example, inverse agonists, partial agonists, agonists, and antagonists.

The sequence of human GPR35 as published by O'Dowd et al. (supra, 1998) was deposited in GenBank as Accession No. AF027957 (SEQ ID NO:1). The O'Dowd sequence encodes an arginine at position 174 and an arginine at position 294 (see SEQ ID NO:2). Another human GPR35 sequence is the genomic sequence for GPR35 which is GenBank Accession No. AF158748. The genomic sequence (nucleotides 60183-61112) (SEQ ID NO:3) encodes an alanine at position 174 and a serine at position 294 (see SEQ ID NO:4). Different sequences for GPR35 can be the result of allelic variations in the population. Thus, the definition of the term GPR35 as used herein includes both of these sequences as well as allelic variants.

The invention provides an antibody, or antigen binding fragment thereof, which specifically binds to a GPR35 polypeptide, for example, comprising an amino acid sequence encoded by GenBank as Accession No. AF027957 (SEQ ID NO:2) or GenBank Accession No. AF158748 (nucleotides 60183-61112) (SEQ ID NO:4). The term "specifically binds" is intended to mean the polypeptide will have an affinity for a target polypeptide that is measurably higher than its affinity for an unrelated polypeptide. An antibody can specifically bind to GPR35 with low or high affinity so long as the binding is sufficient to be detectable. For example, an antibody can bind GPR35 with a binding affinity (Kd) of at least $10^{-4}$, $10^{-5}$, $10^{-6}$, $10^{-7}$, $10^{-8}$, $10^{-9}$ or $10^{-10}$. Several methods for detecting or measuring antibody binding to an antigen are well known in the art, for example, enzyme linked immunosorbent assays (ELISA). An antibody which specifically binds to a GPR35 polypeptide is disclosed herein in Example 7 and FIG. 7.

An antibody as used herein includes naturally occurring antibodies as well as non-naturally occurring antibodies, including, for example, single chain antibodies, chimeric, bifunctional and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting of variable heavy chains and variable light chains as described by Huse et al. (*Science* 246:1275-1281 (1989)). These and other methods of making, for example, chimeric, humanized, CDR-grafted, single chain, and bifunctional antibodies are well known to those skilled in the art (Winter and Harris, *Immunol. Today* 14:243-246 (1993); Ward et al., *Nature* 341:544-546 (1989); Harlow and Lane, (1988); Hilyard et al., Protein Engineering: A practical approach (IRL Press 1992); Borrabeck, Antibody Engineering, 2d ed. (Oxford University Press 1995)).

An antibody of the invention can be labeled, for example, with a fluorescent, radioactive or enzyme label. Procedures for conjugating an antibody or antibody fragment to a label are well known in the art. Such labeled antibodies can be used a diagnostics to identify GPR35 expression in a biologic sample such as a cell, blood, tissue slice, or in an individual in vivo. In addition to being conjugated to a diagnostic label, antibodies can also be conjugated to therapeutic labels, for example, in order to deliver a compound to a cell expressing the antigen. Antibody therapeutics are well known in the art, for example, antibodies conjugated to cytotoxic agents have been used to target the cytotoxic agent to cancer cells.

The invention relates to a method for identifying a metabolic stabilizing compound, comprising: a) contacting a candidate compound with GPR35, and b) determining whether GPR35 functionality is modulated, wherein a modulation in GPR35 functionality is indicative of the candidate compound being a metabolic stabilizing compound. For example, the invention provides a method for identifying a metabolic stabilizing compound, comprising: a) contacting a candidate compound with GPR35, and b) determining whether GPR35 functionality is increased, wherein an increase in GPR35 functionality is indicative of the candidate compound being a metabolic stabilizing compound.

As used herein, "GPR35" refers to a polypeptide with the amino acid sequence as encoded by GenBank Accession No. AF027957 (SEQ ID NO:2), or the analogous sequence in GenBank Accession No. AF158748 (nucleotides 60183-61112) (SEQ ID NO:4), or a variant or ortholog of these sequences that retains at least one function of a polypeptide with the amino acid sequence as referenced in SEQ ID NO:2 or SEQ ID NO:4.

It is understood that limited variations or modifications to GPR35 can be made without destroying its function. For example, GPR35 is intended to include other GPR35 polypeptides, for example, mammalian species orthologs of the human GPR35 polypeptide. The sequences of species orthologs of human GPR35 are present in the database, for example, a mouse ortholog of GPR35 can be found in GenBank at Accession No. BC027429 (see SEQ ID NOS:5,6). In addition, GPR35 includes variants such as allelic variants, splice variants and conservative amino acid substitution variants of GPR35. For example, GPR35 includes variants that retain substantially a GPR35 function of the entire GPR35 polypeptide such as, for example, the ability to signal through G-alpha i or G-alpha 12/13, the ability to specifically bind to a GPR35 antibody, or the ability to regulate blood glucose or free fatty acid levels.

Conservative and non-conservative amino acid changes, gaps, and insertions to an amino acid sequence can be compared to a reference sequence using available algorithms and programs such as the Basic Local Alignment Search Tool ("BLAST") using default settings [See, e.g., Karlin and Altschul, Proc Natl Acad Sci USA (1990) 87:2264-8; Altschul et al., J Mol Biol (1990) 215:403-410; Altschul et al., Nature Genetics (1993) 3:266-72; and Altschul et al., Nucleic Acids Res (1997) 25:3389-3402].

A splice variant of GPR35 has been reported which contains additional amino-terminal sequence (Okumura et al., *Cancer Sci.* 95:131-135 (2004)). This splice variant has been designated GPR35b (see SEQ ID NOS:7,8).

It is understood that a fragment of GPR35 which retains substantially a function of the entire polypeptide is included in the definition. For example, a signal generating domain of GPR35 or a compound binding domain of GPR35 can be used in lieu of the entire polypeptide. In addition, GPR35 can contain heterologous sequences such as an epitope tag or other fused polypeptide. Further, GPR35 can contain a label, for example, a radiolabel, fluorescent label or enzymatic label.

In one embodiment, the methods of the invention can be applied using a polypeptide comprising 99%, 98%, 95%, 92%, 90%, 85%, 80%, 75%, or 70% sequence identity to one of the following sequences: SEQ ID NO:2, SEQ ID NO:4, SEQ ID NO:6, or SEQ ID NO:8.

In some embodiments, said variant of GPR35 is a non-endogenous, constitutively activated mutant of GPR35. In one embodiment, said GPR35 is derived from a mammal. In another embodiment, said GPR35 is human.

In certain embodiments, said GPR35 is recombinant. In certain embodiments, said contacting comprises contacting with a host cell or with membrane of a host cell that expresses the GPCR, wherein the host cell comprises an expression vector comprising a polynucleotide encoding the receptor.

The invention also relates to a method of identifying a candidate compound as a modulator of blood glucose concentration, comprising a) contacting a candidate compound with GPR35, and b) determining whether GPR35 functionality is modulated, wherein a modulation in GPR35 functionality is indicative of the candidate compound being a modulator of blood glucose concentration. For example, a compound that increases GPR35 functionality, such as a GPR35 agonist, can result in a decrease in blood glucose concentration. A decrease in blood glucose can be desired, for example, in individuals with hyperglycemia. A compound that decreases GPR35 functionality, such as a GPR35 antagonist or inverse agonist, can result in an increase in blood glucose concentration. An increase in blood glucose can be desired, for example, in individuals with hypoglycemia.

The invention also relates to a method of identifying a candidate compound as a modulator of free fatty acid concentration, comprising a) contacting a candidate compound with GPR35, and b) determining whether GPR35 functionality is modulated, wherein a modulation in GPR35 functionality is indicative of the candidate compound being a modulator of free fatty acid concentration. For example, a compound that increases GPR35 functionality, such as a GPR35 agonist, can result in a decrease in free fatty acid concentration. A decrease in free fatty acid concentration can be desired, for example, in individuals with dyslipidemia.

In certain embodiments, said GPR35 is recombinant. In certain embodiments, said contacting comprises contacting with a host cell or with membrane of a host cell that expresses the GPCR, wherein the host cell comprises an expression vector comprising a polynucleotide encoding the receptor.

In the methods of the invention, control reactions can be performed to show specificity of the response. For example, mock-transfected cells can be compared to GPR35 transfected cells to show specificity of a response to the GPR35 receptor.

In the methods of the invention, in certain embodiments, said candidate compound is not an antibody or antigen-binding derivative thereof. In certain embodiments, said candidate compound is not a peptide. In certain embodiments, said candidate compound is not a polypeptide.

As stated above, receptor functionality refers to the normal operation of a receptor to receive a stimulus and moderate an effect in the cell, including, but not limited to regulating gene transcription, regulating the influx or efflux of ions, effecting a catalytic reaction, and/or modulating activity through G-proteins. A GPR35 functionality can be, for example, binding a G-protein such as Gi or G12/13, signaling through a second messenger such as cAMP or IP3 (when using a chimeric G-protein), specifically binding to a GPR35 antibody, or lowering blood glucose or free fatty acid levels in vivo.

In one embodiment, said determining comprises a second messenger assay. The initiation of an intracellular signal can be determined, for example, through the measurement of the level of a second messenger such as cyclic AMP (cAMP), cyclic GMP (cGMP), inositol triphosphate (IP3), diacylglycerol (DAG), MAP kinase, or calcium. Several assays are well known in the art for measuring these second messengers, for example, cAMP assays, IP3 assays, the FLIPR assay, the melanophore assay, or CRE-reporter assay. In addition, examples of second messenger assays are disclosed herein in Examples 14-19. In certain embodiments, said second messenger is cAMP. In other embodiments, said second messenger is IP3. In further embodiments said second messenger is calcium.

In one embodiment, said determining is through the measurement of GTPγS binding to membrane comprising said GPCR. Such assays are well known in the art and exemplified herein in Examples 14 and 16. In certain embodiments, said GTPγS is labeled with [$^{35}$S].

The invention also relates to a metabolic stabilizing compound identifiable according to the method of: a) contacting a candidate compound with GPR35, and b) determining whether GPR35 functionality is increased, wherein an increase in GPR35 functionality is indicative of the candidate compound being a metabolic stabilizing compound.

For example, the invention provides a metabolic stabilizing compound identified according to the method of: a) contacting a candidate compound with GPR35, and b) determining whether GPR35 functionality is increased, wherein an increase in GPR35 functionality is indicative of the candidate compound being a metabolic stabilizing compound.

In one embodiment, said metabolic stabilizing compound is a GPR35 agonist. As described above, an agonist can also include, for example, a partial agonist.

In some embodiments, said metabolic stabilizing compound is an agonist with an EC50 of less than 10 µM, of less than 1 µM, of less than 100 nM, or of less than 10 nM. In some embodiments, said metabolic stabilizing compound is an agonist with an EC50 of a value selected from the interval of 1 nM to 10 µM. In some embodiments, said metabolic stabilizing compound is an agonist with an EC50 of a value selected from the interval of 1 nM to 1 µM. In some embodiments, said metabolic stabilizing compound is an agonist with an EC50 of a value selected from the interval of 1 nM to 100 nM. In some embodiments, said metabolic stabilizing compound is an agonist with an EC50 of a value selected from the interval of 1 nM to 10 nM.

In certain embodiments, said EC50 is determined using an assay selected from the group consisting of: IP3 assay carried out using transfected HEK293 cells expressing recombinant GPR35 polypeptide; and melanophore assay carried out using transfected melanophores expressing recombinant GPCR35 polypeptide. In some embodiments, said metabolic stabilizing compound is an agonist with an EC50 of less than 10 µM, of less than 1 µM, of less than 100 nM, or of less than 10 nM in said assay. In some embodiments, said metabolic stabilizing compound is an agonist with an EC50 of less than 10 µM in said assay. In some embodiments, said metabolic stabilizing compound is an agonist with an EC50 of less than 9 µM in said assay. In some embodiments, said metabolic stabilizing compound is an inverse agonist or antagonist with an EC50 of less than 8 µM in said assay. In some embodiments, said metabolic stabilizing compound is an agonist with an EC50 of less than 7 µM in said assay. In some embodiments, said metabolic stabilizing compound is an agonist with an EC50 of less than 6 µM in said assay. In some embodiments, said metabolic stabilizing compound is an agonist with an EC50 of less than 5 µM in said assay. In some embodiments, said metabolic stabilizing compound is an agonist with an EC50 of less than 4 µM in said assay. In some embodiments, said metabolic stabilizing compound is an agonist with an EC50 of less than 3 µM in said assay. In some embodiments, said metabolic stabilizing compound is an agonist with an EC50 of less than 2 µM in said assay. In some embodiments, said metabolic stabilizing compound is an agonist with an EC50 of less than 1 µM in said assay. In some embodiments, said metabolic stabilizing compound is an agonist with an EC50 of less than 900 nM in said assay. In some embodiments, said metabolic stabilizing compound is an agonist with an EC50 of less than 800 nM in said assay. In some embodiments, said metabolic stabilizing compound is an agonist with an EC50 of less than 700 nM in said assay. In some embodiments, said metabolic stabilizing compound is an agonist with an EC50 of less than 600 nM in said assay. In some embodiments, said metabolic stabilizing compound is an agonist with an EC50 of less than 500 nM in said assay. In some embodiments, said metabolic stabilizing compound is an agonist with an EC50 of less than 400 nM in said assay. In some embodiments, said metabolic stabilizing compound is an agonist with an EC50 of less than 300 nM in said assay. In some embodiments, said metabolic stabilizing compound is an agonist with an EC50 of less than 200 nM in said assay. In some embodiments, said metabolic stabilizing compound is an agonist with an EC50 of less than 100 nM in said assay. In some embodiments, said metabolic stabilizing compound is an agonist with an EC50 of less than 90 nM in said assay. In some embodiments, said metabolic stabilizing compound is an agonist with an EC50 of less than 80 nM in said assay. In some embodiments, said metabolic stabilizing compound is an agonist with an EC50 of less than 70 nM in said assay. In some embodiments, said metabolic stabilizing compound is an agonist with an EC50 of less than 60 nM in said assay. In some embodiments, said metabolic stabilizing compound is an agonist with an EC50 of less than 50 nM in said assay. In some embodiments, said metabolic stabilizing compound is an agonist with an EC50 of less than 40 nM in said assay. In some embodiments, said metabolic stabilizing compound is an agonist with an EC50 of less than 30 nM in said assay. In some embodiments, said metabolic stabilizing compound is an agonist with an EC50 of less than 20 nM in said assay. In some embodiments, said metabolic stabilizing compound is an agonist with an EC50 of less than 10 nM in said assay. In some embodiments, said metabolic stabilizing compound is an agonist with an EC50 in said assay of a value selected from the interval of 1 nM to 10 µM. In some embodiments, said metabolic stabilizing compound is an agonist with an EC50 in said assay of a value selected from the interval of 1 nM to 1 µM. In some embodiments, said metabolic stabilizing compound is an agonist with an EC50 in said assay of a value selected from the interval of 1 nM to 100 nM. In some embodiments, said metabolic stabilizing compound is an agonist with an EC50 in said assay of a value selected from the interval of 1 nM to 10 nM. In some embodiments, said metabolic stabilizing compound is selective for the GPCR.

In some embodiments, said metabolic stabilizing compound is orally bioavailable. In some embodiments, said oral bioavailability is at least 1%, at least 5%, at least 10%, at least 15%, at least 20%, at least 25%, at least 30%, at least 35%, at least 40%, or at least 45% relative to intraperitoneal administration. In some embodiments, said oral bioavailablity is at least 20%, at least 25%, at least 30%, at least 35%, at least 40%, or at least 45% relative to intraperitoneal administration. In some embodiments, said orally bioavailable metabolic stabilizing compound is further able to cross the blood-brain barrier.

In one embodiment, said metabolic stabilizing compound is not an antibody. In some embodiments, said metabolic stabilizing compound is not a peptide or polypeptide.

The invention also relates to a method for increasing GPR35 function in a cell, comprising contacting a cell expressing GPR35 with an effective amount of a metabolic stabilizing compound identifiable according to the method of: a) contacting a candidate compound with GPR35, and b) determining whether GPR35 functionality is increased, wherein an increase in GPR35 functionality is indicative of the candidate compound being a metabolic stabilizing compound. For example, the invention provides a method for increasing GPR35 function in a cell, comprising contacting a cell expressing GPR35 with an effective amount of a metabolic stabilizing compound identified according to the method of: a) contacting a candidate compound with GPR35, and b) determining whether GPR35 functionality is increased, wherein an increase in GPR35 functionality is indicative of the candidate compound being a metabolic stabilizing compound.

In addition, the invention relates to a method for preparing a composition which comprises identifying a metabolic stabilizing compound and then admixing said compound with a pharmaceutically acceptable carrier, wherein said compound is identifiable by the method of: a) contacting a candidate compound with GPR35, and b) determining whether GPR35 functionality is increased, wherein an increase in GPR35 functionality is indicative of the candidate compound being a metabolic stabilizing compound. For example, the invention provides a method for preparing a composition which comprises identifying a metabolic stabilizing compound and then admixing said compound with a pharmaceutically acceptable carrier, wherein said compound is identified by the method of: a) contacting a candidate compound with GPR35, and b) determining whether GPR35 functionality is increased, wherein an increase in GPR35 functionality is indicative of the candidate compound being a metabolic stabilizing compound.

The invention also provides a pharmaceutical composition comprising, consisting essentially of, or consisting of the metabolic stabilizing compound identified according to the method of: a) contacting a candidate compound with GPR35, and b) determining whether GPR35 functionality is increased, wherein an increase in GPR35 functionality is indicative of the candidate compound being a metabolic stabilizing compound, and a pharmaceutically acceptable carrier.

Some embodiments of the present invention include a method of producing a pharmaceutical composition comprising admixing at least one compound according to any of the compound embodiments disclosed herein and a pharmaceutically acceptable carrier.

A compound of the present invention can be formulated into pharmaceutical compositions using techniques well known to those in the art. Suitable pharmaceutically-acceptable carriers, outside those mentioned herein, are available to those in the art; for example, see Remington's Pharmaceutical Sciences, 16$^{th}$ Edition, 1980, Mack Publishing Co., (Oslo et al., eds.).

While it is possible that, for use in the prophylaxis or treatment, a compound of the invention can in an alternative use be administered as a raw or pure chemical, it can be useful to present the compound or active ingredient as a pharmaceutical formulation or composition further comprising a pharmaceutically acceptable carrier.

The invention thus further provides pharmaceutical formulations comprising a compound of the invention or a pharmaceutically acceptable salt or derivative thereof together with one or more pharmaceutically acceptable carriers thereof and/or prophylactic ingredients. The carrier(s) must be "acceptable" in the sense of being compatible with the other ingredients of the formulation and not overly deleterious to the recipient thereof.

Pharmaceutical formulations include those suitable for oral, rectal, nasal, topical (including buccal and sub-lingual), vaginal or parenteral (including intramuscular, sub-cutaneous and intravenous) administration or in a form suitable for administration by inhalation or insufflation.

The compounds of the invention, together with a conventional adjuvant, carrier, or diluent, can thus be placed into the form of pharmaceutical formulations and unit dosages thereof, and in such form can be employed as solids, such as tablets or filled capsules, or liquids such as solutions, suspensions, emulsions, elixirs, gels or capsules filled with the same, all for oral use, in the form of suppositories for rectal administration; or in the form of sterile injectable solutions for parenteral (including subcutaneous) use. Such pharmaceutical compositions and unit dosage forms thereof can comprise conventional ingredients in conventional proportions, with or without additional active compounds or principles, and such unit dosage forms can contain any suitable effective amount of the active ingredient commensurate with the intended daily dosage range to be employed.

For oral administration, the pharmaceutical composition can be in the form of, for example, a tablet, capsule, suspension or liquid. The pharmaceutical composition can be made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient can also be administered by injection as a composition wherein, for example, saline, dextrose or water can be used as a suitable pharmaceutically acceptable carrier.

The invention provides a method for treating or preventing a metabolic-related disorder in an individual in need thereof, comprising administering to said individual an effective amount of the pharmaceutical composition comprising, consisting essentially of, or consisting of a GPR35 agonist. For example, the invention provides a method for treating or preventing a metabolic-related disorder in an individual in need thereof, comprising administering to said individual an effective amount of the pharmaceutical composition comprising, consisting essentially of, or consisting of the metabolic stabilizing compound identified according to the method of: a) contacting a candidate compound with GPR35, and b) determining whether GPR35 functionality is increased, wherein an increase in GPR35 functionality is indicative of the candidate compound being a metabolic stabilizing compound. In one embodiment, said metabolic-related disorder is diabetes, Type I diabetes, Type II diabetes, inadequate glucose tolerance, insulin resistance, hyperglycemia, hyperinsulinemia, hyperlipidemia, hypertriglyceridemia, hypercholesterolemia, dyslipidemia, obesity, aging, Syndrome X, atherosclerosis, heart disease, stroke, hypertension, or peripheral vascular disease. In another embodiment said metabolic-related disorder is diabetes. In a further embodiment, said metabolic-related disorder is Type II diabetes. In another embodiment, said metabolic-related disorder is dyslipidemia. In one embodiment, the method comprises administering to said individual an effective amount of an agent used for the treatment of diabetes, blood lipid disorders, or obesity in combination with an effective amount of the pharmaceutical composition comprising, consisting essentially of, or consisting of the metabolic stabilizing compound identified according to the method of: a) contacting a candidate compound with GPR35, and b) determining whether GPR35 functionality is increased, wherein an increase in GPR35 functionality is indicative of the candidate compound being a metabolic stabilizing compound. In one embodiment, the individual is a mammal and in another embodiment the individual is a human.

For example, the invention provides a method of treating or preventing type II diabetes in an individual in need thereof, comprising administering to said individual an effective amount of a GPR35 agonist.

Also, for example, the invention provides a method of treating or preventing dyslipidemia in an individual in need thereof, comprising administering to said individual an effective amount of a GPR35 agonist.

In addition, for example, the invention provides a method of treating or preventing type II diabetes and dyslipidemia in an individual in need thereof, comprising administering to said individual an effective amount of a GPR35 agonist.

As used herein the term "treating" in reference to a disorder means a reduction in severity of one or more symptoms associated with a particular disorder. Therefore, treating a disorder does not necessarily mean a reduction in severity of all symptoms associated with a disorder and does not necessarily mean a complete reduction in the severity of one or more symptoms associated with a disorder. Similarly, the term "preventing" means prevention of the occurrence or onset of one or more symptoms associated with a particular disorder and does not necessarily mean the complete prevention of a disorder. The methods of the invention can be used to treat a metabolic-related disorder including, for example, diabetes or dyslipidemia.

The dose when using the compounds can vary within wide limits, and as is customary and is known to the physician, it is to be tailored to the individual conditions in each individual case. It depends, for example, on the nature and severity of the illness to be treated, on the condition of the patient, on the compound employed or on whether an acute or chronic disease state is treated or prophylaxis is conducted or on whether further active compounds are administered in addition to the compounds. Representative doses of the present invention include, about 0.01 mg to about 1000 mg, about 0.01 to about 750 mg, about 0.01 to about 500 mg, 0.01 to about 250 mg, 0.01 mg to about 200 mg, about 0.01 mg to 150 mg, about 0.01 mg to about 100 mg, and about 0.01 mg to about 75 mg. Multiple doses can be administered during the day, especially when relatively large amounts are deemed to be needed, for example 2, 3 or 4, doses. If appropriate, depending on individual behavior and as appropriate from the patients physician or care-giver it can be necessary to deviate upward or downward from the daily dose.

The amount of active ingredient, or an active salt or derivative thereof, required for use in treatment will vary not only with the particular salt selected but also with the route of administration, the nature of the condition being treated and the age and condition of the patient and will ultimately be at the discretion of the attendant physician or clinician. In general, one skilled in the art understands how to extrapolate in vivo data obtained in a model system, typically an animal model, to another, such as a human. Typically, animal models include, but are not limited to, the rodent diabetes models as described in Example 21, infra (other animal models have been reported by Reed and Scribner in Diabetes, Obesity and Metabolism, 1:75-86 (1999)). In some circumstances, these extrapolations can merely be based on the weight of the animal model in comparison to another, such as a mammal, for example, a human, however, more often, these extrapolations are not simply based on weights, but rather incorporate a variety of factors. Representative factors include the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized, on whether an acute or chronic disease state is being treated or prophylaxis is conducted or on whether further active compounds are administered in addition to the compounds and as part of a drug combination. The dosage regimen for treating a disease condition with the compounds and/or compositions of this invention is selected in accordance with a variety factors as cited above. Thus, the actual dosage regimen employed can vary widely and therefore can deviate from a preferred dosage regimen and one skilled in the art will recognize that dosage and dosage regimen outside these typical ranges can be tested and, where appropriate, can be used in the methods of this invention.

The desired dose can conveniently be presented in a single dose or as divided doses administered at appropriate intervals, for example, as two, three, four or more sub-doses per day. The sub-dose itself can be further divided, e.g., into a number of discrete loosely spaced administrations. The daily dose can be divided, especially when relatively large amounts are administered as deemed appropriate, into several, for example 2, 3 or 4, part administrations. If appropriate, depending on individual behavior, it can be necessary to deviate upward or downward from the daily dose indicated.

The compounds of the present invention can be administrated in a wide variety of oral and parenteral dosage forms. It will be obvious to those skilled in the art that the following dosage forms can comprise, as the active component, either a compound of the invention or a pharmaceutically acceptable salt of a compound of the invention.

For preparing pharmaceutical compositions from the compounds of the present invention, the selection of a suitable pharmaceutically acceptable carrier can be either solid, liquid or a mixture of both. Solid form preparations include powders, tablets, pills, capsules, cachets, suppositories, and dispersible granules. A solid carrier can be one or more substances which can also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component. In tablets, the active component is mixed with the carrier having the necessary binding capacity in suitable proportions and compacted to the desire shape and size.

The powders and tablets can contain varying percentage amounts of the active compound. A representative amount in a powder or tablet can contain from 0.5 to about 90 percent of the active compound; however, an artisan would know when amounts outside of this range are necessary. Suitable carriers for powders and tablets are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as an admixture of fatty acid glycerides or cocoa butter, is first melted and the active component is dispersed homogeneously therein, as by stirring. The molten homogenous mixture is then poured into convenient sized molds, allowed to cool, and thereby to solidify.

Formulations suitable for vaginal administration can be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution. Injectable preparations, for example, sterile injectable aqueous or oleaginous suspensions can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables.

The compounds according to the present invention can thus be formulated for parenteral administration (e.g. by injection, for example bolus injection or continuous infusion) and can be presented in unit dose form in ampoules, pre-filled syringes, small volume infusion or in multi-dose containers with an added preservative. The pharmaceutical compositions can take such forms as suspensions, solutions, or emulsions in oily or aqueous vehicles, and can contain formulatory agents such as suspending, stabilizing and/or dispersing agents. Alternatively, the active ingredient can be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavors, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations can contain, in addition to the active component, colorants, flavors, stabilizers, buffers, artificial and natural sweeteners, dispersants, thickeners, solubilizing agents, and the like.

For topical administration to the epidermis the compounds according to the invention can be formulated as ointments, creams or lotions, or as a transdermal patch.

Ointments and creams can, for example, be formulated with an aqueous or oily base with the addition of suitable thickening and/or gelling agents. Lotions can be formulated with an aqueous or oily base and will in general also contain one or more emulsifying agents, stabilizing agents, dispersing agents, suspending agents, thickening agents, or coloring agents.

Formulations suitable for topical administration in the mouth include lozenges comprising active agent in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations can be provided in single or multi-dose form. In the latter case of a dropper or pipette, this can be achieved by the patient administering an appropriate, predetermined volume of the solution or suspension. In the case of a spray, this can be achieved for example by means of a metering atomizing spray pump.

Administration to the respiratory tract can also be achieved by means of an aerosol formulation in which the active ingredient is provided in a pressurized pack with a suitable propellant. If the compounds of the invention qr pharmaceutical compositions comprising them are administered as aerosols, for example as nasal aerosols or by inhalation, this can be carried out, for example, using a spray, a nebulizer, a pump nebulizer, an inhalation apparatus, a metered inhaler or a dry powder inhaler. Pharmaceutical forms for administration of the compounds of the invention as an aerosol can be prepared by processes well-known to the person skilled in the art. For their preparation, for example, solutions or dispersions of the compounds of the invention in water, water/alcohol mixtures or suitable saline solutions can be employed using customary additives, for example benzyl alcohol or other suitable preservatives, absorption enhancers for increasing the bioavailability, solubilizers, dispersants and others, and, if appropriate, customary propellants, for example include carbon dioxide, CFC's, such as, dichlorodifluoromethane, trichlorofluoromethane, or dichlorotetrafluoroethane; and the like. The aerosol can conveniently also contain a surfactant such as lecithin. The dose of drug can be controlled by provision of a metered valve.

In formulations intended for administration to the respiratory tract, including intranasal formulations, the compound will generally have a small particle size for example of the order of 10 microns or less. Such a particle size can be obtained by means known in the art, for example by micronization. When desired, formulations adapted to give sustained release of the active ingredient can be employed.

Alternatively the active ingredients can be provided in the form of a dry powder, for example, a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition can be presented in unit dose form for example in capsules or cartridges of, e.g., gelatin, or blister packs from which the powder can be administered by means of an inhaler.

The pharmaceutical preparations can be in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are particularly useful compositions.

Metabolic-related disorders include, for example, diabetes, Type I diabetes, Type II diabetes, inadequate glucose tolerance, insulin resistance, hyperglycemia, hyperinsulinemia, hyperlipidemia, hypertriglyceridemia, hypercholesterolemia; dyslipidemia, obesity, aging, Syndrome X, atherosclerosis, heart disease, stroke, hypertension, and peripheral vascular disease. Diabetes and related conditions such as insulin resistance have been described above herein.

Dyslipidemia is a general term for abnormal concentrations of blood lipids such as cholesterol, triglycerides and lipoproteins. For example, dyslipidemia includes terms such as hyperlipidemia which is a term for elevated concentrations of any or all of the lipids in the plasma such as cholesterol, triglycerides and lipoproteins. Hyperlipidemia can be acquired or can be congenital. Specific forms of hyperlipidemia can include, for example, hypercholesteremia, familial dysbetalipoproteinemia, diabetic dyslipidemia, nephrotic dyslipidemia and familial combined hyperlipidemia. Hypercholesteremia is characterized by an elevation in serum low density lipoprotein-cholesterol and serum total cholesterol. Familial dysbetalipoproteinemia, also known as Type III hyperlipidemia, is characterized by an accumulation of very low density lipoprotein-cholesterol (VLDL-cholesterol) particles called beta-VLDLs in the serum. Also associated with this condition, is a replacement of normal apolipoprotein E3 with abnormal isoform apolipoprotein E2. Diabetic dyslipidemia is characterized by multiple lipoprotein abnormalities, such as an overproduction of VLDL-cholesterol, abnormal VLDL triglyceride lipolysis, reduced LDL-cholesterol receptor activity and, on occasion, Type III hyperlipidemia. Nephrotic dyslipidemia is difficult to treat and frequently includes hypercholesteremia and hypertriglyceridemia. Familial combined hyperlipidemia is characterized by multiple phenotypes of hyperlipidemia, i.e., Type IIa, IIb, IV, V or hyperapobetalipoproteinemia.

Atherosclerosis is a process where deposits of fatty substances, cholesterol and other substances build up in the inner lining of an artery. This buildup is called plaque. Plaques that rupture cause blood clots to form that can block blood flow to the heart (heart attack) or the brain (stroke). Heart attack is the number one cause of death for both men and women in the United States and stroke is the number three cause of death [see, for example, Nature Medicine, Special Focus on Atherosclerosis, (2002) 8:1209-1262]. Abnormally high levels of circulating lipids are a major predisposing factor in development of atherosclerosis. Elevated levels of low density lipoprotein (LDL) cholesterol, elevated levels of triglycerides, or low levels of high density lipoprotein (HDL) cholesterol are, independently, risk factors for atherosclerosis and associated pathologies.

Heart disease includes, but is not limited to, cardiac insufficiency, coronary insufficiency, coronary artery disease, and high blood pressure. Peripheral vascular disease refers to diseases of blood vessels outside the heart and brain. Organic peripheral vascular diseases are caused by structural changes in the blood vessels, such as inflammation and tissue damage. Peripheral artery disease is an example. Peripheral artery disease (PAD) is a condition similar to coronary artery disease and carotid artery disease. In PAD, fatty deposits build up along artery walls and affect blood circulation, mainly in arteries leading to the legs and feet. In its early stages a common symptom is cramping or fatigue in the legs and buttocks during activity. Such cramping subsides when the person stands still. This is called "intermittent claudication." People with PAD have a higher risk of death from stroke and heart attack, due to the risk of blood clots.

Syndrome X, also called metabolic syndrome, is characterized by a group of metabolic risk factors in one person. They include: central obesity (excessive fat tissue in and around the abdomen), atherogenic dyslipidemia (blood fat disorders—mainly high triglycerides and low HDL cholesterol), raised blood pressure (130/85 mmHg or higher), insulin resistance or glucose intolerance, prothrombotic state (e.g., high fibrinogen or plasminogen activator inhibitor [−1] in the blood), and proinflammatory state (e.g., elevated high-sensitivity C-reactive protein in the blood).

While the compounds of the invention can be administered as the sole active pharmaceutical agent as described herein above, they can also be used in combination with one or more agents including, for example, agents that are used for the treatment of diabetes, blood lipid disorders, or obesity. For example, they can be used in combination with one or more agents belonging to the class of drugs known as α-glucosidase inhibitors, aldose reductase inhibitors, biguanides, thiazolidinediones, meglitinides, sulfonylureas, insulin, HMG-CoA reductase inhibitors, squalene synthesis inhibitors, fibrate compounds, LDL catabolism enhancers, angiotensin converting enzyme (ACE) inhibitors, lipase inhibitors, serotonin and/or noradrenaline releasers or reuptake inhibitors.

α-Glucosidase inhibitors belong to the class of drugs which competitively inhibit digestive enzymes such as α-amylase, maltase, α-dextrinase, sucrase, etc. in the pancreas and or small intestine. The reversible inhibition by α-glucosidase inhibitors retard, diminish or otherwise reduce blood glucose levels by delaying the digestion of starch and sugars. Some representative examples of α-glucosidase inhibitors include acarbose, N-(1,3-dihydroxy-2-propyl)valiolamine (generic name; voglibose), miglitol, and α-glucosidase inhibitors known in the art.

The class of aldose reductase inhibitors are drugs which inhibit the first-stage rate-limiting enzyme in the polyol pathway and thereby prevent or arrest diabetic complications. In the hyperglycemic state of diabetes, the utilization of glucose in the polyol pathway is increased and the excess sorbitol accumulated intracellularly as a consequence acts as a tissue toxin and hence evokes the onset of complications such as diabetic neuropathy, retinopathy, and nephropathy. Examples of the aldose reductase inhibitors include tolurestat; epalrestat; 3,4-dihydro-2,8-diisopropyl-3-thioxo-2H-1,4-benzoxazine-4-acetic acid; 2,7-difluorospiro(9H-fluorene-9,4'-imidazolidine)-2',5'-dione (generic name: imirestat); 3-[(4-bromo-2-flurophenyl)methyl]-7-chloro-3,4-dihydro-2,4-dioxo-1(2H)-quinazoline acetic acid (generic name: zenarestat); 6-fluoro-2,3-dihydro-2',5'-dioxo-spiro[4H-1-benzopyran-4,4'-imidazolidine]-2-carboxamide (SNK-860); zopolrestat; sorbinil; and 1-[(3-bromo-2-benzofuranyl)sulfonyl]-2,4-imidazolidinedione (M-16209), and aldose reductase inhibitors known in the art.

The biguanides are a class of drugs that stimulate anaerobic glycolysis, increase the sensitivity to insulin in the peripheral tissues, inhibit glucose absorption from the intestine, suppress of hepatic gluconeogenesis, and inhibit fatty acid oxidation. Examples of biguanides include phenformin, metformin, buformin, and biguanides known in the art.

Insulin secretion enhancers belong to the class of drugs having the property to promote secretion of insulin from pancreatic β cells. Examples of the insulin secretion enhancers include sulfonylureas (SU). The sulfonylureas (SU) are drugs which promote secretion of insulin from pancreatic β cells by transmitting signals of insulin secretion via SU receptors in the cell membranes. Examples of the sulfonylureas include tolbutamide; chlorpropamide; tolazamide; acetohexamide; 4-chloro-N-[(1-pyrolidinylamino) carbonyl]-benzenesulfonamide (generic name: glycopyramide) or its ammonium salt; glibenclamide (glyburide); gliclazide; 1-butyl-3-metanilylurea; carbutamide; glibonuride; glipizide; gliquidone; glisoxepid; glybuthiazole; glibuzole; glyhexamide; glymidine; glypinamide; phenbutamide; tolcyclamide, glimepiride, and other insulin secretion enhancers known in the art. Other insulin secretion enhancers include N-[[4-(1-methylethyl)cyclohexyl)carbonyl]-D-phenylalanine (Nateglinide); calcium (2S)-2-benzyl-3-(cis-hexahydro-2-isoindolinylcarbonyl)propionate dihydrate (Mitiglinide, KAD-1229); and other insulin secretion enhancers known in the art.

Thiazolidinediones belong to the class of drugs more commonly known as TZDs. Thiazolidinediones are a class of drugs for type 2 diabetes that lower the blood sugar by increasing the sensitivity of cells to insulin. Insulin can then move glucose from the blood into cells for energy. These drugs can also increase HDL.

Examples of thiazolidinediones include rosiglitazone, pioglitazone, and thiazolidinediones known in the art. Rezulin (troglitazone) was the first drug in this class in the U.S., but was taken off the market because of liver toxicity. Sister compounds now available with a better safety profile include Actos (pioglitazone) and Avandia (rosiglitazone). The main contraindications to the use of these medications include liver disease and heart failure. These drugs can also cause a significant increase in fluid retention and thereby increase the risk of heart failure.

Meglitinides are used to stop the rapid rise in blood sugar that can occur immediately after a person with type 2 diabetes eats a meal. These compounds, which include, for example, repaglinide (Prandin) and nateglinide (Starlix), work by increasing the amount of insulin produced by the pancreas similar to the way sulfonyurea medications work. Meglitinides are taken before eating a meal. Side effects associated with this class of drugs includes low blood sugar, upper respiratory infections including sinus conditions, headache, joint and back pain, nausea, diarrhea and constipation.

The different types of insulin are categorized according to how fast they start to work (onset) and how long they continue to work (duration). The types now available include rapid-, short-, intermediate-, and long-acting insulin. There are premixed rapid- and intermediate-acting insulins available, including: 70% intermediate-acting (NPH) and 30% short-acting regular insulin, called 70/30 insulin; 50% intermediate-acting (NPH) and 50% short-acting regular insulin, called 50/50 insulin; 75% intermediate-acting (NPH) and 25% rapid-acting Humalog (lispro), called 75/25 insulin; 70% intermediate-acting (NPH); and 30% rapid-acting NovoLog (insulin aspart), called NovoLog Mix 70/30. Insulin usually is given as an injection into the tissues under the skin (subcutaneous). It can also be given through an insulin pump or jet injector, a device that sprays the medication into the skin.

Insulin lets sugar (glucose) enter cells, where it is used for energy. Without insulin, the blood sugar level rises above what is safe for the body. Usually, a rapid- or short-acting and an intermediate- or long-acting insulin is taken to provide the constant and variable levels of insulin that the body needs. The short-acting insulin reduces blood sugar levels quickly and then wears off. Some long-acting insulins start taking effect when rapid- or short-acting insulins begin to wear off. The new long-acting insulin, Lantus, starts to work within a few minutes after it is given and continues to work at the same rate for about 24 hours.

The combination of a rapid- or short-acting and intermediate- or long-acting insulin helps keep blood sugar levels within a range that is safe for the body throughout the day. Thus insulin can be used to treat people with type 1 diabetes, people with type 2 diabetes whose pancreas produces little or no insulin or whose oral medications do not control their blood sugar. These people may take insulin either alone or along with oral medication, people with type 2 diabetes whose blood sugar levels are high because of a severe illness or major surgery, women with type 2 diabetes who are pregnant or breast-feeding who cannot keep their blood sugar levels within a safe range with diet and exercise. Only one oral diabetes medication (glyburide) has been studied for use during pregnancy.

The major side effect of insulin can be a dangerously low blood sugar level (severe hypoglycemia). A very low blood sugar level can develop within 10 to 15 minutes. Insulin can contribute to weight gain, especially in people with type 2 who already are overweight. Other possible side effects of long-term insulin use include the loss of fatty tissue (lipodystrophy) where the insulin is injected and, rarely, allergic reactions that include swelling (edema).

Statin compounds belong to a class of drugs that lower blood cholesterol levels by inhibiting hydroxymethylglutalyl CoA (HMG-CoA) reductase. HMG-CoA reductase is the rate-limiting enzyme in cholesterol biosynthesis. A statin that inhibits this reductase lowers serum LDL concentrations by upregulating the activity of LDL receptors and responsible for clearing LDL from the blood. Examples of the statin compounds include rosuvastatin, pravastatin and its sodium salt, simvastatin, lovastatin, atorvastatin, fluvastatin, cerivastatin, and HMG-CoA reductase inhibitors known in the art.

Squalene synthesis inhibitors belong to a class of drugs that lower blood cholesterol levels by inhibiting synthesis of squalene. Examples of the squalene synthesis inhibitors include (S)-α-[Bis[2,2-dimethyl-1-oxopropoxy)methoxy]phosphinyl]-3-phenoxybenzenebutanesulfonic acid, mono potassium salt (BMS-188494) and squalene synthesis inhibitors known in the art.

Fibrate compounds belong to a class of drugs that lower blood cholesterol levels by inhibiting synthesis and secretion of triglycerides in the liver and activating a lipoprotein lipase. Fibrates have been known to activate peroxisome proliferators-activated receptors and induce lipoprotein lipase expression. Examples of fibrate compounds include bezafibrate, beclobrate, binifibrate, ciplofibrate, clinofibrate, clofibrate, clofibric acid, etofibrate, fenofibrate, gemfibrozil, nicofibrate, pirifibrate, ronifibrate, simfibrate, theofibrate, and fibrates known in the art.

LDL (low-density lipoprotein) catabolism enhancers belong to a class of drugs that lower blood cholesterol levels by increasing the number of LDL (low-density lipoprotein) receptors, examples include LDL catabolism enhancers known in the art.

Angiotensin converting enzyme (ACE) inhibitors belong to the class of drugs that partially lower blood glucose levels as well as lowering blood pressure by inhibiting angiotensin converting enzymes. Examples of the angiotensin converting enzyme inhibitors include captopril, enalapril, alacepril, delapril; ramipril, lisinopril, imidapril, benazepril, ceronapril, cilazapril, enalaprilat, fosinopril, moveltopril, perindopril, quinapril, spirapril, temocapril, trandolapril, and angiotensin converting enzyme inhibitors known in the art.

Lipase inhibitors include, for example, anti-obesity compounds such as Orlistat (XENICAL™). Orlistat inhibits fat absorption directly but also tends to produce a high incidence of unpleasant gastric side-effects such as diarrhea and flatulence.

Another class of anti-obesity drugs includes serotonin and/or noradrenaline releasers or reuptake inhibitors. For example, sibutramine (Meridia™) is a mixed 5-HT/noradrenaline reuptake inhibitor. The main side effect of sibutramine can be an increase in blood pressure and heart rate in some patients. The serotonin releaser/reuptake inhibitors fenfluramine (Pondimin™) and dexfenfluramine (Redux™) have been reported to decrease food intake and body weight over a prolonged period (greater than 6 months). However, both products were withdrawn from use after reports of preliminary evidence of heart valve abnormalities associated with their use.

Some embodiments of the invention include, a pharmaceutical composition comprising a compound of the invention or a pharmaceutically acceptable salt thereof in combination with at least one member selected from the group consisting of an α-glucosidase inhibitor, an aldose reductase inhibitor, a biguanide, a HMG-CoA reductase inhibitor, a squalene synthesis inhibitor, a fibrate compound, a LDL catabolism enhancer and an angiotensin converting enzyme inhibitor. In another embodiment, the pharmaceutical composition is a compound of the invention or a pharmaceutically acceptable salt thereof in combination with a HMG-CoA reductase inhibitor. In still another embodiment, the HMG-CoA reductase inhibitor is selected from the group consisting of prevastatin, simvastatin, lovastatin, atorvastatin, fluvastatin and lipitor.

In accordance with the present invention, the combination can be used by mixing the respective active components either all together or independently with a physiologically acceptable carrier, excipient, binder, diluent, etc., as described herein above, and administering the mixture or mixtures either orally or non-orally as a pharmaceutical composition. When a compound or a mixture of compounds of the invention are administered as a combination therapy or prophylaxis with another active compound the therapeutic agents can be formulated as a separate pharmaceutical compositions given at the same time or at different times, or the therapeutic agents can be given as a single composition.

The invention also provides a method for decreasing blood glucose levels in an individual in need thereof, comprising administering to said individual an effective amount of the pharmaceutical composition comprising, consisting essentially of, or consisting of the metabolic stabilizing compound identified according to the method of: a) contacting a candidate compound with GPR35, and b) determining whether GPR35 functionality is increased, wherein an increase in GPR35 functionality is indicative of the candidate compound being a metabolic stabilizing compound. In one embodiment, the method comprises administering to said individual an effective amount of an agent used for the treatment of diabetes, blood lipid disorders, or obesity in combination with an effective amount of the pharmaceutical composition comprising, consisting essentially of, or consisting of the metabolic stabilizing compound identified according to the method of: a) contacting a candidate compound with GPR35, and b) determining whether GPR35 functionality is increased, wherein an increase in GPR35 functionality is indicative of the candidate compound being a metabolic stabilizing compound. In one embodiment, the individual is a mammal and in another embodiment the individual is a human.

The invention also provides a method for decreasing free fatty acid levels in an individual in need thereof, comprising administering to said individual an effective amount of the pharmaceutical composition comprising, consisting essentially of, or consisting of the metabolic stabilizing compound identified according to the method of: a) contacting a candidate compound with GPR35, and b) determining whether GPR35 functionality is increased, wherein an increase in GPR35 functionality is indicative of the candidate compound being a metabolic stabilizing compound. In one embodiment, the method comprises administering to said individual an effective amount of an agent used for the treatment of diabetes, blood lipid disorders, or obesity in combination with an effective amount of the pharmaceutical composition comprising, consisting essentially of, or consisting of the metabolic stabilizing compound identified according to the method of: a) contacting a candidate compound with GPR35, and b) determining whether GPR35 functionality is increased, wherein an increase in GPR35 functionality is indicative of the candidate compound being a metabolic stabilizing compound. In one embodiment, the individual is a mammal and in another embodiment the individual is a human.

The invention also provides a method for increasing GPR35 function, comprising contacting GPR35 with an effective amount of a metabolic stabilizing compound identified according to the method of: a) contacting a candidate compound with GPR35, and b) determining whether GPR35 functionality is increased, wherein an increase in GPR35 functionality is indicative of the candidate compound being a metabolic stabilizing compound. In addition, the invention provides a method for increasing GPR35 function in a human host, comprising administering a compound that selectively activates GPR35 in a human host in need of such treatment. The methods of the invention can be used to treat a metabolic-related disorder, for example, diabetes and/or dyslipidemia. The invention also provides a method for increasing GPR35 function in a cell, comprising contacting a cell expressing GPR35 with an effective amount of a metabolic stabilizing compound identified according to the method of: a) contacting a candidate compound with GPR35, and b) determining whether GPR35 functionality is increased, wherein an increase in GPR35 functionality is indicative of the candidate compound being a metabolic stabilizing compound. The cell can be, for example, in an individual or the cell can be an isolated cell.

The invention provides a method for treating or preventing a metabolic-related disorder, comprising administering to an individual in need thereof an effective amount of a GPR35 modulator. In one embodiment, said modulator is an agonist. In one embodiment, said metabolic-related disorder is diabetes, Type I diabetes, Type II diabetes, inadequate glucose tolerance, insulin resistance, hyperglycemia, hyperinsulinemia, hyperlipidemia, hypertriglyceridemia, hypercholesterolemia, dyslipidemia, obesity, aging, Syndrome X, atherosclerosis, heart disease, stroke, hypertension, or peripheral vascular disease. In another embodiment, said metabolic-related disorder is diabetes. In a further embodiment, said metabolic-related disorder is Type II diabetes. In another embodiment, said metabolic-related disorder is dyslipidemia.

In one embodiment said method further comprises administering to said individual an effective amount of an agent used for the treatment of diabetes, blood lipid disorders, or obesity in combination with an effective amount of a GPR35 modulator. In one embodiment, the individual is a mammal and in another embodiment the individual is a human.

The invention also provides a method for decreasing blood glucose levels in an individual in need thereof, comprising administering to the individual an effective amount of a GPR35 modulator. In one embodiment, said GPR35 modulator is an agonist. In one embodiment, the individual is a mammal and in another embodiment the individual is a human.

The invention also relates to a method for increasing glucose tolerance in an individual in need thereof, comprising administering to the individual an effective amount of a GPR35 modulator. In one embodiment, said GPR35 modulator is an agonist. In one embodiment, the individual is a mammal and in another embodiment the individual is a human.

The invention also relates to a method for potentiating glucose uptake in adipose tissue in an individual in need thereof, comprising administering to the individual an effective amount of a compound of formula (I). The invention further relates to a method for regulating intestinal glucose absorption in an individual in need thereof, comprising administering to the individual an effective amount of a compound of formula (I).

The invention also provides a method for decreasing free fatty acid levels in an individual in need thereof, comprising administering to the individual an effective amount of a GPR35 modulator. In one embodiment, said GPR35 modulator is an agonist. In one embodiment, the individual is a mammal and in another embodiment the individual is a human.

The invention also relates to a method for increasing HDL levels in an individual in need thereof, comprising administering to the individual an effective amount of a GPR35 modulator. In one embodiment, said GPR35 modulator is an agonist. In one embodiment, the individual is a mammal and in another embodiment the individual is a human.

One object of the invention relates to a method of a) performing a method of the invention to identify a metabolic stabilizing compound and (b) optionally, determining the structure of the compound, and (c) providing the compound or the name or structure of the compound. In addition, the invention relates to a method of a) performing a method of the invention to identify a metabolic stabilizing compound and (b) optionally, determining the structure of the compound, (c) optionally, providing the name or structure of the compound, and (d) producing or synthesizing the compound. The invention further relates to a process for modulating the functionality of a GPCR comprising performing a method of the invention to identify a metabolic stabilizing compound and then contacting the GPCR with the metabolic stabilizing compound or administering the metabolic stabilizing compound to an individual under conditions sufficient to modulate the functionality of the GPCR.

One object of the invention relates to a method of identifying whether a candidate compound binds to a GPR35 receptor comprising the steps of: (a) contacting the receptor with a detectably labeled known ligand of the receptor in the presence or absence of the candidate compound; and (b) determining whether the binding of said labeled known ligand to the receptor is inhibited in the presence of the candidate compound; wherein said inhibition is indicative of the candidate compound binding to the GPR35 receptor. In one embodiment, said contacting comprises contacting with a host cell or with membrane of a host cell that expresses the GPCR, wherein said host cell comprises an expression vector comprising a polynucleotide encoding the receptor.

Another object of the invention relates to a method for detecting a ligand that binds to a GPR35 receptor, comprising the steps of: (a) contacting a test ligand with a host cell or with membrane of a host cell that expresses said receptor, under conditions which permit interaction between said receptor and said test ligand; and (b) detecting a ligand bound to said receptor. In one embodiment, said contacting comprises contacting with a host cell or with membrane of a host cell that expresses the GPCR, wherein said host cell comprises an expression vector comprising a polynucleotide encoding the receptor.

Applicants reserve the right to exclude any one or more modulators from any of the embodiments of the invention. Applicants further reserve the right to exclude any polynucleotide or polypeptide from any of the embodiments of the invention. Applicants additionally reserve the right to exclude any metabolic-related disorder, or any complication of elevated blood glucose concentration from any of the embodiments of the invention.

Other uses of the disclosed receptors and methods will become apparent to those in the art based upon, inter alia, a review of this patent document.

The following examples are given to illustrate the invention and are not intended to be inclusive in any manner:

EXAMPLES

The compounds of the present invention and their syntheses are further illustrated by the following examples. The examples are provided to further define the invention without, however, limiting the invention to the specifics of these examples.

Example 1

Affymetrix Chip Expression of Human GPR35

In this example, the expression level of human GPR35 was determined in several human cell types and tissues using an Affymetrix GeneChip®.
1. Affymetrix Genechip® Technology Nucleotide sequences corresponding to several G protein-coupled receptors (GPCRs) were submitted to Affymetrix. Affymetrix designed and manufactured an oligonucleotide microarray for the purpose of measuring mRNA expression levels of these receptors in various tissues via its GeneChip® Technology. RNA samples from a large number of tissue and cell types, including human brain sub-regions (Harvard Brain Bank), human cell lines (Axiom) and peripheral tissues, were amplified, labeled, hybridized to the microarray, and data analyzed according to manufacturer's instructions.

GPCRs were determined to be expressed if the expression index was greater than 50 (based upon and according to manufacturer's instructions). The data was analyzed and had indicated that classification of GPCRs with an expression index greater than 50 was reasonable because a number of known GPCRs had previously been reported to be expressed in neuronal tissues with an expression index greater than 50.

Using the GeneChip®, Applicant has discovered GPR35 has high levels of expression in monocytes (adherent and CD14+), eosinophils, bowel (small intestine, colon, rectum, duodenum), stomach, and pancreatic islet cells (see FIG. 1).

Example 2

Mouse GPR35 RNase Protection Assay

In this example, the expression level of mouse GPR35 was determined in several mouse cell types and tissues using an RNase protection assay. As shown in FIG. 2, the highest level expression of mouse GPR35 was observed in spleen, 3T3-adipocytes and colon.

RNAs were commercially obtained (Clontech) or isolated from 3T3 preadipocyte or adipocyte cells (as indicated in the figures) originally obtained as undifferentiated cells from ATCC. RNAs were isolated with the Invitrogen Trizol kit according to manufacturer's instructions.

A 236 bp segment of mouse GPR35 (from mouse GPR35 ORF515-750) was cloned into pCRII TOPO cloning vector (Invitrogen). The plasmid was linearized with HindIII. After gel purification of the fragment, a 362 bp segment of mouse GPR35 RPA probe was generated by in vitro transcription with T7 RNA polymerase (Ambion MAXIscript kit). The probe was purified by acrylamide gel electrophoresis and hybridized with 20 µg of each RNA sample at 55° C. overnight. The hybrids were digested with RNase on the next day and run on an acrylamide gel to detect the results (Ambion RPAIII kit). All the procedures for in vitro transcription and RPA reactions were following the manufacturer's instructions.

Mouse GPR35 Sequence for RPA Probe:

```
                                            (SEQ ID NO: 9)
5'-CTGCCTTCTCACTGCTGGGATTCTACCTGCCGCTGGCCATCGTGGTC

TTCTGCTCTTTGCAGGTAGTGACTGTGCTATCGAGAAGGCCAGCCGCTGA

TGTGGGGCAGGCAGAGGCCACCCAAAAGGCCACCCACATGGTCTGGGCCA

ACTTGGCTGTGTTTGTCATCTGCTTCCTGCCCTTGCATGTGGTCCTGACC

GTGCAGGTCTCCCTGAACCTCAATACCTGTGCTGCCCGA-3'
```

Primers for PCR Mouse GPR35 Probe:

```
RPAf1:
5'-CTGCCTTCTCACTGCTGGGATTCT-3'    (SEQ ID NO: 10)

RPAr1:
5'-TCGGGCAGCACAGGTATTGAGGTT-3'    (SEQ ID NO: 11)
```

Example 3

G-Alpha i and G-Alpha 12/13 Coupling of GPR35

In this example, the coupling of GPR35 to G-alpha i (Gαi) was determined using a GqGi chimera and the coupling of GPR35 to G-alpha 12/13 (Gα12/13) was shown using a CRE-Luc/GsG12/13 chimera.

Figure 3:
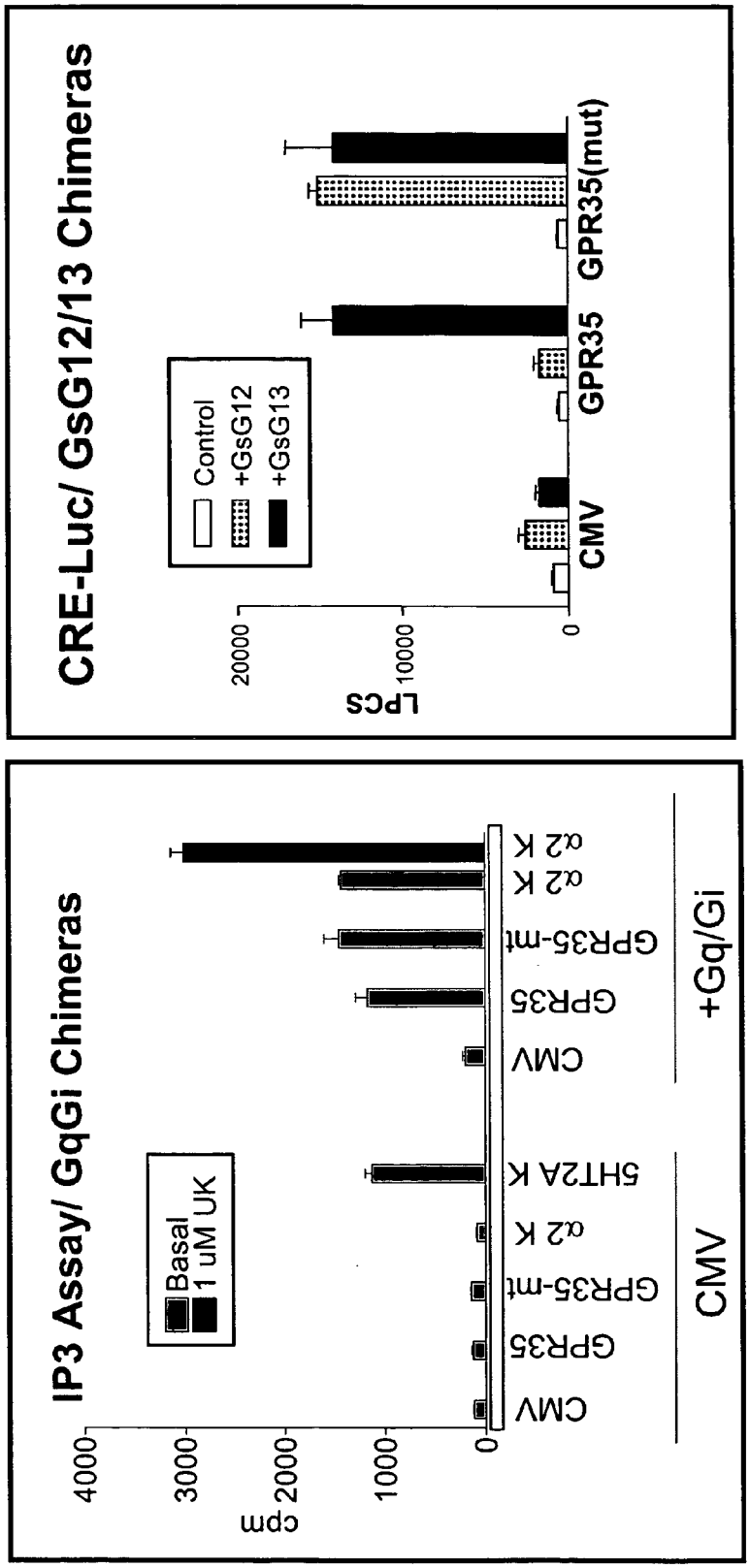
FIG. 3 shows coupling of GPR35 to G-proteins G-alpha i and G-alpha 12/13.

FIG. 3, left panel, illustrates the inositol tri-phosphate (IP3) accumulation in HEK 293 cells co-expressing human GPR35 (sequence used was the coding sequence nucleotides 60183-61112 of GenBank Accession No. AF158748, (SEQ ID NO:4) without the initiator methionine), or alternatively, an A216K mutant (mt) of GPR35 known to harbor increased constitutive activity, and the chimeric Gαq-subunit in which the last five amino acids have been replaced with the corresponding amino acids of Gαi (GqGi). This construct has been shown to convert the signaling of a Gi-coupled receptor to the Gq pathway (i.e. accumulation of inositol phosphates) in response to receptor activation.

For these experiments, full length human GPR35 was cloned into the HA/V5 pCMV vector with HA tag at 5' of the gene and V5 tag at 3' end of the gene. Note when the HA tag was added, the initiator methionine of GPR35 was deleted.

The GPR35 mutant A216K was generated by mutating an alanine at position 216 to a lysine.

HEK 293 cells were plated in 96-well tissue culture plates at 3×10$^6$ cells/plate in regular growth medium (DMEM/10% FBS). On the next day, various plasmid DNAs (as described in the figure) were transfected into cells with lipofectamine (Invitrogen). For every 6 wells, 80 ng of CMV or GPCRs, 80 ng of Gq/i and 40 ng of EGFP (a green fluorescent protein), plus 4 μl of lipofectamine and 100 μl of Opti-MEM were mixed to form DNA precipitates. After 30 minutes of incubation at RT, 200 μl of Opti-MEM were added to the precipitates. Well resuspended precipitates were aliquoted at 50 μl/well onto the cells after aspirating off the growth medium from the plate. Cells were incubated with DNA precipitates overnight.

After 24-hour post transfection, cells were changed to inositol-free medium with [$^3$H]-myoinositol and incubated for overnight. On the next morning, cells were changed to IP3 assay medium. For controls, cells were transfected with α2K, which is a constitutively active version of an α2 adrenergic receptor where a residue in the IC3 loop of the receptor at a position 16 residues from a conserved proline residue is changed to a lysine (see, for example, U.S. Pat. No. 6,555,339). Cells transfected with α2K were treated with the ligand of the receptor (1 μM UK 14,304 ligand) for 3-4 hours. The 5HT2Ak construct is a serotonin receptor 2A constitutively active mutant made in the same manner. IP3 medium was then removed and 200 μl/well 0.1M formic acid was added. Cell lysates were made by freezing the plate at −80° C. for 30 minutes and thawing at 37° C. While the plate was being thawed, a total 400 μl/well of formate resin slurry was added to the multiscreen plate. After the plate was drained completely, the cell lysate was added onto the plate and incubated for 5 minutes. The plate was drained and then washed with water 5 times. Finally, 200 μl/well of 1M ammonium formate/0.1M formic acid was added to elute the plate. The eluates were transferred to scintillation vials to count the IP3 production.

FIG. 3, right panel, illustrates the cAMP responsive transcriptional activity in 293 cells transfected with a CRE-luciferase plasmid, a CMV-GPR35 expression plasmid and a CMV-GsG12 or CMV-GsG13 plasmid. In this experiment, the G12 or G13 coupling of GPR35 is redirected toward activation of adenylyl cyclase, resulting in elevated cAMP. This is detected by the CRE-Luciferase "reporter."

For the CRE-LUC experiments, GsG12 or GsG13 chimera were made by replacing the last 11 amino acids of Gαs with the corresponding amino acids of Gα12 or Gα13. The chimeras were cloned into myc/pcDNA3 vector with myc tag at 5'end of the gene.

HEK 293 cells were plated in 96-well tissue culture plates at 2×10$^6$ cells/plate in regular growth medium (DMEM/10% FBS). On the next day, various plasmid DNAs (as described in the figure) were transfected into cells with lipofectamine (Invitrogen). For every 6 wells, 400 ng of CRE-Luc, 20 ng of CMV or GPCRs, 20 ng of GsG12 or GsG13 and 10 ng of SEAP-Luc (a control luciferase plasmid from Clonetech), plus 2.5 μl of lipofectamine and 50 μl of Opti-MEM were mixed to form DNA precipitates. After 30 minutes of incubation at room temperature, 300 μl of Opti-MEM were added to the precipitates. Well resuspended precipitates were aliquoted at 50 μl/well onto the cells after aspirating off the growth medium from the plate. Cells were incubated with DNA precipitates overnight and the luciferase activities were measured at 24-hours post-transfection with LUCLITE Kit (Packard) according to manufacturer's protocol.

G alpha i signaling has been shown to be involved in energy homeostasis. In muscle, G alpha i signaling can result in enhanced insulin sensitivity; in adipocytes, G alpha i signaling can result in enhanced HDL levels and decreased lipolysis; in pancreatic alpha cells, G alpha i signaling can result in decreased glucagon release; and in liver, G alpha i signaling can result in decreased glucagon action.

Example 4

Figure 4:
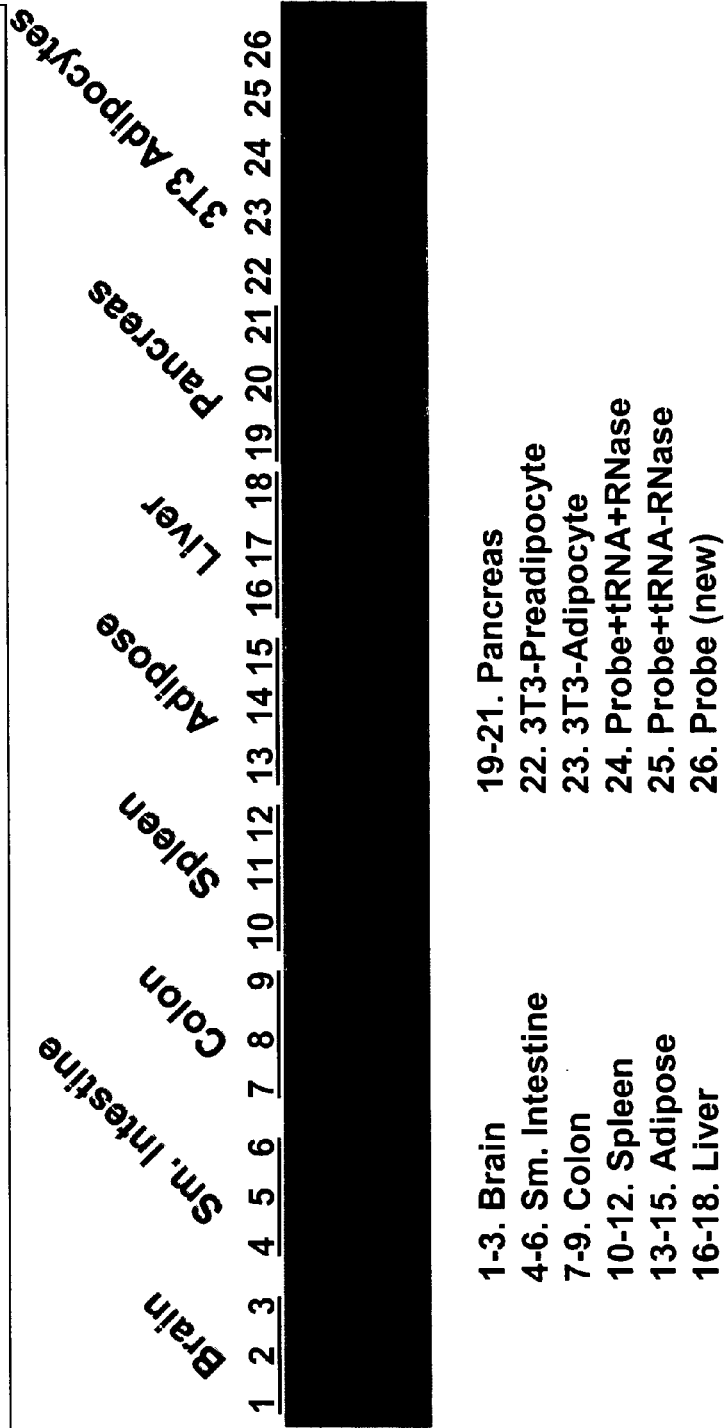
FIG. 4 shows RNase protection assay analysis of mouse GPR35 expression in selected cell types and tissues of wild-type C57B1/6, ob/ob, and db/db mice.

Mouse GPR35 RNase Protection Assay in Selected Cell Types and Tissues of Wild-Type, ob/ob, and db/db Mice In this example, the expression of GPR35 was determined in selected cell types and tissues in wild-type C57/b16 mice, ob/ob mutant mice, and db/db mutant mice. As seen in FIG. 4, mouse GPR35 is expressed at a higher level in adipose and liver in ob/ob mice compared to wild-type mice and is expressed at a higher level in adipose, liver, and pancreas in db/db mice compared to wild-type mice indicating that GPR35 can function as a regulator of energy homeostasis.

RNAs were isolated from tissues of about 17 week old C57, ob/ob, or db/db mice. RNAs were isolated using RNA-BEE isolation kit according to manufacturer's instructions. 3T3 adipocyte RNA was isolated as described in Example 2 above.

A 236 bp segment of mouse GPR35 (from mouse GPR35 ORF515-750) was cloned into TOPO pCRII cloning vector (Invitrogen). The plasmid was linearized with HindIII. After gel purification of the fragment, a 362 bp segment of mouse GPR35 RPA probe was generated by in vitro transcription with T7 RNA polymerase (Ambion MAXIscript kit). The probe was purified by acrylamide gel electrophoresis and hybridized with 20 μg of each RNA sample at 55° C. overnight. The hybrids were digested with RNase on the next day and run on an acrylamide gel to detect the results (Ambion RPAIII kit). All the procedures for in vitro transcription and RPA reactions were following the manufacturer's instructions.

Mouse GPR35 Sequence for RPA Probe:

```
                                          (SEQ ID NO: 9)
5'-CTGCCTTCTCACTGCTGGGATTCTACCTGCCGCTGGCCATCGTGGTC

TTCTGCTCTTTGCAGGTAGTGACTGTGCTATCGAGAAGGCCAGCCGCTGA

TGTGGGGCAGGCAGAGGCCACCCAAAAGGCCACCCACATGGTCTGGGCCA

ACTTGGCTGTGTTTGTCATCTGCTTCCTGCCCTTGCATGTGGTCCTGACC

GTGCAGGTCTCCCTGAACCTCAATACCTGTGCTGCCCGA-3'
```

Primers for PR Mouse GPR35 Probe:

```
RPAf1:
5'-CTGCCTTCTCACTGCTGGGATTCT-3'     (SEQ ID NO: 10)

RPAr1:
5'-TCGGGCAGCACAGGTATTGAGGTT-3'     (SEQ ID NO: 11)
```

Example 5

Induction of GPR35 Expression in Liver and Pancreas of db/db Mice

Figure 5:
FIG. 5 shows RT-PCR analysis of mouse GPR35 expression in selected tissues of db/db mice compared to wild-type C57B1/6 mice.
Figure 5:
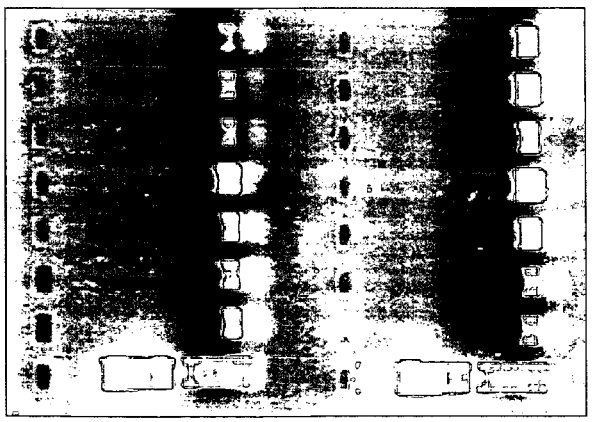

In this example, the expression of GPR35 in selected tissues of db/db mice was determined using RT-PCR. As seen in FIG. 5, GPR35 expression is induced in the liver, pancreas and adipose tissue of db/db mice compared to wild-type C57 B1/6 mice.

For these experiments, RNAs were isolated from tissues (as indicated in the figure) of about 17-week old C57 or db/db mice as described in Example 4. Subsequently, cDNAs were synthesized with AccuQuant cDNA Synthesis Kit (Quamta Biosciences) according to the manufacturer's protocol. For the reaction, 2 μg of RNA, 4 μl of 5× cDNA Ready Mix and 1 μl of AccuScript RT along with water were assembled into a total volume of 20 μl. The reactions were run in PCR machine at 22° C., 5 min; 42° C., 30 min; 85° C., 5 min.

PCR reactions were performed with Invitrogen's PLANTINUM PCR Supermix. For each reaction, 1 μl of cDNA, 45 μl Supermix, 1 μl of each primer (25 μM stock) were assembled in a volume of 50 μl total. The reactions were performed in the PCR machine at 94° C., 2 min denature, followed by 36 cycles of 94° C., 30 sec; 59° C., 30 sec; 72° C., 1 min, finally ended with extension at 72° C. for 7 minutes. GAPDH was run for all the samples as an internal control. The annealing temperature used for GAPDH was 63° C. and PCR was cycled for 25 times.

Mouse GPR35 RT-PCR Primer Pairs:

```
EST724f:
5'-CACGGGGTTCCACAGAGGTATG-3'        (SEQ ID NO: 12)

EST724r:
5'-CAATGGCAAGGAGCAGAGCAG-3'         (SEQ ID NO: 13)

GAPDH 5' Primer:
5'-ggggTgAggCCggTgCTgAgTAT-3'       (SEQ ID NO: 14)

GAPDH 3' Primer:
5'-CATTggggTAggAACACggAAgg-3'       (SEQ ID NO: 15)
```

Example 6

Differential Expression of GPR35 in the Pancreata of db/db and ob/ob Mice

Figure 6:
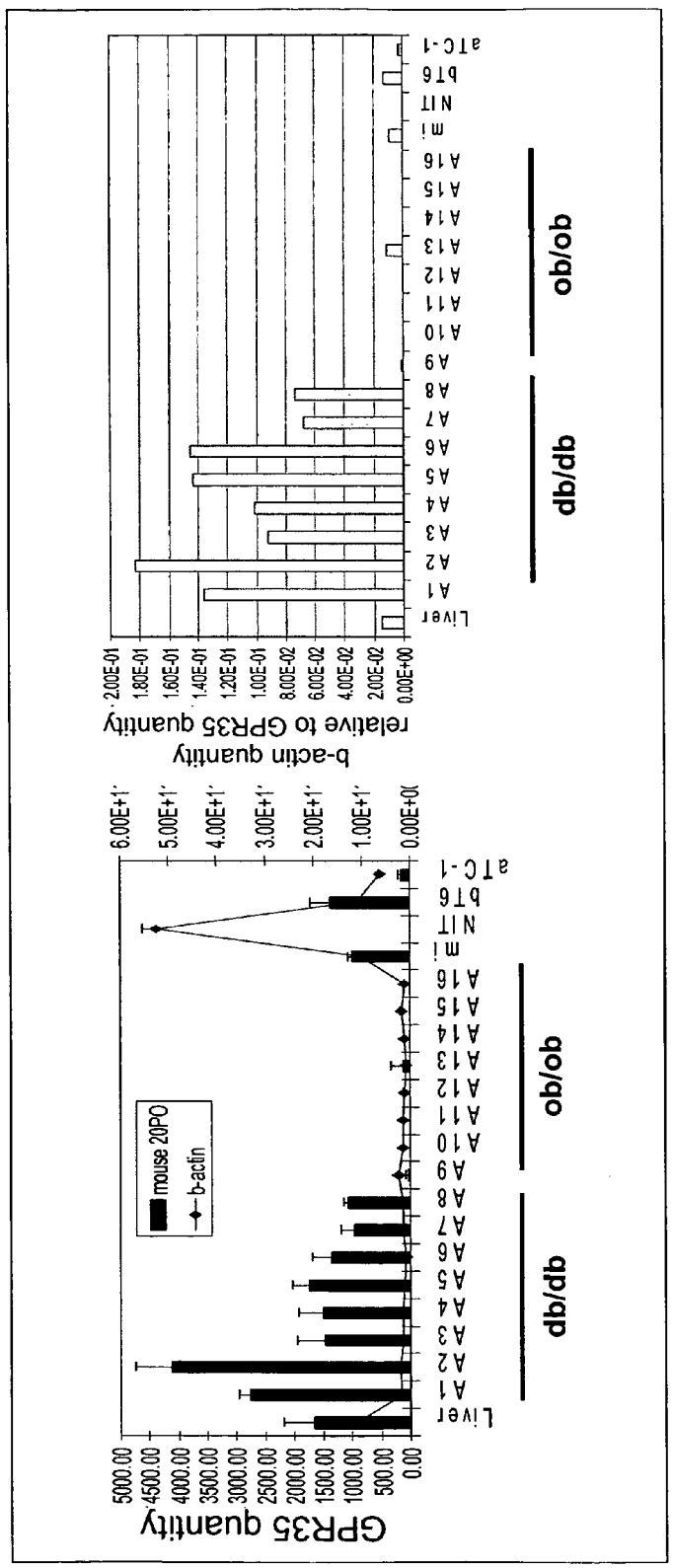
FIG. 6 shows TaqMan quantitative PCR analysis of mouse GPR35 in the pancreata of db/db and ob/ob mice.

In this example, the expression of GPR35 in pancreas from db/db and ob/ob mice was determined using TaqMan PCR. Samples A1-A8 are derived from the pancreas of eight different db/db mice and A9-A16 samples are derived from the pancreas of eight different ob/ob mice. As seen in FIG. 6, GPR35 is readily detected in the pancreata of db/db mice but not ob/ob mice.

For these experiments, RNAs were isolated from the pancreas from ob/ob and db/db mice with various ages and fasting treatments. Cells (as indicated in the figure) used for RNA isolation were pancreatic cell lines obtained from ATCC. Tissue RNAs were isolated using RNA-BEE RNA isolation kit and cell RNAs were isolated using the Invitrogen Trizol reagent kit. cDNAs were synthesized with AccuQuant cDNA Synthesis Kit (Quanta Biosciences) according to the manufacturer's protocol. The reactions, containing 2 μg of RNA, 4 μl of 5× cDNA Ready Mix and 1 μl of AccuScript RT along with water were assembled into a total volume of 20 μl. The reactions were run in a PCR machine at 22° C., 5 minutes; 42° C., 30 minutes; 85° C., 5 minutes.

AccuQuant qPCR MasterMix (Quanta BioSciences) was used for TaqMan PCR. The reactions were assembled according to the manufacturer's protocol. In each reaction, 0.4 μl of cDNA was used for each sample. The final concentration for each mouse GPR35 primer was 300 nM. The final TaqMan Probe concentration was 250 nM. A μ-actin primer and probe was included in the multiplex TaqMan PCR for amplifying μ-actin as an internal control. The final concentration for each μ-actin primer was 50 nM and the final μ-actin probe concentration was 200 nM. TaqMan PCR was performed in ABI7900 TaqMan PCR machine using the default thermal cycler condition: 50° C. for 2 min, 95° C. for 10 min, then repeat 40 cycles of 95° C. 15 seconds and 60° C. 1 min.

TaqMan PCR Primer and Probe Sets for Mouse GPR35:

```
(TF):
                                    (SEQ ID NO: 16)
5'-ATGCAGGAGGGTGGCTTCT-3'

(TR):
                                    (SEQ ID NO: 17)
5'-AGAAGGCAGTGGTGCTGAAATT-3'

M-GPR35TaqMan Probe:
                                    (SEQ ID NO: 18)
6FAM-CCTTCAGCAGCCAAACCCGGCG-TAMRA β3-actin 5' Primer:
                                    (SEQ ID NO: 19)
5'-TCCTGGCCTCACTGTCCAC-3'

β-actin 3' Primer:
                                    (SEQ ID NO: 20)
5'-GGGCCGGACTCATCGTACT-3'

β-actin TaqMan Probe:
                                    (SEQ ID NO: 21)
VIC-CTGCTTGCTGATCCACATCTGCTGGA-TAMERA
```

Example 7

Staining of Cells with Human GPR35 Antisera

In this example, HEK 293 cells expressing an empty CMV vector or hemagglutin (HA) tagged human GPR35 were stained with antibodies directed against HA and GPR35.

The GPR35 antibody was generated using a peptide with the amino acid sequence $NH_2$-RPPTDVGQAEATR-KAARC-COOH (SEQ ID NO:22). The peptide was conjugated to BSA and injected into chickens for antibody production. Anti-hGPR35 antibody (Y-antibody) was obtained from egg and affinity purified. Affinity purification was performed using a column containing the antigenic peptide SEQ ID NO:22 conjugated to agarose beads.

For the antibody staining, HEK 293 cells were plated at a density of $12 \times 10^6$ cells per 15 $cm^2$ dish. The following day, the cells were transiently transfected using Lipofectamine (Invitrogen) with either a control CMV vector or the GPR35 containing vector. Both the CMV containing vector and the GPR35 containing vector additionally contain HA and V5 epitope tags. After four hours of incubation in the transfection mix, the cells were returned to their growth media. The next day, the cells were detached from the dish using trypsin-EDTA, then replated at $3 \times 10^5$ cells per well in a four well chamber slide. They were allowed to adhere overnight. The cells were then fixed onto the slide using 4% formaldehyde, followed by permeabilization of the cells. Cells were permeabilized using 0.1% Triton X-100 in PBSCM (PBS with 1 mM calcium and 2 mM magnesium). After blocking in a solution containing 2% BSA in PBSCM with 0.1% Triton X-100 (to get rid of the background), the primary antibody was allowed to adhere for one hour in blocking buffer (pre-immune antibody or AP-anti-GPR35 antibody, and HA antibody). After three washes, the secondary antibody (rabbit anti-chicken Alexa 555 for the GPR35 pre-immune and AP antibodies, goat anti-mouse Alexa 488 for the HA antibody and DAPI) was allowed to adhere for thirty minutes. After three washes, FluoroSave (Calbiochem-Novabiochem, San Diego, Calif.), was added to fix the coverslip onto the slide. Visualization was then done under the microscope using fluorescence filters.

Figure 7:
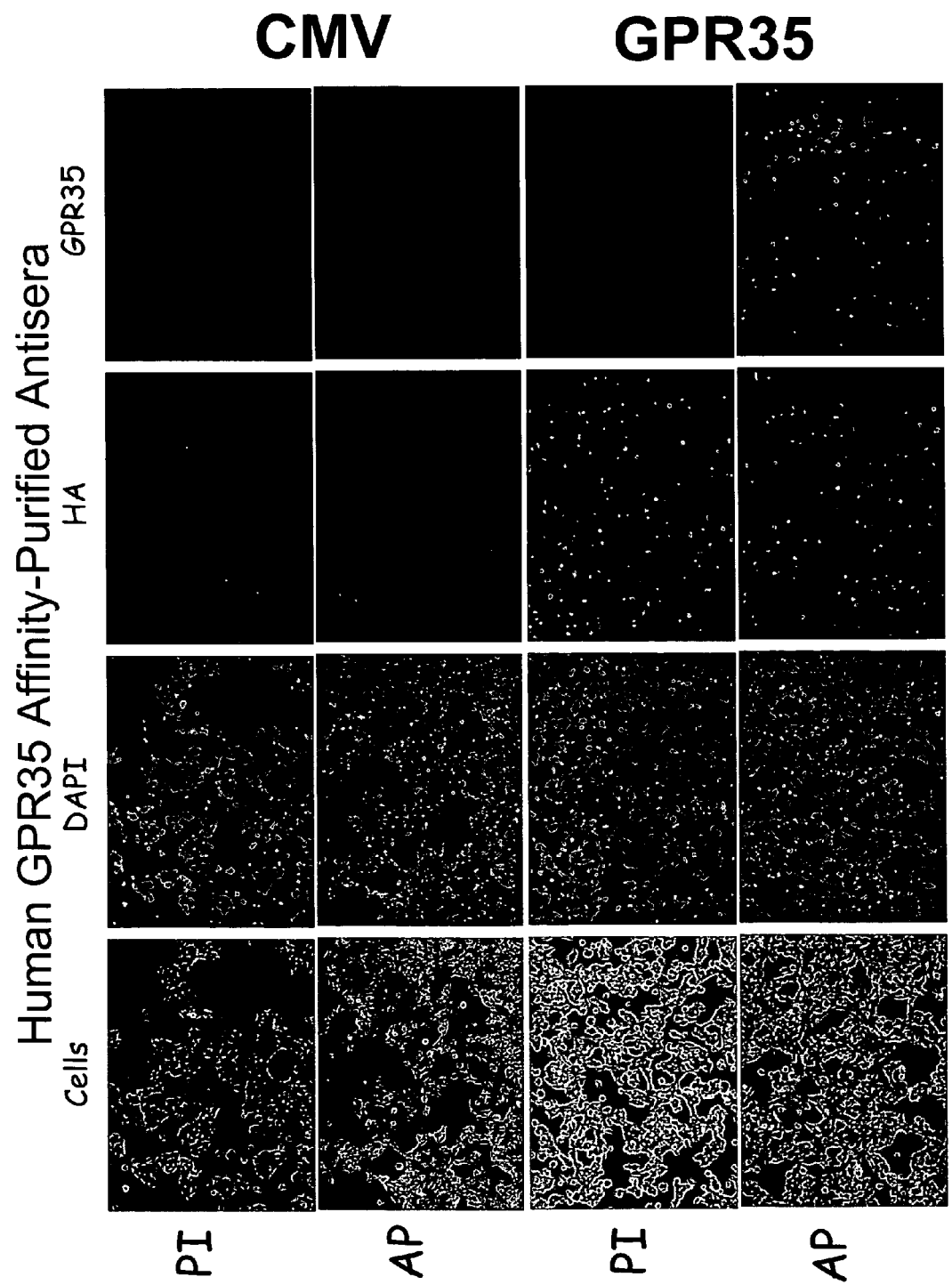
FIG. 7 shows staining of HEK293 cells expressing a control CMV vector or a GPR35 containing vector. PI indicates pre-immune sera staining and AP is affinity purified antisera staining. The column labeled cells shows what the cells looked like under the microscope, the column labeled DAPI shows nuclei staining of the cells, the column labeled HA shows detection of the HA tag, and the column labeled GPR35 shows detection of the GPR35 polypeptide.

As seen in FIG. 7, the column marked cells shows what the cells looked like under the microscope, the column marked DAPI shows the nuclei of the cells, the column marked HA shows detection of the HA tag (i.e. that GPR35 was successfully transfected into the cells since it was HA tagged), and the column marked GPR35 shows that the antibody recognizes GPR35. The rows marked PI indicate that pre-immune sera was used and so any signal is due to background. The rows marked AP indicate that affinity-purified antibody was used and so the signal is from the antibody binding. The first two rows were transfected with the CMV control vector and the last two rows were transfected with the GPR35 containing vector.

Example 8

Finding A Selective GPR35 Agonist

In this example, a compound is identified from a library and tested whether it is a selective agonist of mouse GPR35 in a melanophore assay. In addition, the compound can be tested as to whether it is a selective agonist of human GPR35 in an IP3 assay in G-alpha 16 transfected COS-7 cells.

1. Melanophore Technology

Melanophores are skin cells found in lower vertebrates. They contain pigmented organelles termed melanosomes. Melanophores are able to redistribute these melanosomes along a microtubule network upon G-protein coupled receptor (GPCR) activation. The result of this pigment movement is an apparent lightening or darkening of the cells. In melanophores, the decreased levels of intracellular cAMP that result from activation of a Gi-coupled receptor cause melanosomes to migrate to the center of the cell, resulting in a dramatic lightening in color. If cAMP levels are then raised, following activation of a Gs-coupled receptor, the melanosomes are re-dispersed and the cells appear dark again. The increased levels of diacylglycerol that result from activation of Gq-coupled receptors can also induce this re-dispersion. In addition, the technology is also suited to the study of certain receptor tyrosine kinases. The response of the melanophores takes place within minutes of receptor activation and results in a simple, robust color change. The response can be easily detected using a conventional absorbance microplate reader or a modest video imaging system. Unlike other skin cells, the melanophores derive from the neural crest and appear to express a full complement of signaling proteins. In particular, the cells express an extremely wide range of G-proteins and so are able to functionally express almost all GPCRs.

Melanophores can be utilized to identify compounds, including natural ligands, which bind to and/or activate GPCRs. This method can be conducted by introducing test cells of a pigment cell line capable of dispersing or aggregating their pigment in response to a specific stimulus and expressing an exogenous clone coding for the GPCR. An initial state of pigment disposition can be set using, for example, using melatonin, MSH or light. The test cells are then contacted with chemical compounds, and it is determined whether the pigment disposition in the cells changed from the initial state of pigment disposition. Dispersion of pigments cells due to the candidate compound, including but not limited to a ligand, coupling to the GPCR will appear dark on a petri dish, while aggregation of pigments cells will appear light.

Materials and methods followed are according to the disclosure of U.S. Pat. No. 5,462,856 and U.S. Pat. No. 6,051,386. These patent disclosures are hereby incorporated by reference in their entirety.

Melanophores are transfected by electroporation with a plasmid which contains the coding sequence of mouse GPR35. The cells are plated in 96-well plates. 48 hours post-transfection, half of the cells on each plate are treated with 10 nM melatonin. Melatonin activates an endogenous Gi-coupled receptor in the melanophores and causes them to aggregate their pigment. The remaining half of the cells are transferred to serum-free medium 0.7×L-15 (Gibco). After one hour, the cells in serum-free media remain in a pigment-dispersed state while the melatonin-treated cells are in a pigment-aggregated state. At this point, the cells are treated with different compounds from a proprietary compound library containing 140,000-150,000 organic small molecule compounds. If GPR35 binds to the compound, the melanophores would be expected to undergo a color change in response to the compound. Since the receptor can couple to Gi, the pigment-dispersed cells would be expected to undergo a dose-dependent pigment aggregation.

2. IP3 Assay of GPR35 Expressed in G16 Transfected COS-7 Cells

Intracellular IP3 accumulation assays are performed using either COS7 cells transiently transfected with expression plasmids for both GPR35 and promiscuous G protein Galpha16, or alternatively HEK293 cells stably expressing Galpha16 and transiently transfected with GPR35 expression plasmid. DNAs used in the transfections for this assay can be GPR35 and GPR35b cDNAs cloned into mammalian expression vector pCMV (designated pCMV-GPR35) and Galpha16 cDNA cloned into an expression vector pcDNA3.1(+) (Invitrogen) (designated pcDNA-G16). The sequence of G alpha16 can be found in Amatruda et al., *Proc. Natl. Acad. Sci. U.S.A.* 13:5587-5591 (1991)). Human Galpha16 cDNA is amplified with Taq polymerase and ligated into expression vector pcDNA3.1/V5-His-TOPO. Orientation of the insert is checked by restriction digest.

Transfections are performed using Lipofectamine transfection reagent (Invitrogen) and following manufacturer's recommendations. Briefly, on day 1, cells are plated on 15 cm diameter cell culture plates at densities $5 \times 10^6$ cells/plate for COS7 cells or $15 \times 10^6$ cells/plate for HEK293 cells. On the following day a DNA/Lipofectamine mixture is prepared for each plate as follows: 12 µl of DNA (6 µg of pCMV-GPR35 combined with 6 µg of pcDNA-G16 for COS7 cells, or 12 µg of pCMV-GPR35 for HEK293 cells) in 300 µl of OPTI-MEM (Gibco) is gently mixed with 60 µl of Lipofectamine reagent in 300 µl of OPTI-MEM and the resulting solution is incubated for 15-30 minutes at room temperature. Cells are washed once with 15 ml of PBS, and 13 ml of OPTI-MEM is added to the plates. DNA-Lipofectamine mixture is then gently added to the plate and mixed with OPTI-MEM. The cells are then incubated for 4 hours at 37° C. in a humidified atmosphere containing 5% $CO_2$. Transfection reagent is then removed and replaced with regular cell media and cells are incubated at 37° C./5% $CO_2$ overnight. On day 3, cells are harvested from the plate by incubation with 0.25% trypsin and replated in regular cell media into 96 well plates coated with poly-D-lysine ($4 \times 10^4$ cells per well for COS7 cells or $5.5 \times 10^4$ cells per well for HEK293 cells in 100 µl of regular growth media).

After incubation for 5-6 hours at 37° C./5% $CO_2$, regular growth media is carefully removed from wells and replaced with 100 µl of inositol-free/serum-free DMEM (ICN Biomedicals) containing 0.4 µCi of [$^3$H]-myo-inositol (Perkin-Elmer). Cells are incubated overnight at 37° C. with 5% $CO_2$. On day 4, [$^3$H]-myo-inositol-containing labeling media is removed and replaced with 100 µl of inositol-free/serum-free DMEM containing 10 µM parglyline (Sigma), 10 mM lithium chloride (Sigma) and various concentrations of the compound(s) selected from the library or other tested compounds. Cells are incubated for 2-3 hours at 37° C./5% $CO_2$. Compound containing solution is then carefully removed and 160 µl per well of ice cold 0.1M formic acid is added to the cells. The cells are lysed by incubating plates at −80° C. for at least 1 hour. Separation of $IP_3$ from cell lysates is performed using chromatography on AG1-X8 formate resin (Bio-Rad). 400 µl of formate resin slurry (0.1 g of resin in 1 ml of water) is added per each well of Multiscreen filter plate (Millipore). Water is drained from the wells and resin is then washed with 200 µl of water using Millipore filtration unit. Plates with lysed cells are thawed and lysates are transferred into Multiscreen filter plate, containing formate resin. Plates are incubated for 10 minutes at room temperature and lysates are then drained from filter plates with filtration unit. Plates are washed four times with water (200 µl/well) and thoroughly drained. Elution buffer is then added to the resin (180 µl/well) and plates are incubated for 5 minutes at room temperature. Eluents are drained into 96 well collection plates using vacuum manifold, transferred into scintillation vials containing 5 ml of Optiphase HiSafe3 scintillation cocktail (Perkin Elmer) and counted on Wallac Scintillation Counter. Alternatively, 50-60 µl of eluents are transferred into Unifilter plates (Whatman) with the sealed bottoms, which are then dried for 24-48 hours at 45° C. 50 µl per well of Optiphase HiSafe3 scintillation cocktail is added to the dried filter plates and plates are then counted on Wallac Microbeta Counter.

Example 9

Use of a GPR35 Agonist in the Oral Glucose Tolerance Test

In this example, the effect of a GPR35 agonist on plasma glucose after oral glucose administration is tested.

Male C57bl/6 mice at age 67 days are fasted for 18 hours and randomly grouped (n=6) to receive a GPR35 agonist at various doses, or vehicle (PET which contains 80% PEG, 10% Tween80, and 10% Ethanol). The GPR35 agonist is delivered orally via a gavage needle (p.o. volume at 100 µl). Thirty minutes after administration of candidate compound or vehicle, mice are administered orally with dextrose at 3 g/kg dose. Levels of blood glucose are determined at various time points using Glucometer Elite XL (Bayer).

Glucose tolerance is also tested using i.p. delivery of glucose. In this experiment 68 day old male C57Bl/6 mice are treated with the GPR35 agonist at 100 mg/kg or with PET vehicle after an 18 hour fasting. Thirty minutes after administration of candidate compound or vehicle, mice are administered i.p. with dextrose at 2 g/kg dose. Levels of blood glucose are determined at various time points using Glucometer Elite XL (Bayer).

Correlation between in vitro potency at the GPR35 receptor and in vivo improvement in oral glucose tolerance seen with GPR35 agonists tested in this assay indicate that the improved glucose tolerance seen with these compounds is due to activation of GPR35.

Example 10

Insulin-Stimulated Glucose Uptake in 3T3-L1 Adipocytes

In this example, the effect of the GPR35 agonist on insulin-stimulated glucose uptake in adipocytes is tested using a $^3$H-2-deoxyglucose uptake assay.

Experiment 1:

Briefly, 3T3-L1 cells are first differentiated into adipoctyes using a standard protocol (Patel and Lane, *Proc. Natl. Acad. Sci. U.S.A.* 96:1279-1284 (1999). Cells are then stimulated for three hours with serum-free medium containing either vehicle or 5 µM of the GPR35 agonist. Cells are then washed twice in Krebs-Ringer phosphate buffer and incubated in Krebs-Ringer phosphate buffer for 20 minutes in the presence or absence of 10 nM insulin. 2-deoxyglucose transport is measured by adding 0.05 mM (0.5 µCi/mol) $^3$H-2-deoxyglucose and 0.05 mM cold 2-deoxyglucose to the cells for 5 minutes at 37° C. To terminate the transport reaction, the cells are washed three times with ice-cold PBS and solubilized in 1% Triton-X. The level of radioactivity in the lysates is determined by scintillation counting.

Experiment 2:

As described above, mouse 3T3-L-1 cells are differentiated using the standard protocol. Cells are grown for 2 days until confluent and then a cocktail containing insulin, IBMX and dexmethosone are added to induce the cells. After 3 to 4 days of induction, the cells are grown in insulin only medium for 2 days, and then shifted to regular medium for 2 days.

For the glucose uptake assay, the differentiated 3T3-L-1 cells are treated with vehicle or 3 µM of the GPR35 agonist for 3 hours in serum free medium. After drug treatment, the medium is removed and the cells are washed with fresh Krebs-Ringer phosphate buffer twice and treated with insulin for 20 minutes at various concentrations. After 20 minutes, the glucose uptake assay is performed as described above. Briefly, 2-deoxyglucose transport is measured by adding 0.05 mM (0.5 µCi/mol) $^3$H-2-deoxyglucose and 0.05 mM cold 2-deoxyglucose to the cells for 5 minutes at 37° C. To terminate the transport reaction, the cells are washed three times with ice-cold PBS and solubilized in 1% Triton-X. The level of radioactivity in the lysates is determined by scintillation counting.

Example 11

GPR35 Agonist May Decrease Free Fatty Acid Levels in Mice

In this example, the effect a GPR35 agonist on free fatty acid (FFA) levels in C57 or DB/DB diabetic mice is tested.

Experiment 1 in C57 Mice:

The effect of a GPR35 agonist on FFA levels in C57 mice is tested using the following assay.

Male C57/B16 mice (8-10 weeks old; ~23 g) are dosed with vehicle (40% Hydroxypropyl-β-cyclodextrin; HPBCD) or drug via perenteral (PO) injection at the desired concentration in a volume of 10 mL/kg. At the desired time (for example, 30 minutes) the mice are euthanized via $CO_2$ asphyxiation and ~300 µl of blood is immediately collected by cardiac puncture. The blood is transferred to a Culex vial and capped on ice. The blood is centrifuged on a table top centrifuge (4000 rpm at 4° C. for 10 minutes). Serum is collected in a new microfuge tube and re-centrifuged (4000 rpm at 4° C. for 10 minutes). Next 5 µl of this sample is transferred to a well of a 96-well plate for the non-esterified fatty-acid (NEFA) assay. The NEFA assay is done as per manufacturer suggested protocol (NEFA-C kit from Waco Chemicals USA, Richmond, Va.). Statistical analysis include one way ANOVA analysis and Dunnett's test.

Experiment 2 in DB/DB Mice (Dose Response 1)

In this example, the effect of a GPR35 agonist on free fatty acid (FFA) levels in DB/DB diabetic mice is tested using the following assay.

Male DB/DB mice (12 weeks old; ~50 g) are dosed with vehicle (PEG400) or drug via perenteral (PO) injection at the desired concentration in a volume of 10 mL/kg, the treatments are 3 mg/kg, 10 mg/kg, and 30 mg/kg respectively. As a control, niacin 30 mg/kg is included in the first experiment. At the desired time (for example, 4 hours) the mice are euthanized via $CO_2$ asphyxiation and ~300 µl of blood is immediately collected by cardiac puncture. The blood is transferred to a Culex vial and capped on ice. The blood is centrifuged on a table top centrifuge (4000 rpm at 4° C. for 10 minutes). Serum is collected in a new microfuge tube and re-centrifuged (4000 rpm at 4° C. for 10 minutes). Next 5 µl of this sample is transferred to a well of a 96-well plate for the non-esterified fatty-acid (NEFA) assay. The NEFA assay is done as per manufacturer suggested protocol (NEFA-C kit from Waco Chemicals USA, Richmond, Va.). Statistical analysis include one way ANOVA analysis and Dunnett's test.

Experiment 3 in DB/DB Mice (Dose Response II)

In this example, the effect of a GPR35 agonist on free fatty acid (FFA) levels in DB/DB mice is tested using the following assay.

Male DB/DB mice (12 weeks old; ~50 g) are dosed with vehicle (PEG400) or drug via perenteral (PO) injection at the desired concentration in a volume of 10 mL/kg, the treatments are 0.03 mg/kg, 0.3 mg/kg, 3 mg/kg, and 30 mg/kg respectively. At the desired time (for example, 4 hours) the mice are euthanized via $CO_2$ asphyxiation and ~300 µl of blood is immediately collected by cardiac puncture. The blood is transferred to a Culex vial and capped on ice. The blood is centrifuged on a table top centrifuge (4000 rpm at 4° C. for 10 minutes). Serum is collected in a new microfuge tube and re-centrifuged (4000 rpm at 4° C. for 10 minutes). Next 5 µl of this sample is transferred to a well of a 96-well plate for the non-esterified fatty-acid (NEFA) assay. The NEFA assay is done as per manufacturer suggested protocol (NEFA-C kit from Waco Chemicals USA, Richmond, Va.). Statistical analysis include one way ANOVA analysis and Dunnett's test.

Experiment 4 in DB/DB Mice (Time Course)

In this example, the effect of a GPR35 agonist on free fatty acid (FFA) levels in DB/DB mice is tested using the following assay.

Male DB/DB mice (12 weeks old; ~50 g) are dosed with vehicle (PEG400) or drug via perenteral (PO) injection at the desired concentration in a volume of 10 mL/kg (the treatments are 3 mg/kg). At the desired time (time 0, 30 min, 60 min, 2 hours, 4 hours, and 8 hours respectively) the mice are euthanized via $CO_2$ asphyxiation and ~300 µl of blood is immediately collected by cardiac puncture. The blood is transferred to a Culex vial and capped on ice. The blood is centrifuged on a table top centrifuge (4000 rpm at 4° C. for 10 minutes). Serum is collected in a new microfuge tube and re-centrifuged (4000 rpm at 4° C. for 10 minutes). Next 5 µl of this sample is transferred to a well of a 96-well plate for the non-esterified fatty-acid (NEFA) assay. The NEFA assay is done as per manufacturer suggested protocol (NEFA-C kit from Waco Chemicals USA, Richmond, Va.).

Example 12

TaqMan Analysis of Mouse GPR35 Expression in 3T3-L1 Adipocytes

Figure 8:
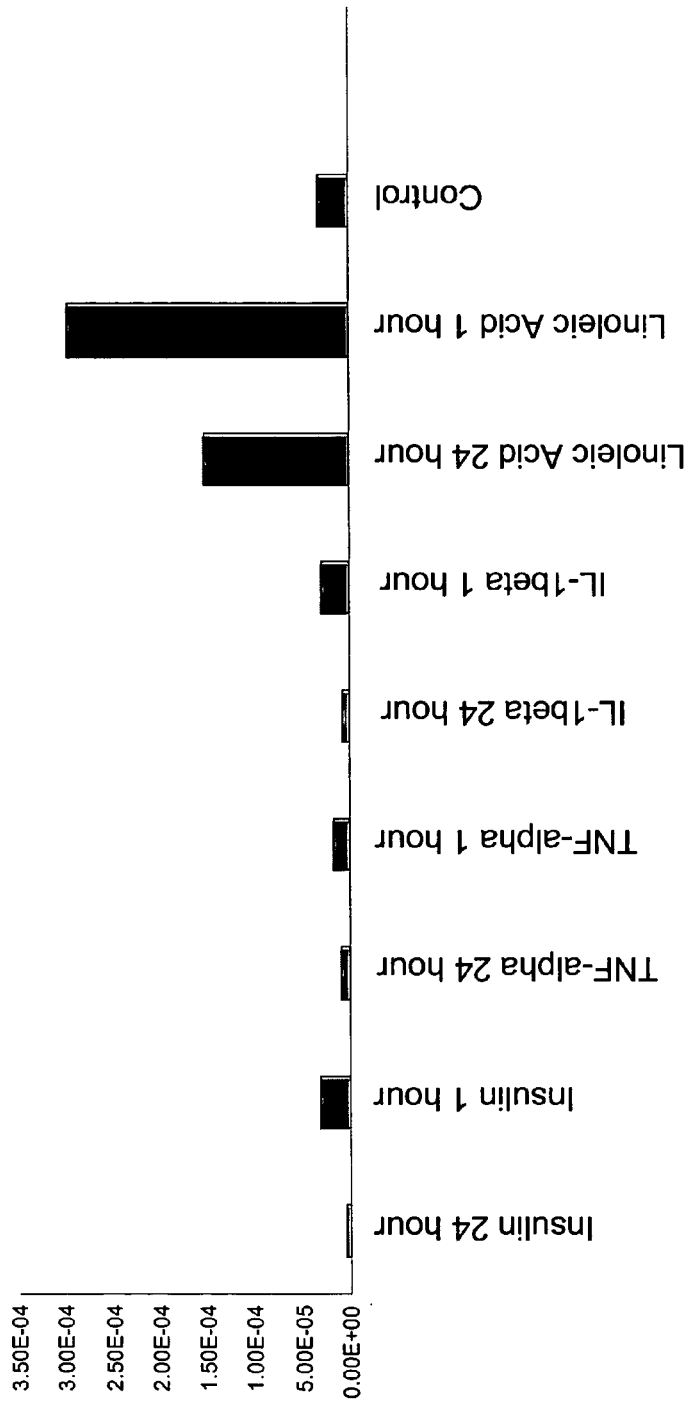
FIG. 8 shows TaqMan analysis of the level of mouse GPR35 expression in 3T3-L1 adipocytes after various treatments.

This example showed an increase in GPR35 expression in 3T3-L1 adipocytes after certain treatments, such as treatment with linoleic acid (see FIG. 8). In an initial experiment by the Applicants, the expression of GPR35 was analyzed daily in 3T3-L1 adipocytes which had undergone differentiation for 1 to 11 days. A significant increase in GPR35 expression was seen late in the time course (days 9-11) coinciding with the induction of known terminally differentiated fat cell genes (e.g. resistin) (data not shown).

GPR35 expression in 3T3-L1 adipocytes was then analyzed after certain treatments, such as treatment with linoleic acid. Briefly, 3T3-L1 cells were differentiated into adipocytes using a standardized protocol found in Patel Y M, Lane M D. (Role of calpain in adipocyte differentiation. Proc. Natl. Acad. Sci. USA 96:1279-1284, 1999). Cells were then treated for 1 and 24 hours in serum free media containing either 50 nM insulin (Sigma Cat # I-1882), 10 µM Linoleic Acid (Cal-biochem Cat # 436305 lot #B52793), 50 pg/ml IL-1Beta (R&D Systems Cat # 401-ML lot #BN034012), 0.5 ng/mL TNF-alpha (R&D Systems Cat# 410-MT lot # CS083051). Control was untreated 3T3-L1 adipocytes at time 0. RNA was then isolated using Trizol method (Invitrogen Cat # 15596-018). cDNA was made using Biorad iScript cDNA Synthesis Kit.

A 1× TaqMan supermix was made in a 5 mL polypropylene tube. Forward and Reverse primers were added to give a 300 nM final concentration; appropriate amount of probe was added to give a final concentration of 200 nM. Total volume per well was 20 µL. 2 µL was cDNA, while the other 18 µL was TaqMan supermix and nuclease-free water. The sequence for primers and the probe were:

5'Primer: ATGCAGGAGGGTGGCTTCT (SEQ ID NO: 23)
3'Primer: AGAAGGCAGTGGTGCTGAAATT (SEQ ID NO: 24)
Probe: 6FAM-CTTCAGCAGCCAAACCCGGCG-TAMRA (SEQ ID NO: 25)
Primers were ordered from Proligo and probe was synthesized by ABI.

The thermo cycler conditions used were: (1) initial steps: hold for 2 minutes at 50° C., then hold for 10 minutes at 95° C. (2) cycling: 40 cycles, each with melting for 15 seconds at 95° C. and anneal/extending for 1 minute at 60° C.

As shown in FIG. 8, GPR35 expression in 3T3-L1 adipocytes was significantly increased by linoleic acid treatment.

Example 13

GPR35 Agonist Inhibition of cAMP in 3T3-L1 Adipocvtes

This experiment determines inhibition of cAMP in 3T3-L1 adipocytes after treatment with increasing amounts of a GPR35 agonist. Inhibition of cAMP indicates an anti-lipolytic role for GPR35. Briefly, a Flash Plate™ Adenylyl Cyclase kit (New England Nuclear; Cat. No. SMP004C without IBMX) designed for cell-based assays can be modified for use with crude plasma membranes. The Flash Plate wells contain a scintillant coating which also contains a specific antibody recognizing cAMP. The cAMP generated in the wells can be quantitated by a direct competition for binding of radioactive cAMP tracer to the cAMP antibody. The following serves as a brief protocol for the measurement of changes in cAMP levels in whole cells that express a receptor.

3T3-L1 Adipocytes (ATCC Cat #CL-173) are differentiated according to a standard protocol (Patel Y M, Lane M D., Proc. Natl. Acad. Sci. USA 96:1279-1284, 1999) and cells are harvested approximately 8 days post differentiation. Media is carefully aspirated off and discarded. 10 ml of PBS is gently added to each dish of cells followed by careful aspiration. 1 ml of Sigma cell dissociation buffer and 3 ml of PBS are added to each plate. Cells are pipetted off the plate and the cell suspension is collected into a 50 ml conical centrifuge tube. Cells are then centrifuged at room temperature at 1,100 rpm for 5 minutes. The cell pellet is carefully re-suspended into an appropriate volume of PBS (about 3 ml/plate). The cells are then counted using a hemocytometer and additional PBS is added to give the appropriate number of cells (with a final volume of about 50 μl/well).

cAMP standards and Detection Buffer (comprising 2 μCi of tracer [$^{125}$I] cAMP (100 μl) to 10 ml Detection Buffer) is prepared and maintained in accordance with the manufacturer's instructions. Assay Buffer (50% PBS:50% Stimulation buffer with 1 μM Isoperteranol (ISO)) is prepared fresh for screening and contained 200 μl of PBS:Stimulation Buffer, 1 μl of candidate compound (50 μM final assay concentration) done in dose dependent manner and DMSO is added. Assay buffer is stored on ice until utilized. Basal level and DMSO (vehicle) treatments are comprised of Assay Buffer without Isoperteranol. The assay, carried out in a 96-well plate, is initiated by addition of 50 μl of cAMP standards to appropriate wells followed by addition of 50 μl of PBSA to wells H11 and H12. 50 μl of PBS:Stimulation Buffer and compound is added to appropriate wells. The cells (50 μl) are then added to the wells and incubated for 60 minutes at room temperature. 100 μl of Detection Mix containing tracer cAMP is then added to the wells. Plates are then incubated an additional 2 hours followed by counting in a Wallac MicroBeta scintillation counter. Values of cAMP/well are then extrapolated from a standard cAMP curve which is contained within each assay plate.

Example 14

Assays for Determination of GPCR Activation

A variety of approaches are available for assessment of activation of human GPCRs. The following are illustrative; those of ordinary skill in the art are credited with the ability to determine those techniques that are preferentially beneficial for the needs of the artisan.

1. Membrane Binding Assays: [$^{35}$S]GTPγS Assay

When a G protein-coupled receptor is in its active state, either as a result of ligand binding or constitutive activation, the receptor couples to a G protein and stimulates the release of GDP and subsequent binding of GTP to the G protein. The alpha subunit of the G protein-receptor complex acts as a GTPase and slowly hydrolyzes the GTP to GDP, at which point the receptor normally is deactivated. Activated receptors continue to exchange GDP for GTP. The non-hydrolyzable GTP analog, [$^{35}$S]GTPγS, can be utilized to demonstrate enhanced binding of [$^{35}$S]GTPγS to membranes expressing activated receptors. The advantage of using [$^{35}$S]GTPγS binding to measure activation is that: (a) it is generically applicable to all G protein-coupled receptors; (b) it is proximal at the membrane surface making it less likely to pick-up molecules which affect the intracellular cascade.

The assay utilizes the ability of G protein coupled receptors to stimulate [$^{35}$S]GTPγS binding to membranes expressing the relevant receptors. The assay can, therefore, be used in the direct identification method to screen candidate compounds to endogenous GPCRs and non-endogenous, constitutively activated GPCRs. The assay is generic and has application to drug discovery at all G protein-coupled receptors.

The [$^{35}$S]GTPγS assay is incubated in 20 mM HEPES and between 1 and about 20 nM MgCl$_2$ (this amount can be adjusted for optimization of results, although 20 mM is preferred) pH 7.4, binding buffer with between about 0.3 and about 1.2 nM [$^{35}$S]GTPγS (this amount can be adjusted for optimization of results, although 1.2 is preferred) and 12.5 to 75 μg membrane protein (e.g, 293 cells expressing the GPR35; this amount can be adjusted for optimization) and 10 μM GDP (this amount can be changed for optimization) for 1 hour. Wheatgerm agglutinin beads (25 μl; Amersham) are then added and the mixture incubated for another 30 minutes at room temperature. The tubes are then centrifuged at 1500×g for 5 minutes at room temperature and then counted in a scintillation counter.

2. Adenylyl Cyclase

A Flash Plate™ Adenylyl Cyclase kit (New England Nuclear; Cat. No. SMP004A) designed for cell-based assays can be modified for use with crude plasma membranes. The Flash Plate wells can contain a scintillant coating which also contains a specific antibody recognizing cAMP. The cAMP generated in the wells can be quantitated by a direct competition for binding of radioactive cAMP tracer to the cAMP antibody. The following serves as a brief protocol for the measurement of changes in cAMP levels in whole cells that express a receptor.

Transfected cells are harvested approximately twenty four hours after transient transfection. Media is carefully aspirated off and discarded. 10 ml of PBS is gently added to each dish of cells followed by careful aspiration. 1 ml of Sigma cell dissociation buffer and 3 ml of PBS are added to each plate. Cells are pipetted off the plate and the cell suspension is collected into a 50 ml conical centrifuge tube. Cells are then centrifuged at room temperature at 1,100 rpm for 5 minutes. The cell pellet is carefully re-suspended into an appropriate volume of PBS (about 3 ml/plate). The cells are then counted using a hemocytometer and additional PBS is added to give the appropriate number of cells (with a final volume of about 50 μl/well).

cAMP standards and Detection Buffer (comprising 1 μCi of tracer [$^{125}$I] cAMP (50 μl) to 11 ml Detection Buffer) is prepared and maintained in accordance with the manufacturer's instructions. Assay Buffer is prepared fresh for screening and contains 50 μl of Stimulation Buffer, 3 μl of candidate compound (12 μM final assay concentration) and 50 μl cells. Assay Buffer is stored on ice until utilized. The assay, preferably carried out, for example, in a 96-well plate, is initiated by addition of 50 μl of cAMP standards to appropriate wells followed by addition of 50 μl of PBSA to wells H11 and H12. 50 μl of Stimulation Buffer is added to all wells. DMSO (or selected candidate compounds) is added to appropriate wells using a pin tool capable of dispensing 3 μl of compound solution, with a final assay concentration of 12 μM candidate compound and 100 μl total assay volume. The cells are then added to the wells and incubated for 60 minutes at room temperature. 100 μl of Detection Mix containing tracer cAMP is then added to the wells. Plates are then incubated additional 2 hours followed by counting in a Wallac MicroBeta scintillation counter. Values of cAMP/well are then extrapolated from a standard cAMP curve which is contained within each assay plate.

3. Cell-Based cAMP for Gi Coupled Target GPCRs

TSHR is a Gs coupled GPCR that causes the accumulation of cAMP upon activation. TSHR can be constitutively activated by mutating amino acid residue 623 (i.e., changing an alanine residue to an isoleucine residue). A Gi coupled receptor is expected to inhibit adenylyl cyclase, and, therefore, decrease the level of cAMP production, which can make assessment of cAMP levels challenging. An effective technique for measuring the decrease in production of cAMP as an indication of activation of a Gi coupled receptor can be accomplished by co-transfecting, non-endogenous, constitutively activated TSHR (TSHR-A6231) (or an endogenous, constitutively active Gs coupled receptor) as a "signal enhancer" with a Gi linked target GPCR to establish a baseline level of cAMP. Upon creating an endogenous or non-endogenous version of the Gi coupled receptor, the target GPCR is then co-transfected with the signal enhancer, and it is this material that can be used for screening. In some embodiments, this approach is preferably used in the direct identification of candidate compounds against Gi coupled receptors. It is noted that for a Gi coupled GPCR, when this approach is used, an inverse agonist of the target GPCR will increase the cAMP signal and an agonist will decrease the cAMP signal.

On day one, $2\times10^4$ 293 cells/well are plated out. On day two, two reaction tubes are prepared (the proportions to follow for each tube are per plate): tube A is prepared by mixing 2 µg DNA of each receptor transfected into the mammalian cells, for a total of 4 µg DNA (e.g., pCMV vector; pCMV vector with mutated THSR (TSHR-A6231); TSHR-A6231 and GPCR, etc.) in 1.2 ml serum free DMEM (Irvine Scientific, Irvine, Calif.); tube B is prepared by mixing 120 µl lipofectamine (Gibco BRL) in 1.2 ml serum free DMEM. Tubes A and B are then admixed by inversions (several times), followed by incubation at room temperature for 30-45 minutes. The admixture is referred to as the "transfection mixture". Plated 293 cells are washed with 1×PBS, followed by addition of 10 ml serum free DMEM. 2.4 ml of the transfection mixture is then added to the cells, followed by incubation for 4 hours at 37° C./5% $CO_2$. The transfection mixture is then removed by aspiration, followed by the addition of 25 ml of DMEM/10% Fetal Bovine Serum. Cells are then incubated at 37° C./5% $CO_2$. After 24 hours incubation, cells are harvested and utilized for analysis.

A Flash Plate™ Adenylyl Cyclase kit (New England Nuclear; Cat. No. SMP004A) is designed for cell-based assays, but can be modified for use with crude plasma membranes depending on the need of the skilled artisan. The Flash Plate wells contain a scintillant coating which also contains a specific antibody recognizing cAMP. The cAMP generated in the wells can be quantitated by a direct competition for binding of radioactive cAMP tracer to the cAMP antibody. The following serves as a brief protocol for the measurement of changes in cAMP levels in whole cells that express a receptor of interest.

Transfected cells are harvested approximately twenty four hours after transient transfection. Media is carefully aspirated off and discarded. 10 ml of PBS is gently added to each dish of cells followed by careful aspiration. 1 ml of Sigma cell dissociation buffer and 3 ml of PBS is added to each plate. Cells are pipetted off the plate and the cell suspension is collected into a 50 ml conical centrifuge tube. Cells are then centrifuged at room temperature at 1,100 rpm for 5 minutes. The cell pellet is carefully re-suspended into an appropriate volume of PBS (about 3 ml/plate). The cells are then counted using a hemocytometer and additional PBS is added to give the appropriate number of cells (with a final volume of about 50 µl/well).

cAMP standards and Detection Buffer (comprising 1 µCi of tracer [$^{125}$I] cAMP (50 µl) to 11 ml Detection Buffer) is prepared and maintained in accordance with the manufacturer's instructions. Assay Buffer should be prepared fresh for screening and contain 50 µl of Stimulation Buffer, 3 µl of candidate compound (12 µM final assay concentration) and 50 µl cells. Assay Buffer can be stored on ice until utilized. The assay can be initiated by addition of 50 µl of cAMP standards to appropriate wells followed by addition of 50 µl of PBSA to wells H-11 and H12. Fifty µl of Stimulation Buffer is added to all wells. Selected compounds (e.g., TSH) are added to appropriate wells using a pin tool capable of dispensing 3 µl of compound solution, with a final assay concentration of 12 µM candidate compound and 100 µl total assay volume. The cells are then added to the wells and incubated for 60 minutes at room temperature. 100 µl of Detection Mix containing tracer cAMP is then added to the wells. Plates are then incubated additional 2 hours followed by counting in a Wallac MicroBeta scintillation counter. Values of cAMP/well are extrapolated from a standard cAMP curve which is contained within each assay plate.

4. Reporter-Based Assays a. CRE-LUC Reporter Assay (Gs-Associated Receptors)

293 or 293T cells are plated-out on 96 well plates at a density of $2\times10^4$ cells per well and are transfected using Lipofectamine Reagent (BRL) the following day according to manufacturer instructions. A DNA/lipid mixture is prepared for each 6-well transfection as follows: 260 ng of plasmid DNA in 100 µl of DMEM is gently mixed with 2 µl of lipid in 100 µl of DMEM (the 260 ng of plasmid DNA consists of 200 ng of a 8×CRE-Luc reporter plasmid, 50 ng of pCMV comprising endogenous receptor or non-endogenous receptor or pCMV alone, and 10 ng of a GPRS expression plasmid (GPRS in pcDNA3 (Invitrogen)). The 8×CRE-Luc reporter plasmid is prepared as follows: vector SRIF-β-gal is obtained by cloning the rat somatostatin promoter (−71/+51) at BglV-HindIII site in the pβgal-Basic Vector (Clontech). Eight (8) copies of cAMP response element are obtained by PCR from an adenovirus template AdpCF126CCRE8 (see, Suzuki et al., *Hum Gene Ther* 7:1883-1893 (1996); the disclosure of which is hereby incorporated by reference in its entirety) and cloned into the SRIF-β-gal vector at the Kpn-BglV site, resulting in the 8×CRE-β-gal reporter vector. The 8×CRE-Luc reporter plasmid is generated by replacing the beta-galactosidase gene in the 8×CRE-β-gal reporter vector with the luciferase gene obtained from the pGL3-basic vector (Promega) at the HindIII-BamHI site. Following 30 minutes incubation at room temperature, the DNA/lipid mixture is diluted with 400 µl of DMEM and 100 µl of the diluted mixture is added to each well. 100 µl of DMEM with 10% FCS are added to each well after a four hour incubation in a cell culture incubator. The following day the transfected cells are changed with 200 µl/well of DMEM with 10% FCS. Eight (8) hours later, the wells are changed to 100 µl/well of DMEM without phenol red, after one wash with PBS. Luciferase activity is measured the next day using the LucLite™ reporter gene assay kit (Packard) following manufacturer instructions and read on a 1450 MicroBeta™ scintillation and luminescence counter (Wallac).

b. AP1 Reporter Assay (Gq-Associated Receptors)

A method to detect Gq stimulation depends on the known property of Gq-dependent phospholipase C to cause the activation of genes containing AP1 elements in their promoter. A Pathdetect™ AP-1 cis-Reporting System (Stratagene, Catalogue No. 219073) can be utilized following the protocol set forth above with respect to the CREB reporter assay, except that the components of the calcium phosphate precipitate are 410 ng pAP1-Luc, 80 ng pCMV-receptor expression plasmid, and 20 ng CMV-SEAP.

c. SRF-LUC Reporter Assay (Gq-Associated Receptors)

One method to detect Gq stimulation depends on the known property of Gq-dependent phospholipase C to cause the activation of genes containing serum response factors in their promoter. A Pathdetect™ SRF-Luc-Reporting System (Stratagene) can be utilized to assay for Gq coupled activity in, for example, COS7 cells. Cells are transfected with the plasmid components of the system and the indicated expression plasmid encoding endogenous or non-endogenous GPCR using a Mammalian Transfection™ Kit (Stratagene, Catalogue #200285) according to the manufacturer's instructions. Briefly, 410 ng SRF-Luc, 80 ng pCMV-receptor expression plasmid and 20 ng CMV-SEAP (secreted alkaline phosphatase expression plasmid; alkaline phosphatase activity is measured in the media of transfected cells to control for variations in transfection efficiency between samples) are combined in a calcium phosphate precipitate as per the manufacturer's instructions. Half of the precipitate is equally distributed over 3 wells in a 96-well plate and kept on the cells in a serum free media for 24 hours. The last 5 hours the cells are incubated with, for example, 1 µM, candidate compound. Cells are then lysed and assayed for luciferase activity using a Luclite™ Kit (Packard, Cat. No. 6016911) and "Trilux 1450 Microbeta" liquid scintillation and luminescence counter (Wallac) as per the manufacturer's instructions. The data can be analyzed using GraphPad Prism™ 2.0a (GraphPad Software Inc.).

d. Intracellular IP3 Accumulation Assay (Gq-Associated Receptors)

On day 1, cells comprising the receptor of interest (endogenous or non-endogenous) can be plated onto 24 well plates, usually $1 \times 10^5$ cells/well (although his number can be optimized). On day 2 cells can be transfected by first mixing 0.25 µg DNA in 50 µl serum free DMEM/well and 2 µl lipofectamine in 50 µl serum free DMEM/well. The solutions are gently mixed and incubated for 15-30 minutes at room temperature. Cells are washed with 0.5 ml PBS and 400 µl of serum free media is mixed with the transfection media and added to the cells. The cells are then incubated for 3-4 hours at 37° C./5% $CO_2$ and then the transfection media is removed and replaced with 1 ml/well of regular growth media. On day 3 the cells are labeled with $^3$H-myo-inositol. Briefly, the media is removed and the cells are washed with 0.5 ml PBS. Then 0.5 ml inositol-free/serum free media (GIBCO BRL) is added/well with 0.25 µCi of $^3$H-myo-inositol/well and the cells are incubated for 16-18 hours overnight at 37° C./5% $CO_2$. On Day 4 the cells are washed with 0.5 ml PBS and 0.45 ml of assay medium is added containing inositol-free/serum free media, 10 µM pargyline, 10 mM lithium chloride or 0.4 ml of assay medium and 50 µl of 10× ketanserin (ket) to final concentration of 10 µM, if using a control construct containing a serotonin receptor. The cells are then incubated for 30 minutes at 37° C. The cells are then washed with 0.5 ml PBS and 200 µl of fresh/ice cold stop solution (1M KOH; 18 mM Na-borate; 3.8 mM EDTA) is added/well. The solution is kept on ice for 5-10 minutes or until cells were lysed and then neutralized by 200 µl of fresh/ice cold neutralization sol. (7.5% HCL). The lysate is then transferred into 1.5 ml eppendorf tubes and 1 ml of chloroform/methanol (1:2) is added/tube. The solution is vortexed for 15 seconds and the upper phase is applied to a Biorad AG1-X8™ anion exchange resin (100-200 mesh). Firstly, the resin is washed with water at 1:1.25 WV and 0.9 ml of upper phase is loaded onto the column. The column is washed with 10 mls of 5 mM myo-inositol and 10 ml of 5 mM Na-borate/60 mM Na-formate. The inositol tris phosphates are eluted into scintillation vials containing 10 ml of scintillation cocktail with 2 ml of 0.1 M formic acid/1 M ammonium formate. The columns are regenerated by washing with 10 ml of 0.1 M formic acid/3M ammonium formate and rinsed twice with dd $H_2O$ and stored at 4° C. in water.

Example 15

Fusion Protein Preparation a. GPCR:Gs Fusion Constuct

The design of the GPCR-G protein fusion construct can be accomplished as follows: both the 5' and 3' ends of the rat G protein Gsα (long form; Itoh, H. et al., *Proc. Natl. Acad. Sci.* 83:3776 (1986)) are engineered to include a HindIII sequence thereon. Following confirmation of the correct sequence (including the flanking HindIII sequences), the entire sequence is shuttled into pcDNA3.1(−) (Invitrogen, cat. no. V795-20) by subcloning using the HindIII restriction site of that vector. The correct orientation for the Gsα sequence is determined after subcloning into pcDNA3.1(−). The modified pcDNA3.1(−) containing the rat Gsα gene at HindIII sequence is then verified; this vector is now available as a "universal" Gsα protein vector. The pcDNA3.1(−) vector contains a variety of well-known restriction sites upstream of the HindIII site, thus beneficially providing the ability to insert, upstream of the Gs protein, the coding sequence of a receptor of interest. This same approach can be utilized to create other "universal" G protein vectors, and, of course, other commercially available or proprietary vectors known to the artisan can be utilized—the important criteria is that the sequence for the GPCR be upstream and in-frame with that of the G protein.

b. Gq (6 Amino Acid Deletion)/Gi Fusion Construct

The design of a Gq(del)/Gi fusion construct can be accomplished as follows: the N-terminal six (6) amino acids (amino acids 2 through 7, having the sequence of TLESIM (SEQ ID NO:26)) of Gαq-subunit is deleted and the C-terminal five (5) amino acids having the sequence EYNLV (SEQ ID NO:27) is replaced with the corresponding amino acids of the Gαi Protein, having the sequence DCGLF (SEQ ID NO:28). This fusion construct can be obtained by PCR using the following primers:

```
                                         (SEQ ID NO: 29)
5'-gatcAAGCTTCCATGGCGTGCTGCCTGAGCGAGGAG-3'
and
```

```
                                         (SEQ ID NO: 30)
5'-gatcGGATCCTTAGAACAGGCCGCAGTCCTTCAGGTTCAGCTGCAGGA
TGGTG-3'
``` and Plasmid 63313 which contains the mouse Gαq-wild type version with a hemagglutinin tag as template. Nucleotides in lower caps are included as spacers.

TaqPlus Precision DNA polymerase (Stratagene) can be utilized for the amplification by the following cycles, with steps 2 through 4 repeated 35 times: 95° C. for 2 min; 95° C. for 20 sec; 56° C. for 20 sec; 72° C. for 2 min; and 72° C. for 7 min. The PCR product can be cloned into pCRII-TOPO vector (Invitrogen) and sequenced using the ABI Big Dye Terminator kit (P.E. Biosystems). Inserts from a TOPO clone containing the sequence of the fusion construct can be shuttled into the expression vector pcDNA3.1(+) at the HindIII/BamHI site by a 2 step cloning process. Also see, PCT Application Number PCT/US02/05625 published as WO02068600 on 6 Sep. 2002, the disclosure of which is hereby incorporated by reference in its entirety.

Example 16

[$^{35}$S]GTPγS Assay

A. Membrane Preparation

In some embodiments membranes comprising the Target GPCR of interest for use in the identification of candidate compounds as, e.g., agonists, inverse agonists or antagonists, are prepared as follows:

a. Materials

"Membrane Scrape Buffer" is comprised of 20 mM HEPES and 10 mM EDTA, pH 7.4; "Membrane Wash Buffer" is comprised of 20 mM HEPES and 0.1 mM EDTA, pH 7.4; "Binding Buffer" is comprised of 20 mM HEPES, 100 mM NaCl, and 10 mM MgCl$_2$, pH 7.4.

b. Procedure

All materials are kept on ice throughout the procedure. Firstly, the media is aspirated from a confluent monolayer of cells, followed by rinsing with 10 ml cold PBS, followed by aspiration. Thereafter, 5 ml of Membrane Scrape Buffer is added to scrape cells; this is followed by transfer of cellular extract into 50 ml centrifuge tubes (centrifuged at 20,000 rpm for 17 minutes at 4° C.). Thereafter, the supernatant is aspirated and the pellet is resuspended in 30 ml Membrane Wash Buffer followed by centrifuge at 20,000 rpm for 17 minutes at 4° C. The supernatant is then aspirated and the pellet resuspended in Binding Buffer. This is then homogenized using a Brinkman Polytron™ homogenizer (15-20 second bursts until the all material is in suspension). This is referred to herein as "Membrane Protein".

Bradford Protein Assay

Following the homogenization, protein concentration of the membranes is determined using the Bradford Protein Assay (protein can be diluted to about 1.5 mg/ml, aliquoted and frozen (−80° C.) for later use; when frozen, protocol for use will be as follows: on the day of the assay, frozen Membrane Protein is thawed at room temperature, followed by vortex and then homogenized with a Polytron at about 12×1,000 rpm for about 5-10 seconds; it is noted that for multiple preparations, the homogenizer should be thoroughly cleaned between homogenization of different preparations).

a. Materials

Binding Buffer (as per above); Bradford Dye Reagent; Bradford Protein Standard is utilized, following manufacturer instructions (Biorad, cat. no. 500-0006).

b. Procedure

Duplicate tubes are prepared, one including the membrane, and one as a control "blank". Each tube contains 800 µl Binding Buffer. Thereafter, 10 µl of Bradford Protein Standard (1 mg/ml) is added to each tube, and 10 µl of membrane Protein is then added to just one tube (not the blank). Thereafter, 200 µl of Bradford Dye Reagent is added to each tube, followed by vortexing of each tube. After five (5) minutes, the tubes are re-vortexed and the material therein is transferred to cuvettes. The cuvettes are read using a CECIL 3041 spectrophotometer, at wavelength 595.

Identification Assay a. Materials

GDP Buffer consists of 37.5 ml Binding Buffer and 2 mg GDP (Sigma, cat. no. G-7127), followed by a series of dilutions in Binding Buffer to obtain 0.2 µM GDP (final concentration of GDP in each well is 0.1 µM GDP); each well comprising a candidate compound has a final volume of 200 µl consisting of 100 µl GDP Buffer (final concentration, 0.1 µM GDP), 50 µl Membrane Protein in Binding Buffer, and 50 µl [$^{35}$S]GTPγS (0.6 nM) in Binding Buffer (2.5 µl [$^{35}$S]GTPγS per 10 µml Binding Buffer).

b. Procedure

Candidate compounds can be screened using a 96-well plate format (these can be frozen at −80° C.). Membrane Protein (or membranes with expression vector excluding the Target GPCR, as control), are homogenized briefly until in suspension. Protein concentration is be determined using the Bradford Protein Assay set forth above. Membrane Protein (and control) is diluted to 0.25 mg/ml in Binding Buffer (final assay concentration, 12.5 µg/well). Thereafter, 100 µl GDP Buffer is added to each well of a Wallac Scintistrip™ (Wallac). A 5 µl pin-tool is used to transfer 5 µl of a candidate compound into such well (i.e., 5 µl in total assay volume of 200 µl is a 1:40 ratio such that the final screening concentration of the candidate compound is 10 µM). Again, to avoid contamination, after each transfer step the pin tool should be rinsed in three reservoirs comprising water (1×), ethanol (1×) and water (2×)—excess liquid should be shaken from the tool after each rinse and dried with paper and kimwipes. Thereafter, 50 µl of Membrane Protein is added to each well (a control well comprising membranes without the Target GPCR is also utilized), and pre-incubated for 5-10 minutes at room temperature. Thereafter, 50 µl of [$^{35}$S]GTPγS (0.6 nM) in Binding Buffer is added to each well, followed by incubation on a shaker for 60 minutes at room temperature (plates are covered with foil). The assay is then stopped by spinning of the plates at 4000 RPM for 15 minutes at 22° C. The plates are aspirated with an 8 channel manifold and sealed with plate covers. The plates are read on a Wallac 1450 using setting "Prot. #37" (as per manufacturer's instructions).

Example 17

Cyclic AMP Assay

Another assay approach for identifying candidate compounds as, e.g., agonists, inverse agonist, or antagonists, can accomplished by utilizing a cyclase-based assay. In addition to direct identification, this assay approach can be utilized as an independent approach to provide confirmation of the results from the [$^{35}$S]GTPγS approach as set forth in the above example.

A modified Flash Plate™ Adenylyl Cyclase kit (New England Nuclear; Cat. No. SMP004A) can be utilized for direct identification of candidate compounds as inverse agonists and agonists to a receptor of interest in accordance with the following protocol.

Transfected cells are harvested approximately three days after transfection. Membranes are prepared by homogenization of suspended cells in buffer containing 20 mM HEPES, pH 7.4 and 10 mM MgCl$_2$. Homogenization is performed on ice using a Brinkman Polytron™ for approximately 10 seconds. The resulting homogenate is centrifuged at 49,000×g for 15 minutes at 4° C. The resulting pellet is then resuspended in buffer containing 20 mM HEPES, pH 7.4 and 0.1 mM EDTA, homogenized for 10 seconds, followed by centrifugation at 49,000×g for 15 minutes at 4° C. The resulting pellet is then stored at −80° C. until utilized. On the day of direct identification screening, the membrane pellet is slowly thawed at room temperature, resuspended in buffer containing 20 mM HEPES, pH 7.4 and 10 mM MgCl$_2$, to yield a final protein concentration of 0.60 mg/ml (the resuspended membranes are placed on ice until use).

cAMP standards and Detection Buffer (comprising 2 µCi of tracer [$^{125}$I]cAMP (100 µl) to 11 ml Detection Buffer] are prepared and maintained in accordance with the manufacturer's instructions. Assay Buffer is prepared fresh for screening and contains 20 mM HEPES, pH 7.4, 10 mM $MgCl_2$, 20 mM phospocreatine (Sigma), 0.1 units/ml creatine phosphokinase (Sigma), 50 µM GTP (Sigma), and 0.2 mM ATP (Sigma); Assay Buffer is then stored on ice until utilized.

Candidate compounds are added to, for example, 96-well plate wells (3 µl/well; 12 µM final assay concentration), together with 40 µl Membrane Protein (30 µg/well) and 50 µl of Assay Buffer. This admixture is then incubated for 30 minutes at room temperature, with gentle shaking.

Following the incubation, 100 µl of Detection Buffer is added to each well, followed by incubation for 2-24 hours. Plates are then counted in a Wallac MicroBeta™ plate reader using "Prot. #31" (as per manufacturer's instructions).

Example 18

Fluorometric Imaging Plate Reader (FLIPR) Assay for the Measurement of Intracellular Calcium Concentration Target Receptor (experimental) and pCMV (negative control) stably transfected cells from respective clonal lines are seeded into poly-D-lysine pretreated 96-well plates (Becton-Dickinson, #356640) at $5.5 \times 10^4$ cells/well with complete culture medium (DMEM with 10% FBS, 2 mM L-glutamine, 1 mM sodium pyruvate) for assay the next day. Because GPR35 is Gi coupled, the cells comprising GPR35 can further comprise G$\alpha$15, G$\alpha$16, or the chimeric Gq/Gi alpha subunit. However, since GPR35 is also coupled to G$\alpha$12/13 (see Example 3 and FIG. 3), a promiscuous G protein such as G$\alpha$15, G$\alpha$16, or the chimeric Gq/Gi alpha subunit may not be required in order to cause a detectable calcium flux. To prepare Fluo4-AM (Molecular Probe, #F14202) incubation buffer stock, 1 mg Fluo4-AM is dissolved in 467 µl DMSO and 467 µl Pluoronic acid (Molecular Probe, #P3000) to give a 1 mM stock solution that can be stored at −20° C. for a month. Fluo4-AM is a fluorescent calcium indicator dye.

Candidate compounds are prepared in wash buffer (1×HBSS/2.5 mM Probenicid/20 mM HEPES at pH 7.4).

At the time of assay, culture medium is removed from the wells and the cells are loaded with 100 µl of 4 µM Fluo4-AM/2.5 mM Probenicid (Sigma, #P8761)/20 mM HEPES/complete medium at pH 7.4. Incubation at 37° C./5% $CO_2$ is allowed to proceed for 60 minutes.

After the 1 hour incubation, the Fluo4-AM incubation buffer is removed and the cells are washed 2× with 100 µl wash buffer. In each well is left 100 µl wash buffer. The plate is returned to the incubator at 37° C./5% $CO_2$ for 60 minutes.

FLIPR (Fluorometric Imaging Plate Reader; Molecular Device) is programmed to add 50 µl candidate compound on the 30th second and to record transient changes in intracellular calcium concentration ([Ca2+]) evoked by the candidate compound for another 150 seconds. Total fluorescence change counts are used to determine agonist activity using the FLIPR software. The instrument software normalizes the fluorescent reading to give equivalent initial readings at zero.

Although the foregoing provides a FLIPR assay for agonist activity using stably transfected cells, a person of ordinary skill in the art would readily be able to modify the assay in order to characterize antagonist activity. Said person of ordinary skill in the art would also readily appreciate that, alternatively, transiently transfected cells could be used.

Example 19

MAP Kinase Assay

MAP kinase (mitogen activated kinase) can be monitored to evaluate receptor activation. MAP kinase can be detected by several approaches. One approach is based on an evaluation of the phosphorylation state, either unphosphorylated (inactive) or phosphorylated (active). The phosphorylated protein has a slower mobility in SDS-PAGE and can therefore be compared with the unstimulated protein using Western blotting. Alternatively, antibodies specific for the phosphorylated protein are available (New England Biolabs) which can be used to detect an increase in the phosphorylated kinase. In either method, cells are stimulated with the candidate compound and then extracted with Laemmli buffer. The soluble fraction is applied to an SDS-PAGE gel and proteins are transferred electrophoretically to nitrocellulose or Immobilin. Immunoreactive bands are detected by standard Western blotting technique. Visible or chemiluminescent signals are recorded on film and can be quantified by densitometry.

Another approach is based on evaluation of the MAP kinase activity via a phosphorylation assay. Cells are stimulated with the candidate compound and a soluble extract is prepared. The extract is incubated at 30° C. for 10 minutes with gamma-$^{32}$P-ATP, an ATP regenerating system, and a specific substrate for MAP kinase such as phosphorylated heat and acid stable protein regulated by insulin, or PHAS-I. The reaction is terminated by the addition of $H_3PO_4$ and samples are transferred to ice. An aliquot is spotted onto Whatman P81 chromatography paper, which retains the phosphorylated protein. The chromatography paper is washed and counted for $^{32}$P is a liquid scintillation counter. Alternatively, the cell extract is incubated with gamma-$^{32}$P-ATP, an ATP regenerating system, and biotinylated myelin basic protein bound by streptavidin to a filter support. The myelin basic protein is a substrate for activated MAP kinase. The phosphorylation reaction is carried out for 10 minutes at 30° C. The extract can then be aspirated through the filter, which retains, the phosphorylated myelin basic protein. The filter is washed and counted for $^{32}$P by liquid scintillation counting.

Example 20

Receptor Binding Assay

In addition to the methods described herein, another means for evaluating a candidate compound is by determining binding affinities to the GPR35 receptor. This type of assay generally requires a radiolabelled ligand to the GPR35 receptor. Absent the use of known ligands for the GPR35 receptor and radiolabels thereof, compounds identified using the methods disclosed herein can be labelled with a radioisotope and used in an assay for evaluating the affinity of a candidate compound to the GPR35 receptor. Alternatively, one could try kynurenic acid which was recently reported to be a ligand for GPR35 (Wang et al., J. Biol. Chem. 281:22021-22028 (2006)).

A radiolabelled GPR35 compound such as a compound identified using the methods disclosed herein (called Compound X hereafter) can be used in a screening assay to identify/evaluate compounds. In general terms, a newly synthesized or identified compound (i.e., candidate compound) can be evaluated for its ability to reduce binding of the radiolabelled Compound X to the GPR35 receptor. Accordingly, the ability to compete with the radiolabelled Compound X for the binding to the GPR35 receptor directly correlates to the binding affinity of the candidate compound to the GPR35 receptor.

Assay Protocol for Determining Receptor Binding for GPR35:

A. GPR35 Receptor Preparation

For example, HEK293 cells (human kidney, ATCC) can be transiently or stably transfected with GPR35 as described herein. For example, 293 cells can be transiently transfected with 10 μg human GPR35 receptor and 60 μl Lipofectamine (per 15-cm dish), and grown in the dish for 24 hours (75% confluency) with a media change. Cells are removed with 10 ml/dish of Hepes-EDTA buffer (20 mM Hepes+10 mM EDTA, pH 7.4). The cells are then centrifuged in a Beckman Coulter centrifuge for 20 minutes, 17,000 rpm (JA-25.50 rotor). Subsequently, the pellet is resuspended in 20 mM Hepes+1 mM EDTA, pH 7.4 and homogenized with a 50-ml Dounce homogenizer and again centrifuged. After removing the supernatant, the pellets are stored at −80° C., until used in binding assay. When used in the assay, membranes are thawed on ice for 20 minutes and then 10 mL of incubation buffer (20 mM Hepes, 1 mM $MgCl_2$, 100 mM NaCl, pH 7.4) is added. The membranes are then vortexed to resuspend the crude membrane pellet and homogenized with a Brinkmann PT-3100 Polytron homogenizer for 15 seconds at setting 6. The concentration of membrane protein is determined using the BRL Bradford protein assay.

B. Binding Assay

For total binding, a total volume of 50 μl of appropriately diluted membranes (diluted in assay buffer containing 50 mM Tris HCl (pH 7.4), 10 mM $MgCl_2$, and 1 mM EDTA; 5-50 μg protein) is added to 96-well polyproylene microtiter plates followed by addition of 100 μl of assay buffer and 50 μl of radiolabelled Compound X. For nonspecific binding, 50 μl of assay buffer is added instead of 100 μl and an additional 50 μl of 10 μM cold GPR35 is added before 50 μl of radiolabelled Compound X is added. Plates are then incubated at room temperature for 60-120 minutes. The binding reaction is terminated by filtering assay plates through a Microplate Devices GF/C Unifilter filtration plate with a Brandell 96-well plate harvestor followed by washing with cold 50 mM Tris HCl, pH 7.4 containing 0.9% NaCl. Then, the bottom of the filtration plates are sealed, 50 μl of Optiphase Supermix is added to each well, the top of the plates are sealed, and plates are counted in a Trilux MicroBeta scintillation counter. For compound competition studies, instead of adding 100 μl of assay buffer, 100 μl of appropriately diluted candidate compound is added to appropriate wells followed by addition of 50 μl of radiolabelled Compound X.

C. Calculations

The candidate compounds are initially assayed at 1 and 0.1 μM and then at a range of concentrations chosen such that the middle dose would cause about 50% inhibition of a radiolabelled Compound X binding (i.e., $IC_{50}$). Specific binding in the absence of candidate compound ($B_O$) is the difference of total binding ($B_T$) minus non-specific binding (NSB) and similarly specific binding (in the presence of candidate compound) (B) is the difference of displacement binding ($B_D$) minus non-specific binding (NSB). $IC_{50}$ is determined from an inhibition response curve, logit-log plot of % $B/B_O$ vs concentration of candidate compound.

$K_i$ is calculated by the Cheng and Prustoff transformation:

$$K_i = IC_{50}/(1+[L]/K_D)$$

where [L] is the concentration of a radiolabelled Compound X used in the assay and $K_D$ is the dissociation constant of a radiolabelled Compound X determined independently under the same binding conditions.

Example 21

Rodent Diabetes Model

Rodent models of type 2 diabetes associated with obesity and insulin resistance have been developed. Genetic models such as db/db and ob/ob [see Diabetes (1982) 31:1-6] in mice and fa/fa in zucker rats have been developed for understanding the pathophysiology of disease and for testing candidate therapeutic compounds [Diabetes (1983) 32:830-838; Annu Rep Sankyo Res Lab (1994) 46:1-57]. The homozygous animals, C57 BL/KsJ-db/db mice developed by Jackson Laboratory are obese, hyperglycemic, hyperinsulinemic and insulin resistant [J Clin Invest (1990) 85:962-967], whereas heterozygotes are lean and normoglycemic. In the db/db model, mice progressively develop insulinopenia with age, a feature commonly observed in late stages of human type 2 diabetes when sugar levels are insufficiently controlled. Since this model resembles that of human type 2 diabetes, the compounds of the present invention are tested for activities including, but not limited to, lowering of plasma glucose and triglycerides. Zucker (fa/fa) rats are severely obese, hyperinsulinemic, and insulin resistant {Coleman, Diabetes (1982) 31:1; E Shafrir in Diabetes Mellitus, H Rifkin and D Porte, Jr, Eds [Elsevier Science Publishing Co, New York, ed. 4, (1990), pp. 299-340]}, and the fa/fa mutation may be the rat equivalent of the murine db mutation [Friedman et al, Cell (1992) 69:217-220; Truett et al, Proc Natl Acad Sci USA (1991) 88:7806]. Tubby (tub/tub) mice are characterized by obesity, moderate insulin resistance and hyperinsulinemia without significant hyperglycemia [Coleman et al, Heredity (1990) 81:424].

The present invention encompasses the use of compounds of the invention for reducing the insulin resistance and hyperglycemia in any or all of the above rodent diabetes models, in humans with type 2 diabetes or other preferred metabolic-related disorders or disorders of lipid metabolism described previously, or in models based on other mammals. Plasma glucose and insulin levels can be tested, as well as other factors including, but not limited to, plasma free fatty acids and triglycerides.

In Vivo Assay for Anti-Hyperglycemic Activity of Compounds of the Invention

Genetically altered obese diabetic mice (db/db) (male, 7-9 weeks old) are housed (7-9 mice/cage) under standard laboratory conditions at 22° C. and 50% relative humidity, and maintained on a diet of Purina rodent chow and water ad libitum. Prior to treatment, blood is collected from the tail vein of each animal and blood glucose concentrations are determined using One Touch Basic Glucose Monitor System (Lifescan). Mice that have plasma glucose levels between 250 to 500 mg/dl are used. Each treatment group consists of seven mice that are distributed so that the mean glucose levels are equivalent in each group at the start of the study. db/db mice are dosed by micro-osmotic pumps, inserted using isoflurane anesthesia, to provide compounds of the invention, saline, or an irrelevant compound to the mice subcutaneously (s.c.). Blood is sampled from the tail vein at intervals thereafter and analyzed for blood glucose concentrations. Significant differences between groups (comparing compounds of the invention to saline-treated) are evaluated using Student t-test.

The foregoing is provided by way of illustration and not limitation. Other illustrative rodent models for type 2 diabetes have been described [Moller D E, Nature (2001) 414:821-7 and references therein; and Reed M J et al., Diabetes, Obesity and Metabolism (1999) 1:75-86 and reference therein; the disclosure of each of which is hereby incorporated by reference in its entirety].

Example 22

Mouse Atherosclerosis Model

Adiponectin-deficient mice generated through knocking out the adiponectin gene have been shown to be predisposed to atherosclerosis and to be insulin resistant. The mice are also a suitable model for ischemic heart disease [Matsuda, M et al. J Biol Chem (2002) July, and references cited therein, the disclosures of which are incorporated herein by reference in their entirety].

Adiponectin knockout mice are housed (7-9 mice/cage) under standard laboratory conditions at 22° C. and 50% relative humidity. The mice are dosed by micro-osmotic pumps, inserted using isoflurane anesthesia, to provide compounds of the invention, saline, or an irrelevant compound to the mice subcutaneously (s.c.). Neointimal thickening and ischemic heart disease are determined for different groups of mice sacrificed at different time intervals. Significant differences between groups (comparing compounds of the invention to saline-treated) are evaluated using Student t-test.

The foregoing mouse model of atherosclerosis is provided by way of illustration and not limitation. By way of further example, Apolipoprotein E-deficient mice have also been shown to be predisposed to atherosclerosis [Plump AS et al., Cell (1992) 71:343-353; the disclosure of which is hereby incorporated by reference in its entirety].

Another model that can be used is that of diet-induced atherosclerosis in C57BL/6J mice, an inbred strain known to be susceptible to diet-induced atherosclerotic lesion formation. This model is well known to persons of ordinary skill in the art [Kamada N et al., J Atheroscler Thromb (2001) 8:1-6; Garber D W et al., J Lipid Res (2001) 42:545-52; Smith J D et al., J Intern Med (1997) 242:99-109; the disclosure of each of which is hereby incorporated by reference in its entirety].

Example 23

In Vivo Pig Model of HDL-Cholesterol and Atherosclerosis

The utility of a compound of the present invention as a medical agent in the prevention or treatment of a high total cholesterol/HDL-cholesterol ratio and conditions relating thereto is demonstrated, for example, by the activity of the compound in lowering the ratio of total cholesterol to HDL-cholesterol, in elevating HDL-cholesterol, or in protection from atherosclerosis in an in vivo pig model. Pigs are used as an animal model because they reflect human physiology, especially lipid metabolism, more closely than most other animal models. An illustrative in vivo pig model not intended to be limiting is presented here.

Yorkshire albino pigs (body weight 25.5±4 kg) are fed a saturated fatty acid rich and cholesterol rich (SFA-CHO) diet during 50 days (1 kg chow 35 kg−1 pig weight), composed of standard chow supplemented with 2% cholesterol and 20% beef tallow [Royo T et al., European Journal of Clinical Investigation (2000) 30:843-52]. Saturated to unsaturated fatty acid ratio is modified from 0.6 in normal pig chow to 1.12 in the SFA-CHO diet. Animals are divided into two groups, one group (n=8) fed with the SFA-CHO diet and treated with placebo and one group (n=8) fed with the SFA-CHO diet and treated with the modulator (3.0 mg kg-1). Control animals are fed a standard chow for a period of 50 days. Blood samples are collected at baseline (2 days after the reception of the animals), and 50 days after the initiation of the diet. Blood lipids are analyzed. The animals are sacrificed and necropsied.

Alternatively, the foregoing analysis comprises a plurality of groups each treated with a different dose of the compound of interest. Doses include, for example: 0.1 mg kg-1, 0.3 mg kg-1, 1.0 mg kg-1, 3.0 mg kg-1, 10 mg kg-1, 30 mg kg-1 and 100 mg kg-1. Alternatively, the foregoing analysis is carried out at a plurality of timepoints, for example, 10 weeks, 20 weeks, 30 weeks, 40 weeks, and 50 weeks.

HDL-Cholesterol:

Blood is collected in trisodium citrate (3.8%, 1:10). Plasma is obtained after centrifugation (1200 g 15 min) and immediately processed. Total cholesterol, HDL-cholesterol, and LDL-cholesterol are measured using the automatic analyzer Kodak Ektachem DT System (Eastman Kodak Company, Rochester, N.Y., USA). Samples with value parameters above the range are diluted with the solution supplied by the manufacturer and then re-analyzed. The total cholesterol/HDL-cholesterol ratio is determined. Comparison is made of the level of HDL-cholesterol between groups. Comparison is made of the total cholesterol/HDL-cholesterol ratio between groups.

Elevation of HDL-cholesterol or reduction of the total cholesterol/HDL-cholesterol ratio on administration of the compound of interest is taken as indicative of the compound having the aforesaid utility.

Atherosclerosis:

The thoracic and abdominal aortas are removed intact, opened longitudinally along the ventral surface, and fixed in neutral-buffered formalin after excision of samples from standard sites in the thoracic and abdominal aorta for histological examination and lipid composition and synthesis studies. After fixation, the whole aortas are stained with Sudan IV and pinned out flat, and digital images are obtained with a TV camera connected to a computerized image analysis system (Image Pro Plus; Media Cybernetics, Silver Spring, Md.) to determine the percentage of aortic surface involved with atherosclerotic lesions [Gerrity R G et al, Diabetes (2001) 50:1654-65; Cornhill J F et al, Arteriosclerosis, Thrombosis, and Vascular Biology (1985) 5:415-26; which disclosures are hereby incorporated by reference in their entirety]. Comparison is made between groups of the percentage of aortic surface involved with atherosclerotic lesions.

Reduction of the percentage of aortic surface involved with atherosclerotic lesions on administration of the compound of interest is taken as indicative of the compound having the aforesaid utility.

Plasma Free Fatty Acids:

It would be readily apparent to anyone of ordinary skill in the art that the foregoing in vivo pig model is easily modified in order to address, without limitation, the activity of the compound in lowering plasma free fatty acids.

Those skilled in the art will recognize that various modifications, additions, substitutions, and variations to the illustrative examples set forth herein can be made without departing from the spirit of the invention and are, therefore, considered within the scope of the invention. All journal research publications listed herein are incorporated herein by reference in their entirety.

We claim:

1. A method for identifying a metabolic-stabilizing compound, comprising:
   a) contacting a candidate compound with G protein-coupled receptor 35 (GPR35), wherein the GPR35 is coupled to Gi, and
   b) determining whether GPR35 functionality is increased, wherein the candidate compound is identified as being a metabolic-stabilizing compound when GPR35 functionality is increased.

2. The method of claim 1, wherein said GPR35 is human.

3. The method of claim 1, wherein said determining comprises a second messenger assay.

4. The method of claim 1, wherein said metabolic-stabilizing compound is selected from: a metabolic-stabilizing compound that decreases blood glucose levels in an individual, a metabolic-stabilizing compound that decreases free fatty acid levels in an individual, and a metabolic-stabilizing compound that decreases both blood glucose and free fatty acid levels in an individual.

* * * * *